US012692304B2

(12) United States Patent
Rastrick et al.

(10) Patent No.: US 12,692,304 B2
(45) Date of Patent: Jul. 28, 2026

(54) ANTIBODIES AGAINST INTERLEUKIN-22

(71) Applicant: UCB BIOPHARMA SRL, Brussels (BE)

(72) Inventors: Joseph Michael David Rastrick, Slough (GB); John Paul Silva, Slough (GB); Kerry Louise Tyson, Slough (GB); Peter Charles Elliott, Slough (GB); Seppe Frans Roman Leysen, Slough (GB); Zainab Ahdash, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 545 days.

(21) Appl. No.: 18/253,240

(22) PCT Filed: Dec. 6, 2021

(86) PCT No.: PCT/EP2021/084400
§ 371 (c)(1),
(2) Date: May 17, 2023

(87) PCT Pub. No.: WO2022/122652
PCT Pub. Date: Jun. 16, 2022

(65) Prior Publication Data
US 2023/0416357 A1 Dec. 28, 2023

(30) Foreign Application Priority Data
Dec. 7, 2020 (EP) .................................... 20212127

(51) Int. Cl.
*C07K 16/24* (2006.01)
(52) U.S. Cl.
CPC ........ *C07K 16/244* (2013.01); *C07K 2317/24* (2013.01); *C07K 2317/33* (2013.01); *C07K 2317/34* (2013.01); *C07K 2317/55* (2013.01); *C07K 2317/76* (2013.01); *C07K 2317/92* (2013.01)

(58) Field of Classification Search
CPC .................................................. C07K 16/244
See application file for complete search history.

(56) References Cited

U.S. PATENT DOCUMENTS

| | | | |
|---|---|---|---|
| 6,939,545 B2 | 9/2005 | Jacobs et al. | |
| 7,737,259 B2 | 6/2010 | Chen et al. | |
| 7,901,684 B2 | 3/2011 | Gill et al. | |
| 8,906,375 B2 | 12/2014 | Fouser et al. | |
| 2002/0187512 A1 | 12/2002 | Nagem et al. | |
| 2008/0171014 A1 | 7/2008 | Wu et al. | |

FOREIGN PATENT DOCUMENTS

| | | |
|---|---|---|
| CN | 104774266 B | 3/2020 |
| EP | 1644415 A2 | 4/2006 |
| JP | 2007/537132 A | 12/2007 |
| JP | 2009/518314 A | 5/2009 |
| JP | 2009/528288 A | 8/2009 |
| JP | 2009-531023 A | 9/2009 |
| WO | 2005/000897 A2 | 1/2005 |
| WO | 2007/098170 A1 | 8/2007 |
| WO | 2007/100643 A2 | 9/2007 |
| WO | 2007/126439 A2 | 11/2007 |

OTHER PUBLICATIONS

Jin et al., "From Bench to Clinic: the Potential of Therapeutic Targeting of the IL-22 Signaling Pathway in Atopic Dermatitis," Immune Netw. 18(6):e42 (2018).
Na et al., "A Therapeutic Renaissance—Emerging Treatments for Atopic Dermatitis," Acta Derm Venereol. 100(12):adv00165 (2020).
International Search Report, International Application No. PCT/EP2021/084400, Mailing Date: Feb. 14, 2022.
Bleicher et al., "Crystal structure of the IL-22/IL-22R1 complex and its implications for the IL-22 signaling mechanism," FEBS Letters 582(20):2985-2992 (2008).
Jones et al., "Structure of IL-22 Bound to Its High-Affinity IL-22R1 Chain," Structure 16(9):1333-1344 (2008).
Sabat et al., "Therapeutic opportunities of the IL-22-IL-22R1 system," Nat Rev Drug Discov 13(1):21-38 (2014).
Chapman, "PEGylated antibodies and antibody fragments for improved therapy: a review," Advanced Drug Delivery Reviews 54:531-545 (2002).
Cleveland Clinic. Food Allergies Management and Treatment. website saved May 7, 2025.
Johns Hopkins. Eczema and Atopic Dermatitis. website saved May 7, 2025.
Smith et al., "Prolonged in Vivo residence times of antibody fragments associated with Albumin," Bioconjug. Chem. 12(5):750-756 (2001).
Boniface et al., "A role for T cell-derived interleukin 22 in psoriatic skin inflammation," Clinical and Experimental Immunology 150:407-415 (2007).
Guttman-Yassky et al., "Efficacy and safety of fezakinumab (an anti-IL-22 monoclonal antibody) in adults with moderate-to-severe atopic dermatitis inadequately controlled by conventional treatments—A randomized, double-blind, phase 2a trial," J Am Acad Dermatol. 78(5):872-881 (2018).
Lanfranca et al., "Biological and Pathological Activities of Interleukin-22," J Mol Med (Berl) 94(5):523-534 (2016).
Laughter et al., "The global burden of atopic dermatitis: lessons from the Global Burden of Disease Study 1990-2017," British Journal of Dermatology 184:304-309 (2021).

(Continued)

*Primary Examiner* — Prema M Mertz
(74) *Attorney, Agent, or Firm* — MEDLER FERRO WOODHOUSE & MILLS PLLC

(57) ABSTRACT

The present invention relates to antibodies binding to IL22 and inhibiting its interaction with one or more of its natural ligands. Specific examples of such antibodies are provided. The therapeutic uses of the antibodies and methods of generating such are also provided.

19 Claims, 11 Drawing Sheets

Specification includes a Sequence Listing.

(56) References Cited

OTHER PUBLICATIONS

Nagem et al., "Crystal Structure of Recombinant Human Interleukin-22," Structure 10:1051-1062 (2002).

Rondeau et al., "The molecular mode of action and species specificity of canakinumab, a human monoclonal antibody neutralizing IL-1β," mAbs 7(6):1151-1160 (2015).

Van Belle et al., "IL-22 Is Required for Imiquimod-Induced Psoriasiform Skin Inflammation in Mice," The Journal of Immunology 188(1):462-469 (2012).

Xu et al., "Structure of insect-cell-derived IL-22," Acta Cryst. D61:942-950 (2005).

Brunner et al., "Baseline IL-22 expression in patients with atopic dermatitis stratifies tissue responses to fezakinumab," J Allergy Clin Immunol 143(1):142-154 (2019).

Brown et al., "Tolerance of single, but not multiple, amino acid replacements in antibody VH CDR 2: a means of minimizing B cell wastage from somatic hypermutation?" J Immunol. 156(9):3285-3291 (1996).

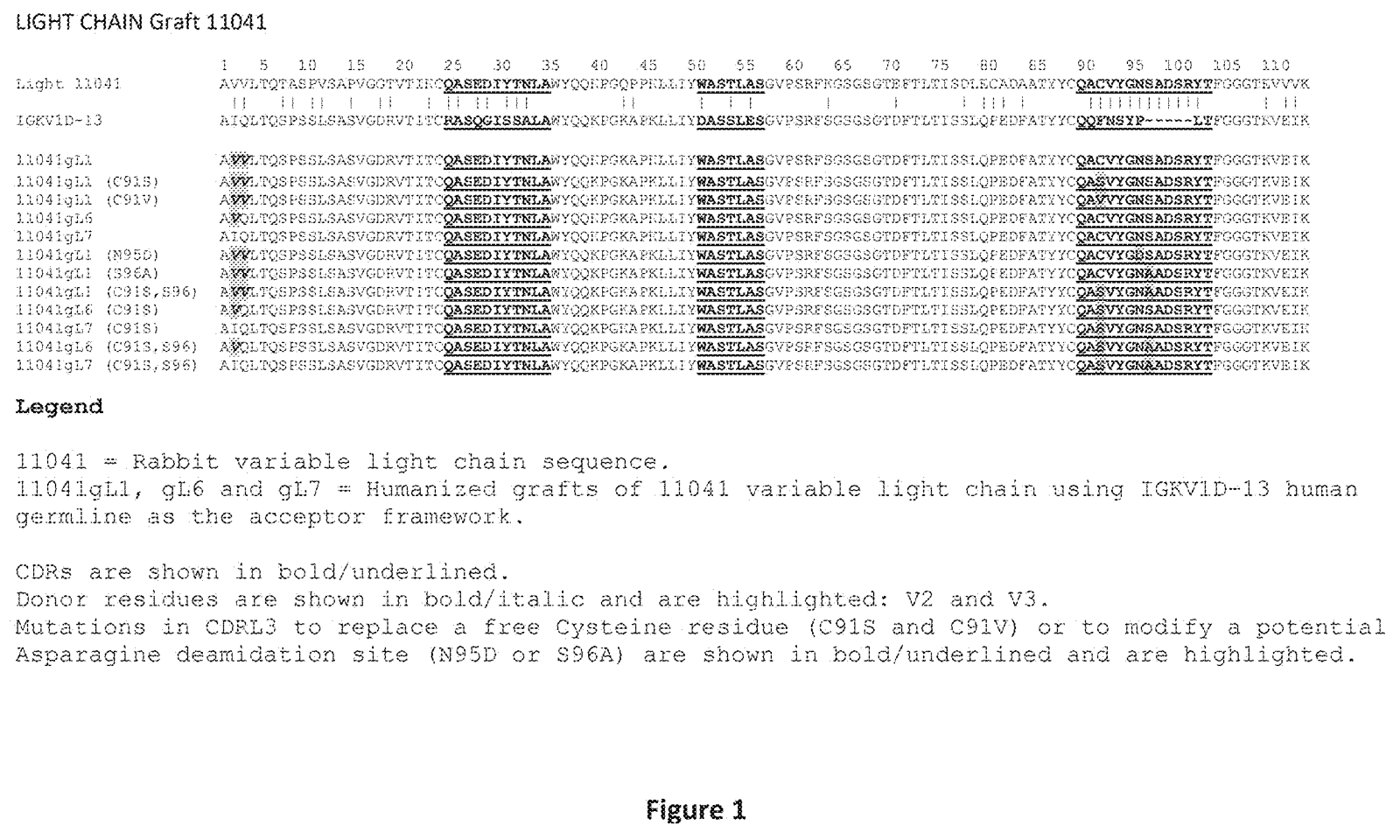

LIGHT CHAIN Graft 11041

```
                 1    5    10   15   20   25   30   35   40   45   50   55   60   65   70   75   80   85   90   95   100  105  110
Light 11041      AVVLTQTASPVSAPVGGTVTIKCQASEDIYNLAWYQRPGQPPKLLIYWASTLASGVPSRFKGSGSGTRFTLTISDLECADAATVYCQACVYGNSADSRYTFGGGTKVVVK
                  |  ||  |||||  ||  |||  |||  ||||||    |  |||||||  |||||||||||||  || |     |  |  ||||||||||
IGKV1D-13        AIQLTQSPSSLSASVGDRVTITCRASQGISSALAWYQQKPGKAPKLLIYDASSLESGVPSRFSGSGSGTDFTLTISSLQPEDFATYYCQQFNSYP------LTFGGGTKVEIK 11041gL1         AVVLTQSPSSLSASVGDRVTITCQASEDIYNLAWYQQKPGKAPKLLIYWASTLASGVPSRFSGSGSGTDFTLTISSLQPEDFATYYCQACVYGNSADSRYTFGGGTKVEIK
11041gL1 (C91S)  AVVLTQSPSSLSASVGDRVTITCQASEDIYNLAWYQQKPGKAPKLLIYWASTLASGVPSRFSGSGSGTDFTLTISSLQPEDFATYYCQASVYGNSADSRYTFGGGTKVEIK
11041gL1 (C91V)  AVVLTQSPSSLSASVGDRVTITCQASEDIYNLAWYQQKPGKAPKLLIYWASTLASGVPSRFSGSGSGTDFTLTISSLQPEDFATYYCQAVVYGNSADSRYTFGGGTKVEIK
11041gL6         AIQLTQSPSSLSASVGDRVTITCQASEDIYNLAWYQQKPGKAPKLLIYWASTLASGVPSRFSGSGSGTDFTLTISSLQPEDFATYYCQACVYGNSADSRYTFGGGTKVEIK
11041gL7         AIQLTQSPSSLSASVGDRVTITCQASEDIYNLAWYQQKPGKAPKLLIYWASTLASGVPSRFSGSGSGTDFTLTISSLQPEDFATYYCQACVYGNSADSRYTFGGGTKVEIK
11041gL1 (N95D)  AVVLTQSPSSLSASVGDRVTITCQASEDIYTNLAWYQQKPGKAPKLLIYWASTLASGVPSRFSGSGSGTDFTLTISSLQEEDFATYYCQACVYGDSADSRYTFGGGTKVEIK
11041gL1 (S96A)  AVVLTQSPSSLSASVGDRVTITCQASEDIYTNLAWYQQKPGKAPKLLIYWASTLASGVPSRFSGSGSGTDFTLTISSLQEEDFATYYCQACVYGNAADSRYTFGGGTKVEIK
11041gL1 (C91S,S96) AVVLTQSPSSLSASVGDRVTITCQASEDIYTNLAWYQQKPGKAPKLLIYWASTLASGVPSRFSGSGSGTDFTLTISSLQPEDFATYYCQASVYGNAADSRYTFGGGTKVEIH
11041gL6 (C91S)  AIQLTQSPSSLSASVGDRVTITCQASEDIYTNLAWYQQKPGKAPKLLIYWASTLASGVPSRFSGSGSGTDFTLTISSLQPEDFATYYCQASVYGNSADSRYTFGGGTKVEIH
11041gL7 (C91S)  AIQLTQSPSSLSASVGDRVTITCQASEDIYTNLAWYQQKPGKAPKLLIYWASTLASGVPSRFSGSGSGTDFTLTISSLQPEDFATYYCQASVYGNSADSRYTFGGGTKVEIK
11041gL6 (C91S,S96) AIQLTQSPSSLSASVGDRVTITCQASEDIYTNLAWYQQKPGKAPKLLIYWASTLASGVPSRFSGSGSGTDFTLTISSLQPEDFATYYCQASVYGNAADSRYTFGGGTKVEIK
11041gL7 (C91S,S96) AIQLTQSPSSLSASVGDRVTITCQASEDIYTNLAWYQQKPGKAPKLLIYWASTLASGVPSRFSGSGSGTDFTLTISSLQPEDFATYYCQASVYGNAADSRYTFGGGTKVEIK
```

Legend

11041 = Rabbit variable light chain sequence.
11041gL1, gL6 and gL7 = Humanized grafts of 11041 variable light chain using IGKV1D-13 human germline as the acceptor framework.

CDRs are shown in bold/underlined.
Donor residues are shown in bold/italic and are highlighted.
Mutations in CDRL3 to replace a free Cysteine residue (C91S and C91V) or to modify a potential Asparagine deamidation site (N95D or S96A) are shown in bold/underlined and are highlighted.

Figure 1

Figure 2:
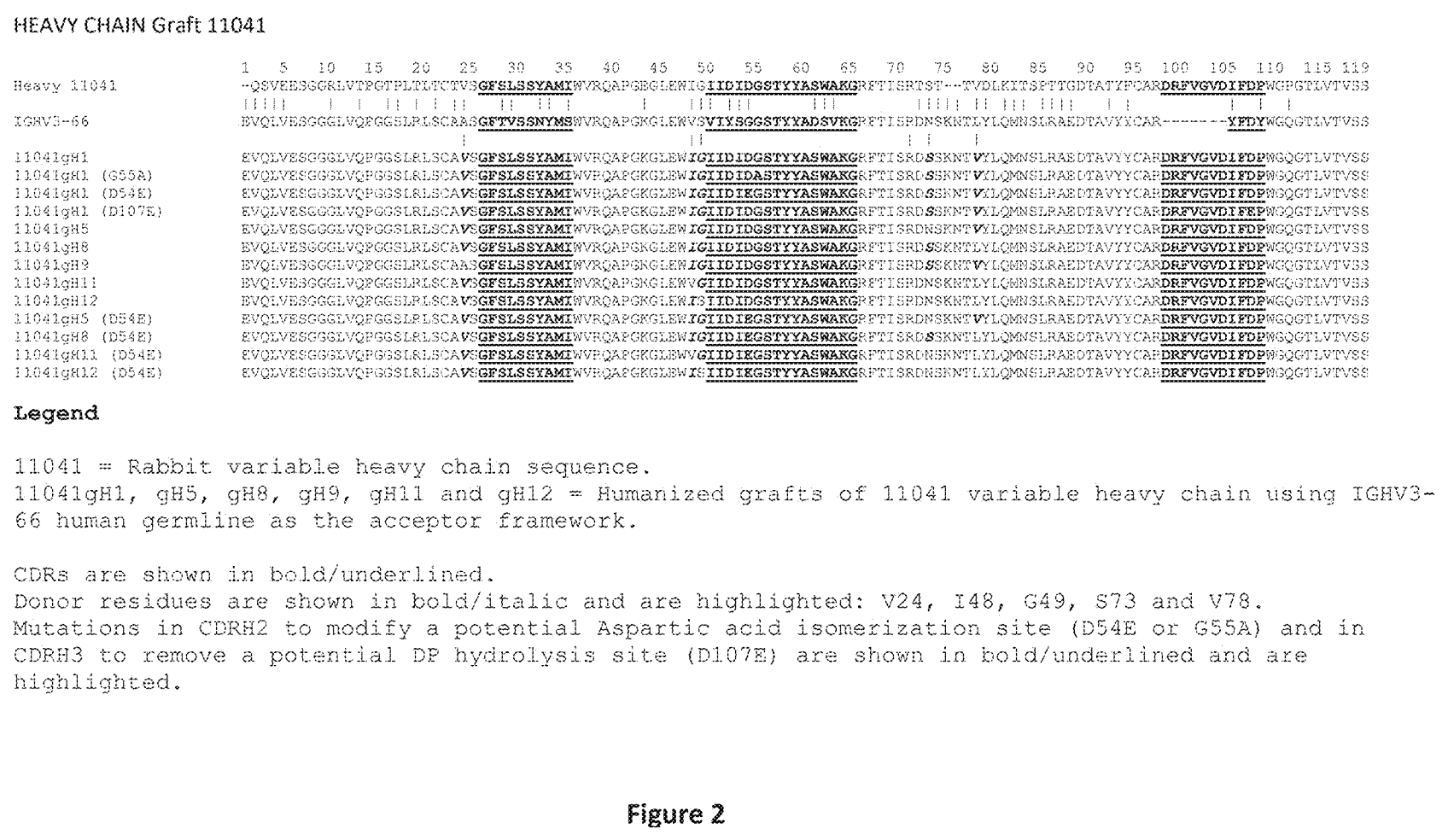

HEAVY CHAIN Graft 11041

Legend

11041 = Rabbit variable heavy chain sequence.
11041gH1, gH5, gH8, gH9, gH11 and gH12 = Humanized grafts of 11041 variable heavy chain using IGHV3-66 human germline as the acceptor framework.

CDRs are shown in bold/underlined.
Donor residues are shown in bold/italic and are highlighted: V24, I48, G49, S73 and V78.
Mutations in CDRH2 to modify a potential Aspartic acid isomerization site (D54E or G55A) and in CDRH3 to remove a potential DP hydrolysis site (D107E) are shown in bold/underlined and are highlighted.

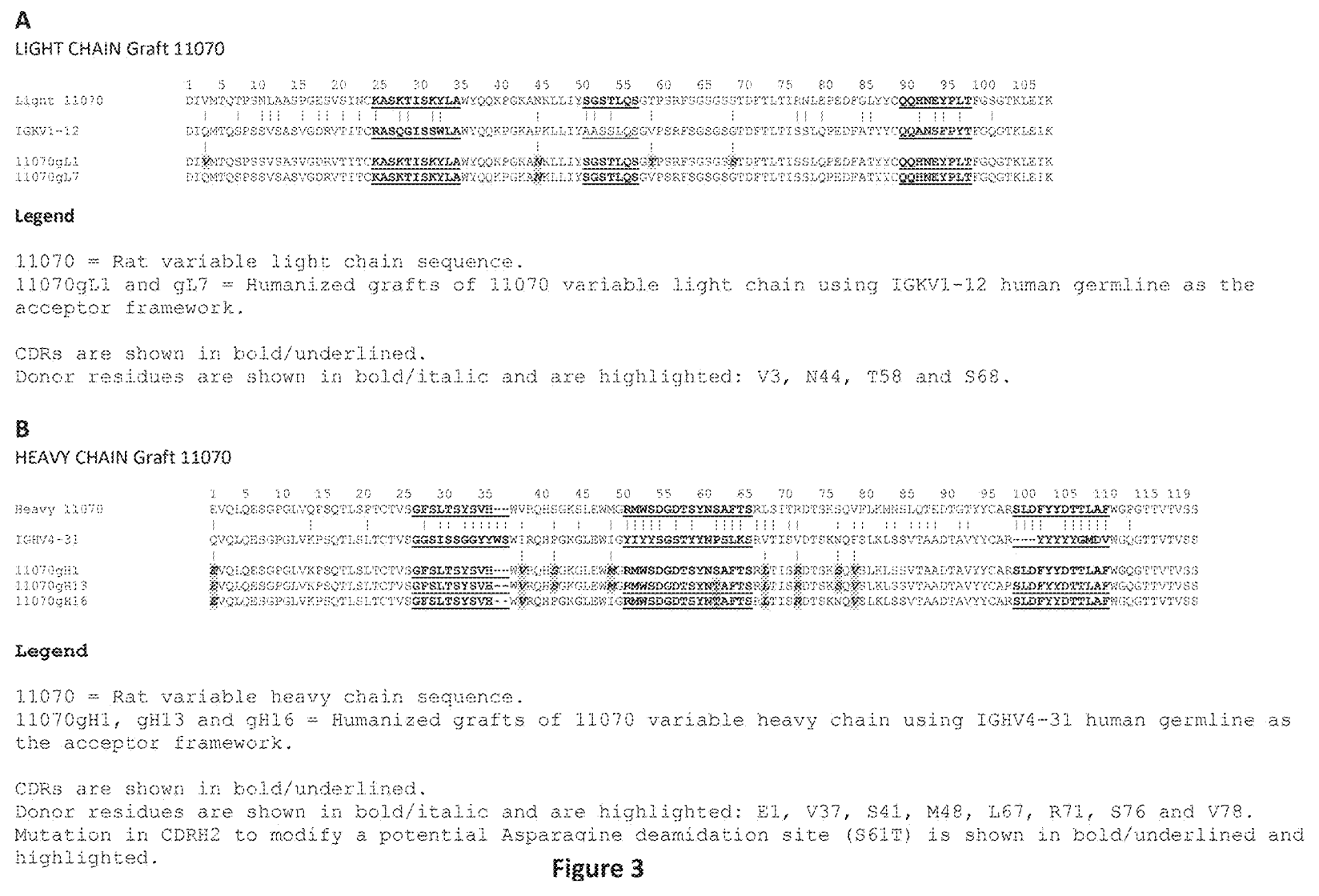

LIGHT CHAIN Graft 11070

Legend

11070 = Rat variable light chain sequence.
11070gL1 and gL7 = Humanized grafts of 11070 variable light chain using IGKV1-12 human germline as the acceptor framework.

CDRs are shown in bold/underlined.
Donor residues are shown in bold/italic and are highlighted: V3, N44, T58 and S68.

B

HEAVY CHAIN Graft 11070

Legend

11070 = Rat variable heavy chain sequence.
11070gH1, gH13 and gH16 = Humanized grafts of 11070 variable heavy chain using IGHV4-31 human germline as the acceptor framework.

CDRs are shown in bold/underlined.
Donor residues are shown in bold/italic and are highlighted: E1, V37, S41, M48, L67, R71, S76 and V78.
Mutation in CDRH2 to modify a potential Asparagine deamidation site (S61T) is shown in bold/underlined and highlighted.

Figure 3

(a)
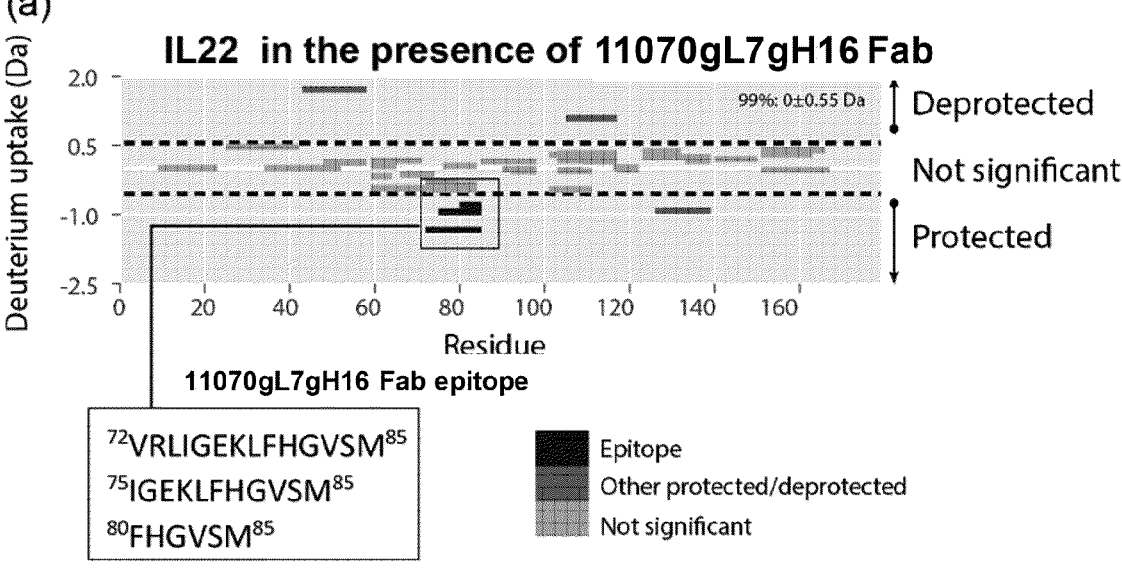
11070gL7gH16 Fab epitope
$^{72}$VRLIGEKLFHGVSM$^{85}$
$^{75}$IGEKLFHGVSM$^{85}$
$^{80}$FHGVSM$^{85}$
Epitope
Other protected/deprotected
Not significant
(b)
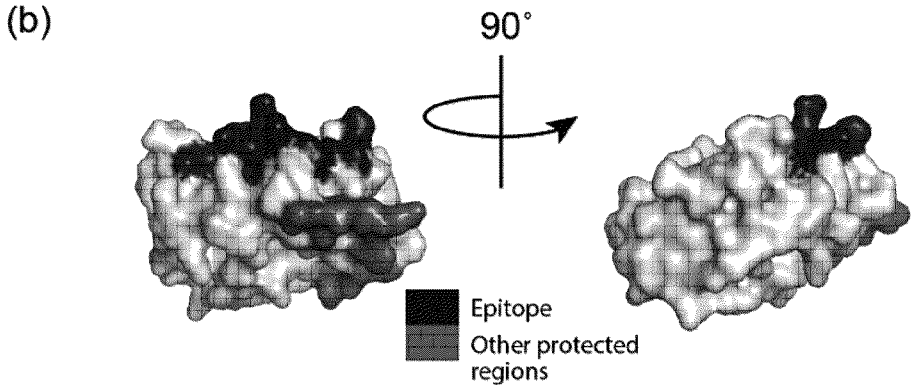
90°
Epitope
Other protected regions
Figure 6

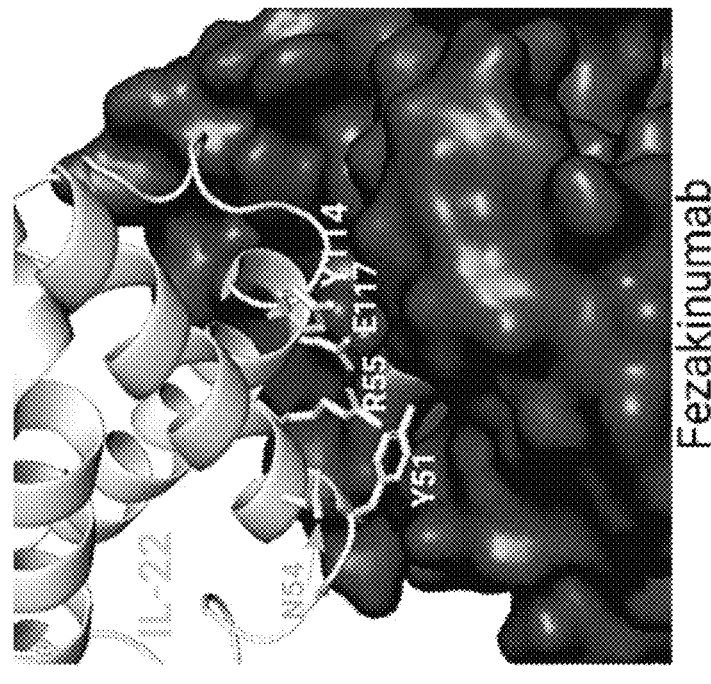
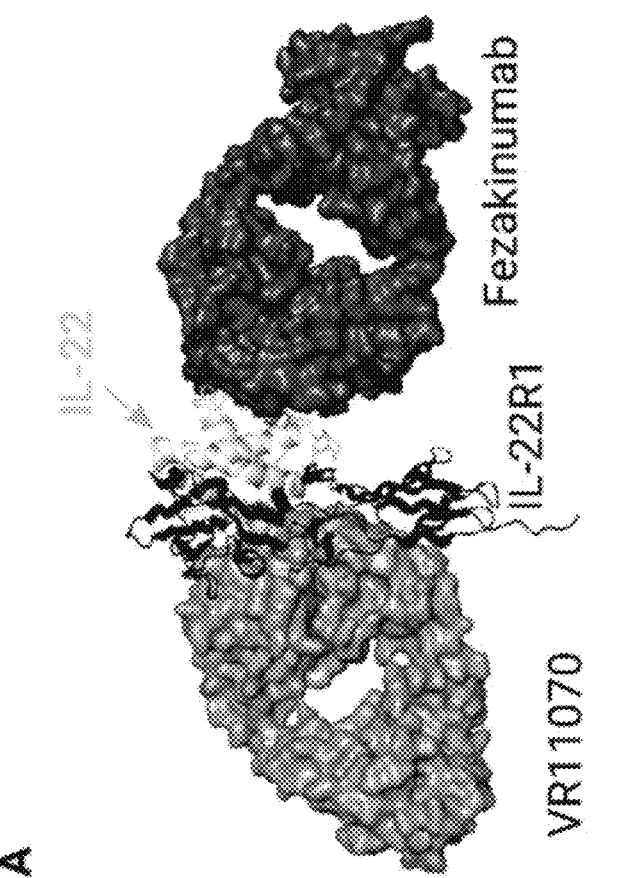
Figure 10

A
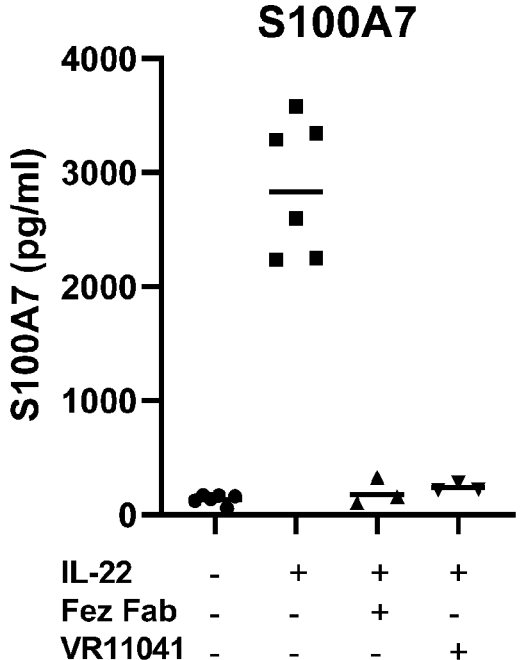
B
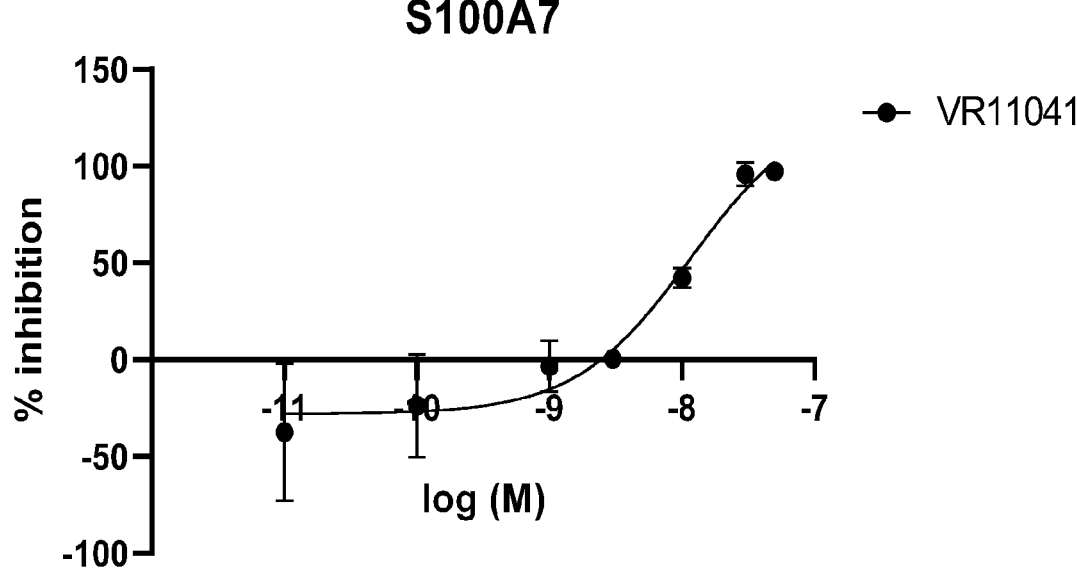
Figure 11

ANTIBODIES AGAINST INTERLEUKIN-22

FIELD OF THE INVENTION

The present invention relates to anti-IL22 antibodies. Such antibodies provided herein are useful in the treatment of skin inflammation, in particular, of atopic dermatitis.

BACKGROUND

Atopic dermatitis (AD), also known as atopic eczema, is an inflammatory condition which results in epidermal dysfunction and thickening, eczematous lesions and pruritis. The condition is prevalent in people of all ages and ethnicities and has the greatest disease burden of all skin diseases measured by disability-adjusted life years (Laughter et al, Br. J. Dermatol. 2020; Epub ahead of print). AD is a complex condition and its pathophysiology is influenced by multiple factors, such as genetics, environmental and immunological factors. Although type-2 immune mechanisms are important in the pathology of atopic dermatitis, increasing evidence supports a role for several immune pathways.

Treatments used for AD include systemic immunosuppressants such as cyclosporin, methotrexate, mycophenolate mofetil and azathioprine. Antidepressants and naltrexone may be used to control pruritus. In 2016, crisaborole, a topical phosphodiesterase-4 inhibitor, was approved for mild-to-moderate eczema, and in 2017, dupilumab, a monoclonal antibody antagonist of IL-4Rα was approved to treat moderate-to-severe eczema. Current treatment options however, offer only temporary, incomplete, symptomatic relief.

IL22 is a member of the IL10 cytokine family with multiple functions in various inflammatory and tissue responses, depending on the environmental context. IL22 is mainly produced by lymphoid cells such as T helper 1 (Th1) cells, Th17 cells, and Th22 cells, γδ T cells, Natural Killer (NK) cells and innate lymphoid cells (ILCs) 3 as well as non-lymphoid cells such as fibroblasts, neutrophils, macrophages and mast cells (For an overview see: Lanfranca M P, et al J. Mol. Med. (Berl) (2016) 94(5):523-534). IL22 signals through a heterodimeric transmembrane receptor complex composed of IL22 receptor 1 (IL22R1, also known as IL22RA1, or as Interleukin-22 receptor subunit alpha-1) and IL-10 receptor 2 (IL10R2), whereas IL-10 signals through IL10R1 and IL-10R2. Similar to other members of the IL-10 family, IL22 mediates its effects through the IL22R1/IL-10R2 complex and subsequent JAK-signal transducer and activator of transcription (STAT) signaling pathways, including Jak1, Tyk2, and STAT3. In contrast to IL-10, IL22 is also reported to signal through a number of MAPK pathways such as ERK1/2, JNK and p38. In the skin, IL22 acts on keratinocytes through binding to IL22R1 expressed on these cells.

Unlike other members of the IL10 cytokine family, IL22 has a soluble-secreted receptor, known as IL22 binding protein (IL22BP, also known as IL22RA2, or as Interleukin-22 Receptor Subunit Alpha 2). Although IL22BP shares the highest structural homology with the IL22R1 chain, IL22BP exhibits a much higher affinity for IL22 than IL22R1 and therefore prevents the binding of IL22 to IL22R1

It has been shown that IL22BP, which is specific for IL22, blocks its activity. Inhibition of total IL22 has shown efficacious signals in patients with severe atopic dermatitis or in patients with high baseline IL22 expression (Guttman-Yassky E et al. J Am Acad Dermatol. 2018; 78(5): 872-881 and Brunner P M et al, J Allergy Cin Immunol. 2019; 143(1): 142-154). Inhibition of the IL22R1 has also been proposed as a potential therapeutic option to inhibit IL22 which would also partially block the effect of IL-20 and IL-24. To date, no therapeutic option exists that is designed to specifically target biologically active IL22 that is not bound to IL22BP, thus not impacting on the normal biological function of IL22BP.

Increased expression of Th22 cytokine IL22 is a characteristic finding in atopic dermatitis (AD). However, the specific role of IL22 in the pathogenesis of AD in vivo is not completely understood. The role of IL22 in the development and maintenance of AD has not been specifically explored but it has been hypothesized that IL22 plays an important role in the development of AD by impairing skin barrier function, immune dysregulation, and pruritus.

U.S. Pat. Nos. 8,906,375 and 7,901,684 disclose antibodies binding IL22 and usefulness of such antibodies in the treatment of AD. U.S. Pat. No. 7,737,259 discloses specific anti-IL22 antibodies useful in the treatment of psoriasis.

SUMMARY OF THE INVENTION

The present invention addresses the need for new treatments of atopic dermatitis by providing anti-IL22 antibodies with the functional and structural properties as described herein.

The present invention provides an isolated antibody that binds human interleukin 22 (IL22), wherein the antibody is capable of inhibiting or attenuating IL22 binding to IL22 receptor 1 (IL22R1) and IL22 binding protein (IL22RA2).

The present invention also provides an isolated antibody that binds human IL22 that is defined by a set of specific CDR sequences and/or variable region sequences.

BRIEF DESCRIPTION OF THE DRAWINGS

The present invention is described below by reference to the following drawings, in which:

FIG. 1 shows humanization of antibody 11041 light chain. Variants generated for that chain are also shown. The CDR sequences are underlined.

FIG. 2 shows humanization of antibody 11041 heavy chain. Variants generated for that chain are also shown. The CDR sequences are underlined.

FIG. 3A shows humanization of antibody 11070 light chain. Variants for that chain are also shown. The CDR sequences are underlined. FIG. 3B shows humanization of antibody 11070 heavy chain. Variants generated for that chain are also shown. The CDR sequences are underlined.

FIG. 6 shows the results of HDX-MS analysis for 11070gL7gH16 Fab. (A) peptides showing significant reduced deuterium incorporation upon antibody binding are listed. Peptides showing a similar exchange pattern in the presence and absence of the antibody have a non-significant deuterium incorporation and are displayed in light grey. (B)

determined 11070gL7gH16 Fab epitope is projected onto the IL22 3D structure and highlighted in black.

Figure 7:
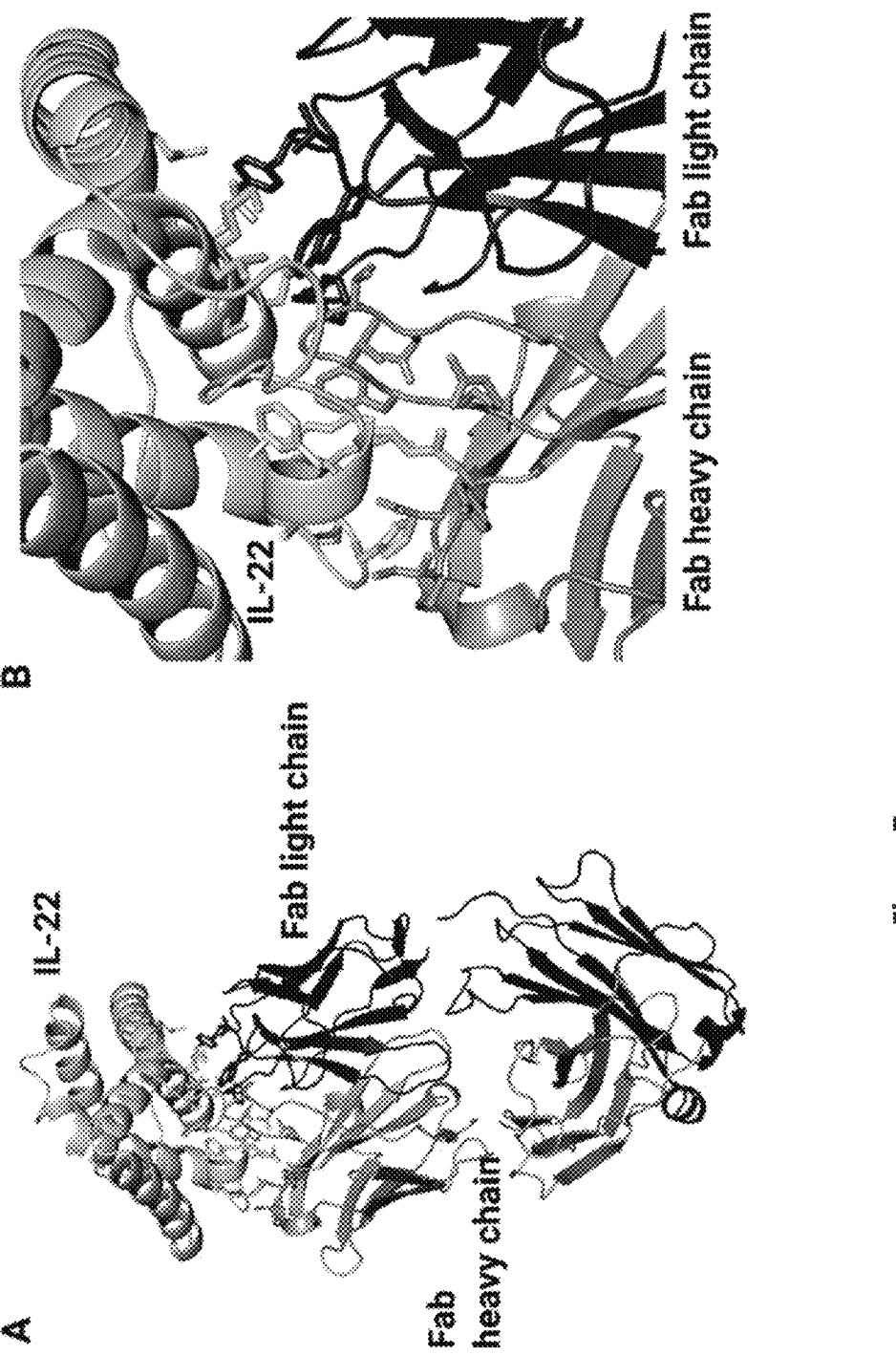

FIG. 7 shows the results of X-ray analysis of 11041gL13gH14 Fab binding to IL22. (A) cartoon representation of 11041gL13gH14 Fab binding to IL-22. (B) a detailed view on the interaction interface between IL-22 and of 11041gL13gH14 Fab.

Figure 8:
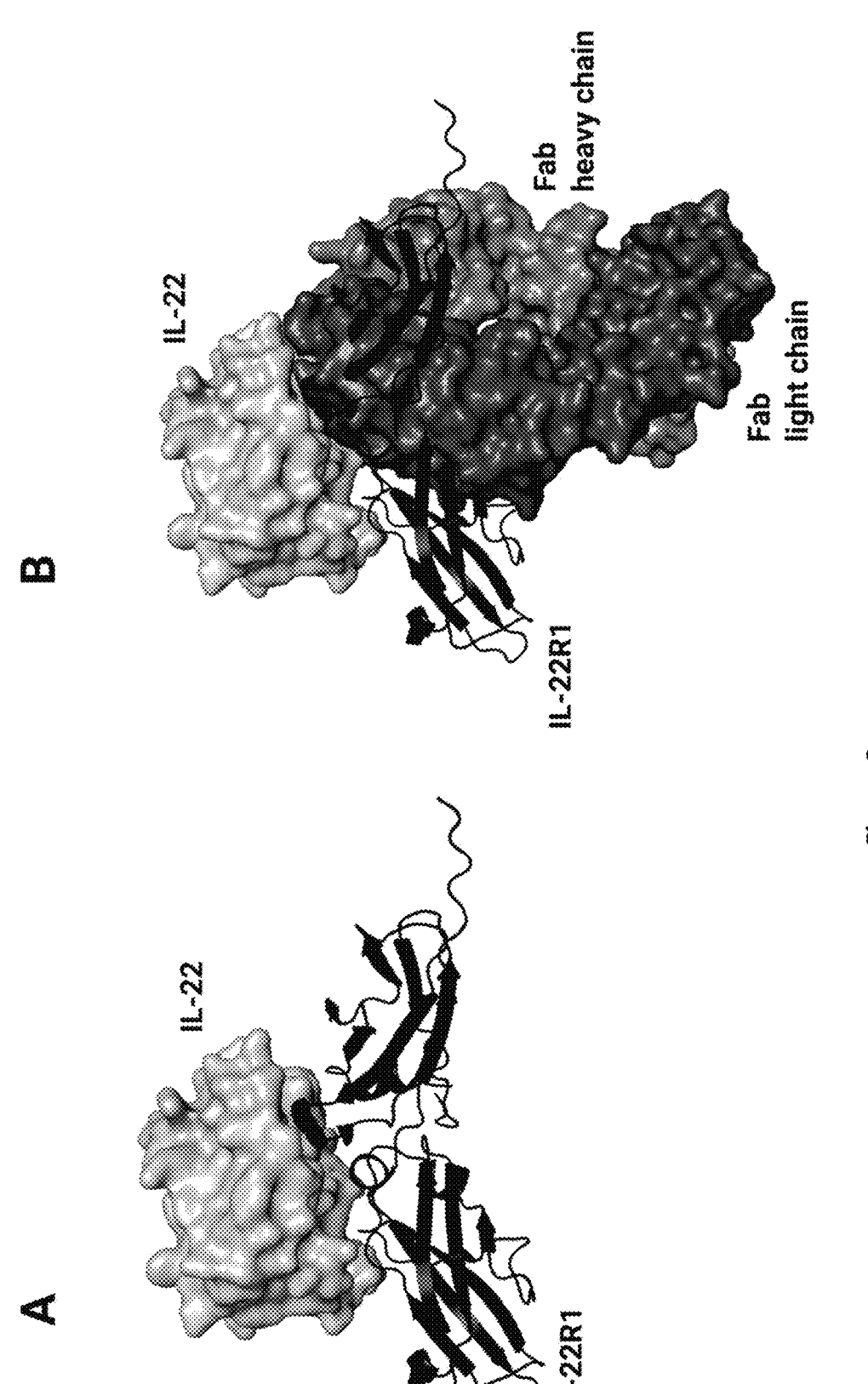

FIG. 8 shows that 11041gL13gH14 Fab molecule prevents the interaction of IL22 with the IL22R1 receptor (A) IL-22 (surface representation) in complex with its receptor IL22R1 (PDB: 3DLQ). (B) The light chain of 11041gL13gH14 Fab light chain blocks the interaction site between IL22 and IL22R1.

Figure 9:
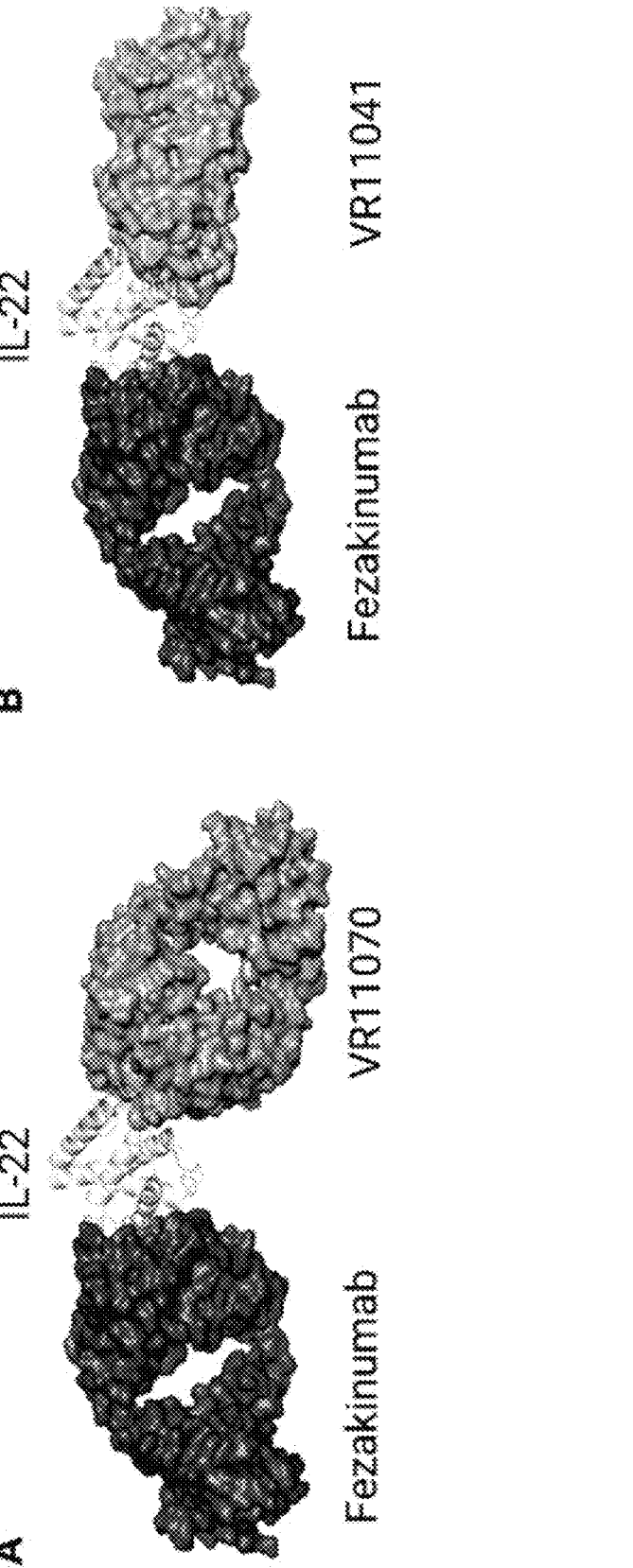

FIG. 9 shows in (A) Cryo-EM structure of IL-22 in complex with Fezakinumab and 11070gL7gH16 Fab (VR11070) in Fab format; and in (B) Model of IL-22 in complex with Fezakinumab and 11041 Fab (VR11041). The model was created by superposing the IL-22/11041gL13gH14 Fab crystal structure on the cryo-EM structure in panel (A). This reveals that 11070gL7gH16 Fab and 11041gL13gH14 Fab have a similar epitope on IL-22.

FIG. 10 shows in (A) superposition of the crystal structure of IL-22R1 bound to IL-22, on the cryo-EM structure of IL-22 in complex with 11070gL7gH16 Fab and Fezakinumab Fab; and in (B) The sidechains of IL-22 residues known to contribute to the interaction with IL-10R2 are shown as sticks. This site is occupied by the Fezakinumab Fab molecule.

FIG. 11 shows 11041gL13gH14 Fab (VR11041) activity in the in vitro human primary keratinocyte assay. (A) Example of S100A7 response in the assay. Donor lot #438Z014, Geometric mean n=3/6, Stimulation: IL-22 at 100 ng/ml, Fezakinumab Fab and 11041gL13gH14 Fab at 50 nM; (B) Percentage inhibition of S100A7 by 11041gL13gH14 Fab in the assay. Mean±SD, n=2 donors, Stimulation: IL-22 at 100 ng/ml, Statistic: log(inhibitor) vs. response (three parameters).

DETAILED DESCRIPTION OF THE INVENTION

Abbreviations

TABLE 1

| Abbreviations used throughout the specification | |
|---|---|
| ADCC | antibody-dependent cellular cytotoxicity |
| CDC | complement dependent cytotoxicity |
| CDR | complementarity-determining region |
| CH1, CH2, CH3 | constant heavy domain |
| CL | constant light |
| dsscFv | disulphide stabilised scFv |
| Fab | fragment antigen-binding |
| Fc | fragment crystallizable |
| FR1, FR2, FR3, FR4 | framework region |
| Fv | variable domain |
| HVR | hyper-variable region |
| KD | constant of dissociation |
| mAb | monoclonal antibody |
| scFv | single chain variable-fragment |
| VH | variable heavy region |
| VHH | single domain antibody |
| VL | variable light region |
| VNAR | variable domain of IgNAR |

TABLE 2

| Amino acids abbreviations | | |
|---|---|---|
| Abbreviation | 1 letter abbreviation | Amino acid name |
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Pyl | O | Pyrrolysine |
| Ser | S | Serine |
| Sec | U | Selenocysteine |
| Thr | T | Threonine |
| Trp | W | Tryptophan |
| Tyr | Y | Tyrosine |
| Val | V | Valine |

Definitions

The following terms are used throughout the specification.

The term "acceptor human framework" is used herein is a framework comprising the amino acid sequence of a light chain variable domain (VL) framework or a heavy chain variable domain (VH) framework derived from a human immunoglobulin framework or a human consensus framework. An acceptor human framework derived from a human immunoglobulin framework or a human consensus framework may comprise the same amino acid sequence thereof, or it may contain amino acid sequence changes.

The term "affinity" refers to the strength of all noncovalent interactions between an antibody thereof and the target protein. Unless indicated otherwise, as used herein, the term "binding affinity" refers to intrinsic binding affinity which reflects a 1:1 interaction between members of a binding pair (e.g., antibody and antigen). The affinity of a molecule for its binding partner can be generally represented by the dissociation constant (KD). Affinity can be measured by common methods known in the art, including those described herein.

The term "affinity matured" in the context of antibody refers to an antibody with one or more alterations in the hypervariable regions, compared to a parent antibody which does not possess such alterations, where such alterations resulting in an improvement in the affinity of the antibody for antigen.

The term "antibody" herein is used in the broadest sense and encompasses various antibody structures, including but not limited to monoclonal antibodies, polyclonal antibodies, and multi-specific antibodies as long as they exhibit the desired antigen-binding activity. The term antibody as used herein relates to whole (full-length) antibodies (i.e. comprising the elements of two heavy chains and two light chains) and functionally active fragments thereof (i.e., molecules that contain an antigen binding domain that specifically binds an antigen, also termed antibody fragments or antigen-binding fragments). Features described herein with respect to antibodies also apply to antibody fragments unless context dictates otherwise. An antibody may comprise a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibodies are described in WO2015/197772. The term "antibody" encompasses monovalent, i.e., antibodies comprising only one antigen binding domain (e.g. one-armed antibodies comprising a full-length heavy chain and a full-length light chain interconnected, also termed "half-antibody"), and multivalent antibodies, i. e. antibodies comprising more than one antigen binding domain, e.g bivalent.

The term "antibody binding to the same epitope as a reference antibody" refers to an antibody that blocks binding of the reference antibody to its antigen in a competition assay by 50% or more, and conversely, the reference antibody blocks binding of the antibody to its antigen in a competition assay by 50% or more.

The term "Antibody-dependent cellular cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells.

The term "antigen-binding fragment" as employed herein refers to functionally active antibody binding fragments including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). A "binding fragment" as employed herein refers to a fragment capable of binding a target peptide or antigen with sufficient affinity to characterize the fragment as specific for the peptide or antigen.

The term "antibody variant" refers to a polypeptide, for example, an antibody possessing the desired characteristics described herein and comprising a VH and/or a VL that has at least about 80% amino acid sequence identity with a VH and/or a VL of the reference antibody. Such antibody variants include, for instance, antibodies wherein one or more amino acid residues are added to or deleted from the VH and/or a VL domain. Ordinarily, an antibody variant will have at least about 80% amino acid sequence identity, alternatively at least about 85%, 90%, 95%, 96%, 97%, 98%, or 99% amino acid sequence identity, to an antibody described herein. Optionally, variant antibodies will have no more than one conservative amino acid substitution as compared to an antibody sequence provided herein, alternatively no more than about any of 2, 3, 4, 5, 6, 7, 8, 9, or 10 conservative amino acid substitutions as compared to an antibody sequence provided herein. In embodiments, an "antibody variant" refers to an antibody or antigen-binding fragment thereof comprising a VH and/or a VL wherein the non-CDR regions of the antibody or antigen-binding fragment thereof has at least about 85%, 90%, 95%, 96%, 97%, 98%, or 99% amino acid sequence identity, to an antibody described herein.

The term "antigen-binding domain" as employed herein refers to a portion of the antibody, which comprises a part or the whole of one or more variable domains, for example a part or the whole of a pair of variable domains VH and VL, that interact specifically with the target antigen. In the context of the present invention the term is used in relation to three different antigens: IL13, IL22, and albumin. Hence, such antigen-binding domains are referred to as "IL13-binding domain", "IL22-binding domain", and "albumin-binding domain". A binding domain may comprise a single domain antibody. Each binding domain may be monovalent. Each binding domain may comprise no more than one VH and one VL.

The term "bispecific" or "bispecific antibody" as employed herein refers to an antibody with two antigen specificities.

The term "complementarity determining regions" or "CDRs" refers to generally, antibodies comprise six CDRs: three in the VH (H1, H2, H3), and three in the VL (L1, L2, L3). The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise "CDR-H1" as employed herein is intended to refer to residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system. Unless indicated otherwise, CDR residues and other residues in the variable domain (e.g., FR residues) are numbered herein according to Kabat.

The term "chimeric" antibody refers to an antibody in which the variable domain (or at least a portion thereof) of the heavy and/or light chain is derived from a particular source or species, while the remainder of the heavy and/or light chain (i.e. the constant domains) is derived from a different source or species. (Morrison; PNAS 81, 6851 (1984)). Chimeric antibodies can for instance comprise non-human variable domains and human constant domains. Chimeric antibodies are typically produced using recombinant DNA methods. A subcategory of "chimeric antibodies" is "humanized antibodies".

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "complement-dependent cytotoxicity", or "CDC" refers to a mechanism for inducing cell death in which an Fc effector domain of a target-bound antibody binds and activates complement component C1q which in turn activates the complement cascade leading to target cell death.

The terms "constant domain(s)" or "constant region", as used herein are used interchangeably to refer to the domain(s) of an antibody which is outside the variable regions. The constant domains are identical in all antibodies of the same isotype but are different from one isotype to another. Typically, the constant region of a heavy chain is formed, from N to C terminal, by CH1-hinge —CH2-CH3-optionally CH4, comprising three or four constant domains.

The term "competing antibody" or "cross-competing antibody" shall be interpreted as meaning that the claimed antibody binds to either (i) the same position on the antigen to which the reference antibody binds, or (ii) a position on the antigen where the antibody sterically hinders the binding of the reference antibody to the antigen.

The term "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The term "derived from" in the context of generating variable sequences refers to the fact that the sequence employed or a sequence highly similar to the sequence employed was obtained from the original genetic material, such as the light or heavy chain of an antibody.

The term "diabody" as employed herein refers to two Fv pairs, a first VH/VL pair and a further VH/VL pair which have two inter-Fv linkers, such that the VH of a first Fv is linked to the VL of the second Fv and the VL of the first Fv is linked to the VH of the second Fv.

The term "DiFab" as employed herein refers to two Fab molecules linked via their C-terminus of the heavy chains.

The term "DiFab'" as employed herein refers to two Fab' molecules linked via one or more disulfide bonds in the hinge region thereof.

The term "dsscFv" or "disulphide-stabilised single chain variable fragment" as employed herein refer to a single chain variable fragment which is stabilised by a peptide linker between the VH and VL variable domain and also includes an inter-domain disulphide bond between VH and VL. (see for example, Weatherill et al., Protein Engineering, Design & Selection, 25 (321-329), 2012, WO2007109254.

The term "DVD-Ig" (also known as dual V domain IgG) refers to a full-length antibody with 4 additional variable domains, one on the N-terminus of each heavy and each light chain.

The term "effector functions" refer to those biological activities attributable to the Fc region of an antibody, which vary with the antibody isotype. Examples of antibody effector functions include: Clq binding and complement dependent cytotoxicity (CDC), Fc receptor binding, antibody-dependent cell-mediated cytotoxicity (ADCC), phagocytosis, down regulation of cell surface receptors (e.g. B cell receptor), and B cell activation.

The term "effector molecule" as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

The term "epitope" or "binding site" in the context of antibodies refer to a site (or a part) on an antigen to which the paratope of an antibody binds or recognizes. Epitopes can be formed both from contiguous amino acids (also often called "linear epitopes") or noncontiguous amino acids formed by tertiary folding of a protein (often called "conformational epitopes"). Epitopes formed from contiguous amino acids are typically retained on exposure to denaturing solvents whereas epitopes formed by folding are typically lost on treatment with denaturing solvents. An epitope typically includes at least 3, and more usually, at least 5-10 amino acids in a unique spatial conformation. Epitopes usually consist of chemically active surface groups of molecules such as amino acids, sugar side chains and usually have specific 3D structural and charge characteristics.

The "EU index" or "EU index as in Kabat" or "EU numbering scheme" refers to the numbering of the EU antibody (Edelman et al., 1969, Proc Natl Acad Sci USA 63:78-85). Such is generally used when referring to a residue in an antibody heavy chain constant region (e.g., as reported in Kabat et al.). Unless stated otherwise, the EU numbering scheme is used to refer to residues in antibody heavy chain constant regions described herein.

The term "Fab" refers to as used herein refers to an antibody fragment comprising a light chain fragment comprising a VL (variable light) domain and a constant domain of a light chain (CL), and a VH (variable heavy) domain and a first constant domain (CH1) of a heavy chain. Dimers of a Fab' according to the present disclosure create a F(ab')2 where, for example, dimerization may be through the hinge.

The term "Fab'-Fv" as employed herein is similar to FabFv, wherein the Fab portion is replaced by a Fab'. The format may be provided as a PEGylated version thereof.

The term "Fab'-scFv" as employed herein is a Fab' molecule with a scFv appended on the C-terminal of the light or heavy chain.

The term "Fab-dsFv" as employed herein refers to a FabFv wherein an intra-Fv disulfide bond stabilises the appended C-terminal variable regions. The format may be provided as a PEGylated version thereof.

The term "Fab-Fv" as employed herein refers to a Fab fragment with a variable region appended to the C-terminal of each of the following, the CH1 of the heavy chain and CL of the light chain. The format may be provided as a PEGylated version thereof.

The term "Fab-scFv" as employed herein is a Fab molecule with a scFv appended on the C-terminal of the light or heavy chain.

The term "Fc", "Fc fragment", and "Fc region" are used interchangeably to refer to the C-terminal region of an antibody comprising the constant region of an antibody excluding the first constant region immunoglobulin domain. Thus, Fc refers to the last two constant domains, CH2 and CH3, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index. In the context of human IgG1, the lower hinge refers to positions 226-236, the CH2 domain refers to positions 237-340 and the CH3 domain refers to positions 341-447 according to the EU index. The corresponding Fc region of other immunoglobulins can be identified by sequence alignments.

The term "Framework" or "FR" refers to variable domain residues other than hypervariable region residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" used herein to refer to an antibody having a structure substantially similar to a native antibody structure or having heavy chains that contain an Fc region as defined herein. Each light chain is comprised of a light chain variable region (abbreviated herein as VL) and a light chain constant region (CL). Each heavy chain is comprised of a heavy variable region (abbreviated herein as VH) and a heavy chain constant region (CH) constituted of three constant domains CH1, CH2 and CH3, or four constant domains CH1, CH2, CH3 and CH4, depending on the Ig class. The constant regions of the antibodies may mediate the binding of the immunoglobulin to host tissues or factors, including various cells of the immune system (e.g., effector cells) and the first component (Clq) of the classical complement system.

The term "Fv" refers to two variable domains of full length antibodies, for example co-operative variable domains, such as a cognate pair or affinity matured variable domains, i.e. a VH and VL pair.

The term "highly similar" as employed in the context of amino-acid sequences is intended to refer to an amino acid sequence which over its full length is 95% similar or more, such as 96, 97, 98 or 99% similar.

The term "human antibody" refers to an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In some embodiments, for the VL, the subgroup is subgroup kappa I as in Kabat et al., supra. In some embodiments, for the VH, the subgroup is subgroup III as in Kabat et al. In some embodiments, for the VH, the subgroup is subgroup IV as in Kabat et al.

The term "humanized" antibody refers to an antibody comprising amino acid residues from non-human HVRs and amino acid residues from human FRs. Typically the heavy and/or light chain contains one or more CDRs (including, if desired, one or more modified CDRs) from a donor antibody (e.g. a non-human antibody such as a murine or rabbit monoclonal antibody) and is grafted into a heavy and/or light chain variable region framework of an acceptor antibody (a human antibody) (see e.g. Vaughan et al, Nature Biotechnology, 16, 535-539, 1998). The advantage of such humanized antibodies is to reduce immunogenicity to humans, while retaining the specificity and affinity of the parental non-human antibody. Rather than the entire CDR being transferred, only one or more of the specificity determining residues from any one of the CDRs described herein above can be transferred to the human antibody framework (see e.g., Kashmiri et al., 2005, Methods, 36, 25-34). A "humanized" antibody refers to a chimeric antibody comprising amino acid residues from non-human HVRs and amino acid residues from human FRs. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts").

The term "IC50" as used herein refers to the half maximal inhibitory concentration which is a measure of the effectiveness of a substance, such as an antibody, in inhibiting a specific biological or biochemical function. The IC50 is a quantitative measure which indicates how much of a particular substance is needed to inhibit a given biological process by 50%.

The "identity" between amino-acids in the sequence indicates that at any particular position in the aligned sequences, the amino acid residue is identical between the sequences.

The term "IgG-scFv" as employed herein is a full-length antibody with a scFv on the C-terminal of each of the heavy chains or each of the light chains.

The term "IgG-V" as employed herein is a full-length antibody with a variable domain on the C-terminal of each of the heavy chains or each of the light chains The term "isolated" means, throughout this specification, that the antibody, or polynucleotide, as the case may be, exists in a physical milieu distinct from that in which it may occur in nature. The term "isolated" nucleic acid refers to a nucleic acid molecule that has been isolated from its natural environment or that has been synthetically created. An isolated nucleic acid may comprise synthetic DNA, for instance produced by chemical processing, cDNA, genomic DNA or any combination thereof.

The term "Kabat residue designations" or "Kabat" refer to the residue numbering scheme commonly used for antibodies. Such do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. For details see Kabat et al., Sequences of Proteins of Immunological Interest, 5th Ed. Public Health Service, National Institutes of Health, Bethesda, MD (1991). Unless indicated otherwise, Kabat numbering is used throughout the specification The term "KD" as used herein refers to the constant of dissociation which is obtained from the ratio of Kd to Ka (i.e. Kd/Ka) and is expressed as a molar concentration (M). Kd and Ka refers to the dissociation rate and association rate, respectively, of a particular antigen-antibody interaction. KD values for antibodies can be determined using methods well established in the art.

The term "monoclonal antibody" (or "mAb") refers to an antibody obtained from a population of substantially homogeneous antibodies, i.e. each individual of a monoclonal antibody preparation are identical except for possible mutations (e.g., naturally occurring mutations), that may be present in minor amounts. Certain differences in the protein sequences linked to post-translational modifications (for example, cleavage of the heavy chain C-terminal lysine, deamidation of asparagine residues and/or isomerisation of aspartate residues) may nevertheless exist between the various different antibody molecules present in the composition. Contrary to polyclonal antibody preparations, each monoclonal antibody of a monoclonal antibody preparation is directed against a single determinant on an antigen.

The term "multi-paratopic antibody" as employed herein refers to an antibody as described herein which comprises two or more distinct paratopes, which interact with different epitopes either from the same antigen or from two different antigens. Multi-paratopic antibodies described herein may be biparatopic, triparatopic, tetraparatopic.

The term "multispecific" or "multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen. Multi-specific antibodies are generally monovalent for each specificity (antigen). Multi-specific antibodies described herein encompass monovalent and multivalent, e.g. bivalent, trivalent, tetravalent multi-specific antibodies.

The term "neutralizing" (or "neutralize") in the context of antibodies describes an antibody that is capable of inhibiting or attenuating the biological signaling activity of its target (target protein).

The term "paratope" refers to a region of an antibody which recognizes and binds to an antigen.

The term "percent (%) sequence identity (or similarity)" with respect to the polypeptide and antibody sequences is defined as the percentage of amino acid residues in a candidate sequence that are identical (or similar) to the amino acid residues in the polypeptide being compared, after aligning the sequences and introducing gaps, if necessary, to achieve the maximum percent sequence identity, and not considering any conservative substitutions as part of the sequence identity A "pharmaceutically acceptable carrier" refers to an ingredient in a pharmaceutical formulation, other than an active ingredient, which is nontoxic to a subject. Pharmaceutically acceptable carriers include, but are not limited to, a buffer, excipient, stabilizer, or preservative.

The term "polyclonal antibody" refers to a mixture of different antibody molecules which bind to (or otherwise interact with) more than one epitope of an antigen The term "prevent" in the context of antibodies is used herein interchangeably with the term "inhibit" and indicates the effect the antibodies according to the present invention have with respect to a particular biological process or molecular interaction.

The term "scDiabody" refers to a diabody comprising an intra-Fv linker, such that the molecule comprises three linkers and forms a normal scFv whose VH and VL terminals are each linked to a one of the variable regions of a further Fv pair.

The term "Scdiabody-CH3" as employed herein refers to two scdiabody molecules each linked, for example via a hinge to a CH3 domain.

The term "ScDiabody-Fc" as employed herein is two scdiabodies, wherein each one is appended to the N-terminus of a CH2 domain, for example via a hinge, of constant region fragment —CH2CH3.

The term "single chain variable fragment" or "scFv" as employed herein refers to a single chain variable fragment which is stabilised by a peptide linker between the VH and VL variable domains.

The term "ScFv-Fc-scFv" as employed herein refers to four scFvs, wherein one of each is appended to the N-terminus and the C-terminus of both the heavy chains of a CH2CH3 fragment.

The term "scFv-IgG" as employed herein is a full-length antibody with a scFv on the N-terminal of each of the heavy chains or each of the light chains.

The term "similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

The term "single domain antibody" as used herein refers to an antibody fragment consisting of a single monomeric variable domain. Examples of single domain antibodies include VH or VL or VHH or V-NAR.

The term "specific" as employed herein in the context of antibodies is intended to refer to an antibody that only recognizes the antigen to which it is specific or an antibody that has significantly higher binding affinity to the antigen to which it is specific compared to binding to antigens to which it is non-specific, for example at least 5, 6, 7, 8, 9, 10 times higher binding affinity.

The term "sterically blocking" or "sterically preventing" as employed herein is intended to refer to the means of blocking an interaction between first and second proteins by a third protein's binding to the first protein. The binding between the first and the third proteins prevents the second protein from binding to the first protein due to unfavorable van der Waals or electrostatic interactions between the second and third proteins.

The terms "subject" or "individual" in the context of the treatments and diagnosis generally refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). More specifically, the individual or subject is a human The term "Tandem scFv" as employed herein refers to at least two scFvs linked via a single linker such that there is a single inter-Fv linker.

The term "Tandem scFv-Fc" as employed herein refers to at least two tandem scFvs, wherein each one is appended to the N-terminus of a CH2 domain, for example via a hinge, of constant region fragment —CH2CH3.

The term "target" or "antibody target" as used herein refers to target antigen to which the antibody binds.

The term "Tetrabody" as employed herein refers to a format similar to the diabody comprising fours Fvs and four inter-Fv linkers.

The term "therapeutically effective amount" refers to the amount of an antibody thereof that, when administered to a subject for treating a disease, is sufficient to produce such treatment for the disease. The therapeutically effective amount will vary depending on the antibody, the disease and its severity and the age, weight, etc., of the subject to be treated.

The term "tribody" (also referred to a $Fab(scFv)_2$) as employed herein refers to a Fab fragment with a first scFv appended to the C-terminal of the light chain and a second scFv appended to the C-terminal of the heavy the chain.

The term "trispecific or trispecific antibody" as employed herein refers to an antibody with three antigen binding specificities. For example, the antibody is an antibody with three antigen binding domains (trivalent), which independently bind three different antigens or three different epitopes on the same antigen, i.e. each binding domain is monovalent for each antigen. One of the examples of a trispecific antibody format is TrYbe.

The terms "prevent", or "preventing" and the like, refer to obtaining a prophylactic effect in terms of completely or partially preventing a disease or symptom thereof. Preventing thus encompasses stopping the disease from occurring in a subject who may be predisposed to the disease but has not yet been diagnosed as having the disease.

The terms "treatment", "treating" and the like, refer to obtaining a desired pharmacologic and/or physiologic effect. The effect may be therapeutic in terms of a partial or complete cure for a disease and/or adverse effect attributable to the disease. Treatment thus encompasses (a) inhibiting the disease, i.e., arresting its development; and (b) relieving the disease, i.e., causing regression of the disease.

The term "TrYbe" as employed herein refers to a tribody comprising two dsscFvs. dsFab as employed herein refers to a Fab with an intra-variable region disulfide bond.

The term "variable region" or "variable domain" refers to the domain of an antibody heavy or light chain that is involved in binding the antibody to antigen. The variable domains of the heavy chain (VH) and light chain (VL) of a full length generally have similar structures, with each domain comprising four conserved framework regions (FRs) and three CDRs. (See, e.g., Kindt et al. Kuby Immunology, 6th ed., W.H. Freeman and Co., page 91 (2007).) A single VH or VL domain may be sufficient to confer antigen-binding specificity. Each VH and VL is composed of three CDRs and four FRs, arranged from amino-terminus to carboxy-terminus in the following order: FR1, CDR1, FR2, CDR2, FR3, CDR3, FR4. The CDRs and the FR together form a variable region. By convention, the CDRs in the heavy chain variable region of an antibody are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain. CDRs are conventionally numbered according to a system devised by Kabat.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." The term "vector" includes "expression vectors".

The term "VH" refers to the variable domain (or the sequence) of the heavy chain.

The term "V-IgG" as employed herein is a full-length antibody with a variable domain on the N-terminal of each of the heavy chains or each of the light chains.

The term "VL" refers to the variable domain (or the sequence) of the light chain.

Interleukin 22 (IL22)

The term "interleukin-22" or "IL22" refers to a class II cytokine capable of binding to IL22R1 (also known as IL22RA1, IL22 receptor 1, or Interleukin-22 receptor subunit alpha-1) and/or a receptor complex of IL22R1 and IL10RA2 (also known as IL22BP, IL22 binding protein, or Interleukin-22 Receptor Subunit Alpha 2). IL22 is also known as interleukin-10 related T cell-derived inducible factor (IL-TIF). The term refers to naturally occurring or endogenous mammalian IL22 proteins and to proteins having an amino acid sequence which is the same as that of a naturally occurring or endogenous corresponding mammalian IL22 protein (e.g., recombinant proteins, synthetic proteins). Accordingly, as defined herein, the term includes mature IL22 protein, polymorphic or allelic variants, and other isoforms of IL22 (e.g., produced by alternative splicing or other cellular processes), and modified or unmodified forms of the foregoing (e.g., Lipidated, glycosylated). Naturally occurring or endogenous IL22 include wild type proteins such as mature IL22, polymorphic or allelic variants and other isoforms and mutant forms which occur naturally in mammals (e.g., humans, non-human primates). These proteins and proteins having the same amino acid sequence as a naturally occurring or endogenous corresponding IL22 are referred to by the name of the corresponding mammal.

The amino acid sequence of mature human IL22 corresponds to amino acids 34-179 of SEQ ID NO:1. Analysis of recombinant human IL22 reveals many structural domains. (Nagem et al. (2002) Structure, 10:1051-62; US2002/0187512).

Antibodies Binding to IL22

The present invention provides anti-IL22 antibodies that bind to IL22 (target polypeptide) and have functional and structural properties as described further herein.

The present disclosure provides a method of identifying an antibody that binds to IL22, said method comprising:
a) immunizing an animal with human IL22;
b) isolating generated anti-IL22 antibodies from said animals; and
c) selecting anti-IL22 antibodies that:
  i. bind to both to human and cynomolgus monkey IL22;
  ii. neutralize IL22-induced STAT3 phosphorylation, or IL22-dependent IL-10 release; and
  iii. bind to human IL22 and prevent binding of IL22R1.

Any suitable animal might be used for generation of anti-IL22 antibodies, including mice, rats and rabbits. The binding to IL22 and cross-binding measurements might be performed using techniques know to the skilled person. Standard assays are available for the measurement of neutralizing activity of identified antibodies. Examples of such assays are provided in the Examples herein.

The antibodies in the context of the present invention include whole antibodies and functionally active antibody fragments (i.e., molecules that contain an antigen binding domain that specifically binds an antigen, also termed antigen-binding fragments). Features described herein also apply to antibody fragments unless context dictates otherwise. The antibody may be (or derived from) polyclonal, monoclonal, multi-valent, multi-specific, bispecific, fully human, humanized or chimeric.

The antibodies described further in for purposes of reference and example only and do not limit the scope of invention.

An antibody used according to the invention may be a monoclonal antibody or a polyclonal antibody, and is preferably a monoclonal antibody. An antibody used according to the invention may be a chimeric antibody, a CDR-grafted antibody (e.g., any appropriate acceptor variable region framework sequence may be used having regard to the class/type of the donor antibody from which the CDRs are derived, including mouse, primate and human framework regions), a nanobody, a human or humanized antibody. For the production of both monoclonal and polyclonal antibodies, the animal used to raise such antibodies is typically a non-human mammal such as a goat, rabbit, rat or mouse but the antibody may also be raised in other species.

Polyclonal antibodies may be produced by routine methods such as immunization of a suitable animal with an antigen of interest. Blood may be subsequently removed from such animal and the produced antibodies purified.

Monoclonal antibodies may be made by a variety of techniques, including but not limited to, the hybridoma method, recombinant DNA methods, phage-display methods, and methods utilizing transgenic animals containing all or a part of the human immunoglobulin loci. Some exemplary methods for making monoclonal antibodies are described herein.

For example, monoclonal antibodies may be prepared using the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by for example the methods described in WO9202551, WO2004051268 and WO2004106377.

Antibodies generated against the target polypeptide may be obtained, where immunization of an animal is necessary, by administering the polypeptide to an animal, preferably a non-human animal, using well-known and routine protocols, see for example Handbook of Experimental Immunology, D. M. Weir (ed.), Vol 4, Blackwell Scientific Publishers, Oxford, England, 1986). Many animals, such as rabbits, mice, rats, sheep, cows, camels or pigs may be immunized. However, mice, rabbits, pigs and rats are generally used.

Monoclonal antibodies can also be generated using various. phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280). In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol, 227: 381-388 (1992). Patent publications describing human antibody phage libraries include, for example: U.S. Pat. No. 5,750,373, and US 2005/0079574, US2005/0119455, US2005/0266000, US2007/0117126, US2007/0160598, US2007/0237764, US2007/0292936, and US2009/0002360.

Screening for antibodies can be performed using assays to measure binding to the target polypeptide and/or assays to measure the ability of the antibody to block a particular interaction. An example of a binding assay is an ELISA, for example, using a fusion protein of the target polypeptide, which is immobilized on plates, and employing a conjugated secondary antibody to detect the antibody bound to the target. An example of a blocking assay is a flow cytometry based assay measuring the blocking of a ligand protein binding to the target polypeptide. A fluorescently labelled secondary antibody is used to detect the amount of such ligand protein binding to the target polypeptide.

Antibodies may be isolated by screening combinatorial libraries for antibodies with the desired activity or activities. For example, a variety of methods are known in the art for generating phage display libraries and screening such libraries for antibodies possessing the desired binding characteristics.

Antibodies or antibody fragments isolated from human antibody libraries are considered human antibodies or human antibody fragments.

The antibody may be a full length antibody. More particularly the antibody may be of the IgG isotype. More particularly the antibody may be an IgG1 or IgG4.

The constant region domains of the antibody, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. It will also be known to the person skilled in the art that antibodies may undergo a variety of posttranslational modifications. The type and extent of these modifications often depends on the host cell line used to express the antibody as well as the cell culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705:129-134, 1995). Accordingly, the C-terminal lysine of the antibody heavy chain may be absent.

Alternatively, the antibody is an antigen-binding fragment.

For a review of certain antigen-binding fragments, see Hudson et al. Nat. Med. 9: 129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. Fab and F(ab')2 fragments comprising salvage receptor binding epitope residues and having increased in vivo half-life are disclosed in U.S. Pat. No. 5,869,046.

Antigen-binding fragments and methods of producing them are well known in the art, see for example Verma et al., 1998, Journal of Immunological Methods, 216, 165-181; Adair and Lawson, 2005. Therapeutic antibodies. Drug Design Reviews—Online 2(3):209-217. The Fab-Fv format was first disclosed in WO2009/040562 and the disulphide stabilized version thereof, the Fab-dsFv, was first disclosed in WO2010/035012, and TrYbe format is disclosed in WO2015/197772.

Various techniques have been developed for the production of antibody fragments. Such fragments might be derived via proteolytic digestion of intact antibodies (see, e.g., Morimoto et al., Journal of Biochemical and Biophysical Methods 24: 107-117 (1992) and Brennan et al, Science 229:81 (1985)). However, antibody fragments can also be produced directly by recombinant host cells. For example, antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)).

F(ab')$_2$ fragments can be isolated directly from recombinant host cell culture. The antibody may be a single chain Fv fragment (scFv). Such are described in WO 93/16185; U.S. Pat. Nos. 5,571,894; and 5,587,458. The antibody fragment may also be a "linear antibody," e.g., as described in U.S. Pat. No. 5,641,870. Such linear antibody fragments may be monospecific or bispecific.

The antibody may be a Fab, Fab', F(ab')$_2$, Fv, dsFv, scFv, or dsscFv. The antibody may be a single domain antibody or a nanobody, for example VH or VL or VHH or VNAR. The antibody may be Fab or Fab' fragment described in WO2011/117648, WO2005/003169, WO2005/003170 and WO2005/003171.

The antibody may be a Disulphide—stabilized single chain variable fragment (dsscFv).

The disulfide bond between the variable domains VH and VL may be between two of the residues listed below:

V$_H$37+V$_L$95 see for example Protein Science 6, 781-788 Zhu et a/(1997);

V$_H$44+V$_L$100 see for example Weatherill et al., Protein Engineering, Design & Selection, 25 (321-329), 2012;

V$_H$44+V$_L$105 see for example J Biochem. 118, 825-831 Luo et a/(1995);

V$_H$45+V$_L$87 see for example Protein Science 6, 781-788 Zhu et a/(1997);

V$_H$55+V$_L$101 see for example FEBS Letters 377 135-139 Young et a/(1995);

V$_H$100+V$_L$50 see for example Biochemistry 29 1362-1367 Glockshuber et a/(1990);

V$_H$1 00b+V$_L$49; see for example Biochemistry 29 1362-1367 Glockshuber et a/(1990);

V$_H$98+V$_L$46 see for example Protein Science 6, 781-788 Zhu et a/(1997);

V$_H$101+V$_L$46; see for example Protein Science 6, 781-788 Zhu et a/(1997);

V$_H$105+V$_L$43 see for example; Proc. Natl. Acad. Sci. USA Vol. 90 pp. 7538-7542 Brinkmann et al (1993); or Proteins 19, 35-47 Jung et al (1994), V$_H$106+V$_L$57 see for example FEBS Letters 377 135-139 Young et a/(1995) and a position or positions corresponding thereto in a variable region pair located in the molecule.

The disulphide bond may be formed between positions VH44 and VL100.

It will be appreciated by the skilled person that antigen-binding fragments described herein may also be characterized as monoclonal, chimeric, humanized, fully human, multispecific, bispecific etc., and that discussion of these terms also relate to such fragments.

Multi-Specific Antibodies

The antibodies of the present invention may be multispecific antibodies.

Examples of multi-specific antibodies or antigen-binding fragments thereof, which also are contemplated for use in the context of the disclosure, include bi, tri or tetra-valent antibodies, Bis-scFv, diabodies, triabodies, tetrabodies, bibodies and tribodies (see for example Holliger and Hudson, 2005, Nature Biotech 23(9): 1126-1136; Schoonjans et al. 2001, Biomolecular Engineering, 17(6), 193-202).

A variety of multi-specific antibody formats have been generated. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Alternative molecular formats and therapeutic applications for bispecific antibodies. Mol Immunol. 67(2015):95-106.

The antibody may be a bi-specific antibody. In one embodiment, the antibody comprises two antigen binding domains wherein one binding domain binds IL22 and the other binding domain binds another antigen, i.e. each binding domain is monovalent for each antigen. In one embodiment, the antibody is a tetravalent bispecific antibody, i.e. the antibody comprises four antigen binding domains, wherein for example two binding domains bind IL22 and the other two binding domains bind to another antigen. In one embodiment, the antibody is a trivalent bispecific antibody.

Techniques for making bispecific antibodies include, but are not limited to, CrossMab technology (Klein et al. Engineering therapeutic bispecific antibodies using CrossMab technology, Methods 154 (2019) 21-31), Knobs-in-holes engineering (e.g. WO1996027011, WO1998050431), Duo-Body technology (e.g. WO2011131746), Azymetric technology (e.g. WO2012058768). Further technologies for making bispecific antibodies have been described for example in Godar et al., 2018, Therapeutic bispecific antibody formats: a patent applications review (1994-2017), Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, ia-body and orthogonal Fab.

The antibody construct may be a tri-specific antibody.

The antibody may be a multi-paratopic antibody.

In one embodiment, each binding domain is monovalent. Preferably each binding domain comprises no more than one VH and one VL.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. VH or VL), Fv, scFv, dsscFv, Fab, scFab Appended IgG antibody formats include in particular DVD-IgG, IgG (H)-scFv, scFv-(H)IgG, IgG(L)-scFv, scFv-(L)IgG, IgG(L, H)-Fv, IgG(H)-V, V(H)-IgG, IgC(L)-V, V(L)-IgG, KIH IgG-scFab, 2scFv-IgG, IgG-2scFv, scFv4-Ig, Zybody and DVI-IgG (four-in-one), for example as described in Spiess et al., Alternative molecular formats and therapeutic applications for bispecific antibodies. Mol Immunol. 67(2015):95-106.

Multispecific antibody fragments include nanobody, nanobody-HSA, BiTEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, F(ab)$_2$, F(ab')$_2$-scFv2, scFv-KIH, Fab-scFv-Fc, Tetravalent HCAb, scDiabody-Fc, Diabody-Fc, Tandem scFv-Fc; and intrabody, as described, for example, Spiess et al., Alternative molecular formats and therapeutic applications for bispecific antibodies. Mol Immunol. 67(2015):95-106.

Multispecific fusion proteins include Dock and Lock, ImmTAC, HSAbody, scDiabody-HSA, and Tandem scFv-Toxin.

Multispecific antibody conjugates include IgG-IgG; Cov-X-Body; and scFv1-PEG-scFv2.

Additional multispecific antibody formats have been described for example in Brinkmann et al, The making of bispecific antibodies, mAbs, 9:2, 182-212 (2017), in particular in FIG. 2, for example tandem scFv, triplebody, Fab-VEIH, taFv-Fc, scFv4-Ig, scFv2-Fcab, scFv4-IgG. Bibodies, tribodies and methods for producing such are disclosed, for example, in WO99/37791.

The antibody for use in the present invention may be a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in WO2015/197772. Another preferred antibody for use in the present invention fragment comprises a Fab linked to only one scFv or dsscFv, as described for example in WO2013/068571, and Dave et al., Mabs, 8(7) 1319-1335 (2016).

Another antibody for use in the present invention is a Knobs-into-holes antibody ("KiH"). It is a multi-specific antibody format consisting of heavy chain homodimers for heterodimerization (e.g., for the efficient production of bispecific antibodies, multi-specific antibodies, or one-armed antibodies). Generally, such technology involves introducing a protuberance ("knob") at the interface of a first polypeptide (such as a first CH3 domain in a first antibody heavy chain) and a corresponding cavity ("hole") in the interface of a second polypeptide (such as a second CH3 domain in a second antibody heavy chain), such that the protuberance can be positioned in the cavity so as to promote heterodimer formation and hinder homodimer formation. Protuberances are constructed by replacing small amino acid side chains from the interface of the first polypeptide (such as a first CH3 domain in a first antibody heavy chain) with larger side chains (e.g. arginine, phenylalanine, tyrosine or tryptophan). Compensatory cavities of identical or similar size to the protuberances are created in the interface of the second polypeptide (such as a second CH3 domain in a second antibody heavy chain) by replacing large amino acid side chains with smaller ones (e.g. alanine, serine, valine, or threonine). The protuberance and cavity can be made by altering the nucleic acid encoding the polypeptides, e.g. by site-specific mutagenesis, or by peptide synthesis. Further details regarding "knobs-into-holes" technology is described in, e.g., U.S. Pat. Nos. 5,731,168; 7,695,936; WO 2009/089004; US 2009/0182127; Marvin and Z u, Acta Pharmacologica Sincia (2005) 26(6):649-658; Kontermann Acta Pharmacologica Sincia (2005) 26: 1-9; Ridgway et al, Prot Eng 9, 617-621 (1996); and Carter, J Immunol Meth 248, 7-15 (2001).

Humanized, Human, and Chimeric Antibodies and Methods of Producing Such

The antibodies of the present invention may be, but are not limited to, humanized, fully human or chimeric antibodies.

In one embodiment the antibody is humanized. More particularly the antibody is a chimeric, human, or humanized antibody.

In certain embodiments, an antibody provided herein is a chimeric antibody. Examples of chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In one embodiment, the antibody is a humanized antibody.

Humanized antibodies may optionally further comprise one or more framework residues derived from the non-human species from which the CDRs were derived. It will be appreciated that it may only be necessary to transfer the specificity determining residues of the CDRs rather than the entire CDR (see for example, Kashmiri et al., 2005, Methods, 36, 25-34).

Suitably, the humanized antibody according to the present invention has a variable domain comprising human acceptor framework regions as well as one or more of the CDRs and optionally further including one or more donor framework residues.

Thus, provided in one embodiment is a humanized antibody wherein the variable domain comprises human acceptor framework regions and non-human donor CDRs.

When the CDRs or specificity determining residues are grafted, any appropriate acceptor variable region framework sequence may be used having regard to the class/type of the donor antibody from which the CDRs are derived, including mouse, primate and human framework regions.

Examples of human frameworks which can be used in the present invention are KOL, NEWM, REI, EU, TUR, TEI, LAY and POM (Kabat et al). For example, KOL and NEWM can be used for the heavy chain, REI can be used for the light chain and EU, LAY and POM can be used for both the heavy chain and the light chain. Alternatively, human germline sequences may be used; these are available at: www.imgt.org. In embodiments, the acceptor framework is IGKV1D-13 human germline, IGHV3-66 human germline, IGKV1-12 human germline, and/or IGHV4-31 human germline. In embodiments, the human framework contains 1-5, 1-4, 1-3 or 1-2 donor antibody amino acid residues.

In a humanized antibody of the present invention, the acceptor heavy and light chains do not necessarily need to be derived from the same antibody and may, if desired, comprise composite chains having framework regions derived from different chains.

In certain embodiments, an antibody provided herein is a human antibody. Human antibodies can be produced using various techniques known in the art.

Human antibodies comprise heavy or light chain variable regions or full length heavy or light chains that are "the product of" or "derived from" a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene.

In certain cases, the human antibody may display no more than 5, or even no more than 4, 3, 2, or 1 amino acid difference from the amino acid sequence encoded by the germline immunoglobulin gene.

Structural Features of the Antibodies

The antibody of the invention comprises a binding domain. A binding domain will generally comprise 6 CDRs, three from a heavy chain and three from a light chain. In one embodiment the CDRs are in a framework and together form a variable region. Thus, the antibody has a binding domain specific for antigen, said binding domain comprising a light chain variable region and a heavy chain variable region.

TABLE 3

Amino-acid sequences of the anti-IL22 antibodies

| Feature | 11041 SEQ ID NO | 11070 SEQ ID NO |
|---|---|---|
| CDR-L1 | 5 | 65 |
| CDR-L2 | 6 | 66 |
| CDR-L3 | 7 | 67 |
| CDR-H1 | 8 | 68 |
| CDR-H2 | 9 | 69 |
| CDR-H3 | 10 | 70 |
| Light chain V region | 22 | 72 |
| Heavy chain V region | 24 | 74 |
| Light chain | 26 | 76 |
| Heavy chain Fab | 28 | 78 |
| Heavy chain IgG1 | 30 | 80 |
| Heavy chain IgG4P | 32 | 82 |

In one embodiment the present invention provides an antibody that binds to IL22, comprising a light chain variable domain which comprises at least one of:
a CDR-L1 comprising SEQ ID NO:5,
a CDR-L2 comprising SEQ ID NO:6, and
a CDR-L3 comprising SEQ ID NO:7.

In one embodiment the present invention provides an antibody that binds to IL22, comprising a light chain variable domain which comprises
a CDR-L1 comprising SEQ ID NO:5,
a CDR-L2 comprising SEQ ID NO:6, and
a CDR-L3 comprising SEQ ID NO:7.

In one embodiment the present invention provides an antibody that binds to IL22, comprising a heavy chain variable domain which comprises at least one of:
a CDR-H1 comprising SEQ ID NO:8,
a CDR-H2 comprising SEQ ID NO:9, and
a CDR-H3 comprising SEQ ID NO:10.

In one embodiment the present invention provides an antibody that binds to IL22, comprising a heavy chain variable domain which comprises
a CDR-H1 comprising SEQ ID NO:8,
a CDR-H2 comprising SEQ ID NO:9, and
a CDR-H3 comprising SEQ ID NO:10.

The antibody molecules of the present invention may comprise a complementary light chain or a complementary heavy chain, respectively.

Hence, in one embodiment the present invention provides an antibody that binds to IL22, comprising:
a light chain variable region comprising:
a CDR-L1 comprising SEQ ID NO:5,
a CDR-L2 comprising SEQ ID NO:6, and
a CDR-L3 comprising SEQ ID NO:7;
and a heavy chain variable region comprising:
a CDR-H1 comprising SEQ ID NO:8,
a CDR-H2 comprising SEQ ID NO:9, and
a CDR-H3 comprising SEQ ID NO:10.

In one embodiment, an antibody of the present invention comprises a light chain variable region comprising the sequence given in SEQ ID NO:22 or SEQ ID NO:72.

In one embodiment, an antibody of the present invention comprises a heavy chain variable region comprising the sequence given in SEQ ID NO:24 or SEQ ID NO:74.

In one embodiment, an antibody of the present invention comprises a light chain variable region comprising the sequence given in SEQ ID NO:22 and a heavy chain variable region comprising the sequence given in SEQ ID NO:24.

In an alternative embodiment, an antibody of the present invention comprises a light chain variable region comprising the sequence given in SEQ ID NO:72 and a heavy chain variable region comprising the sequence given in SEQ ID NO:74.

In one embodiment, an antibody of the present invention is a Fab comprising
a light chain variable region comprising:
a CDR-L1 comprising SEQ ID NO:5,
a CDR-L2 comprising SEQ ID NO:6, and
a CDR-L3 comprising SEQ ID NO:7;
and a heavy chain variable region comprising:
a CDR-H1 comprising SEQ ID NO:8,
a CDR-H2 comprising SEQ ID NO:9, and
a CDR-H3 comprising SEQ ID NO:10.

In one embodiment the antibody of the present invention is a Fab comprising a light chain comprising the sequence given in SEQ ID NO:26 and a heavy chain comprising the sequence given in SEQ ID NO:28.

In another embodiment, the antibody of the present invention is a IgG1 comprising a light chain comprising the sequence given in SEQ ID NO: 26 and a heavy chain comprising the sequence given in SEQ ID NO: 30.

In another embodiment, the antibody of the present invention is a IgG4P comprising a light chain comprising the sequence given in SEQ ID NO: 26 and a heavy chain comprising the sequence given in SEQ ID NO: 32.

In an alternative embodiment the present invention provides an antibody that binds to IL22, comprising a light chain variable domain which comprises at least one of:
a CDR-L1 comprising SEQ ID NO:65,
a CDR-L2 comprising SEQ ID NO:66, and
a CDR-L3 comprising SEQ ID NO:67.

In in alternative embodiment the present invention provides an antibody that binds to IL22, comprising a light chain variable domain which comprise
a CDR-L1 comprising SEQ ID NO:65,
a CDR-L2 comprising SEQ ID NO:66, and
a CDR-L3 comprising SEQ ID NO:67

In an alternative embodiment the present invention provides an antibody that binds to IL22, comprising a heavy chain variable domain which comprises at least one of:

a CDR-H1 comprising SEQ ID NO:68,
a CDR-H2 comprising SEQ ID NO:69, and
a CDR-H3 comprising SEQ ID NO:70.

In an alternative embodiment the present invention provides antibody that binds to IL22, comprising a heavy chain variable domain which comprises a CDR-H1 comprising SEQ ID NO:68,
a CDR-H2 comprising SEQ ID NO:69, and
a CDR-H3 comprising SEQ ID NO:70.

In an alternative embodiment the present invention provides antibody that binds to IL22, comprising:

a light chain variable region comprising:
    a CDR-L1 comprising SEQ ID NO:65,
    a CDR-L2 comprising SEQ ID NO:66, and
    a CDR-L3 comprising SEQ ID NO:67;
and a heavy chain variable region comprising:
    a CDR-H1 comprising SEQ ID NO:68,
    a CDR-H2 comprising SEQ ID NO:69, and
    a CDR-H3 comprising SEQ ID NO:70.

In an alternative embodiment, an antibody of the present invention is a Fab comprising a light chain variable region comprising:
    a CDR-L1 comprising SEQ ID NO:65,
    a CDR-L2 comprising SEQ ID NO:66, and
    a CDR-L3 comprising SEQ ID NO:67;
and a heavy chain variable region comprising:
    a CDR-H1 comprising SEQ ID NO:68,
    a CDR-H2 comprising SEQ ID NO:69, and
    a CDR-H3 comprising SEQ ID NO:70.

In yet another alternative embodiment the antibody of the present invention is a Fab comprising a light chain comprising the sequence given in SEQ ID NO:76 and a heavy chain comprising the sequence given in SEQ ID NO:78.

In another alternative embodiment, the antibody of the present invention is a IgG1 comprising a light chain comprising the sequence given in SEQ ID NO: 76 and a heavy chain comprising the sequence given in SEQ ID NO: 80.

In another alternative embodiment, the antibody of the present invention is a IgG4P comprising a light chain comprising the sequence given in SEQ ID NO:76 and a heavy chain comprising the sequence given in SEQ ID NO:82.

In embodiments, the invention provides an antibody comprising a light chain variable region comprising a CDR-L1 comprising SEQ ID NO:5 or SEQ ID NO:65, a CDR-L2 comprising SEQ ID NO:6 or SEQ ID NO:66, a CDR-L3 comprising SEQ ID NO:7 or SEQ ID NO:67; and a heavy chain variable region comprising a CDR-H1 comprising SEQ ID NO:8 or SEQ ID NO:68, CDR-H2 comprising SEQ ID NO:9 or SEQ ID NO:69, and a CDR-H3 comprising SEQ ID NO:10 or SEQ ID NO:70.

In one embodiment, the antibody comprises a heavy chain and a light chain wherein the heavy chain comprises a CH1 domain and the light chain comprises a CL domain, either kappa or lambda.

Functional Properties of the Anti-IL22 Antibodies

In one embodiment, the antibody of the present invention is a neutralizing antibody. Preferably the antibody according to the present invention is neutralizing IL22 activity. In particular, the antibody is capable of neutralizing IL22 binding to IL22 receptor 1 (IL22R1). An anti-IL22 antibody of the present invention also binds to IL22 and inhibits IL22 binding to IL22 binding protein (IL22RA2 or IL22BP).

Preferably, the antibody is capable of neutralizing IL22 binding to IL22 receptor 1 (IL22R1) and IL22 binding protein (L22RA2).

The anti-IL22 antibodies of the present invention bind to the same region on IL22 as IL22R1. In one particular embodiment, the present invention provides an antibody that binds to a region on IL22 such that the binding sterically blocks the interaction between IL22 and IL22R1. In particular, the variable region of the antibody may sterically block the interaction between IL22 and IL22R1.

In some embodiments, the antibody according to the present invention binds to IL22 that is not bound to IL22BP ("free IL22"). In some embodiments, the antibody according to the present invention binds to IL22 and prevents IL22 from binding to IL22BP.

An antibody according to the present invention is specific for IL22. In one embodiment, the antibody has a stronger binding affinity for IL22 compared to IL22R1. This is characterized by a dissociation affinity constant (KD) at least 10-fold higher for IL22 than for IL22R1 or IL22BP. Specifically such is measured using BIACore technique.

In some embodiments, the antibody binds to IL22 with sufficient affinity and specificity. In certain embodiments, the antibody binds human IL22 with a KD of about any one of 1 µM, 100 nM, 50 nM, 40 nM, 30 nM, 20 nM, 10 nM, 5 nM, 1 nM, 0.5 nM, 0.1 nM, 0.05 nM, or 0.001 nM (e.g. 10-8 M or less, e.g. from 10-8 M to 10-13 M, e.g., from 10-9 M to 10-13 M), including any range in between these values. In one embodiment, the antibody according to the present invention binds human IL22 with a KD of less than 100 pM.

In certain embodiments, the antibody binds cynomolgus IL22 with a $K_D$ of about any one of 1 µM, 100 nM, 50 nM, 40 nM, 30 nM, 20 nM, 10 nM, 5 nM, 1 nM, 0.5 nM, 0.1 nM, 0.05 nM, or 0.001 nM (e.g. 10-8 M or less, e.g. from 10-8 M to 10-13 M, e.g., from 10-9 M to 10-13 M), including any range in between these values. In one embodiment, the antibody according to the present invention binds cynomolgus IL22 with a KD of less than 100 pM.

It will be appreciated by the skilled person that KD value may differ depending on the format and overall structure of the antibody. For example, the KD of an antibody might differ in the context of the multi-specific antibodies, full length antibodies, or antibody fragments.

An anti-IL22 antibody of the present invention is capable of inhibiting IL22-induced IL10 release from cells.

As demonstrated by the Examples, the anti-IL22 antibodies of the invention are capable of inhibiting IL22-mediated keratinocyte proliferation and differentiation.

The anti-IL22 antibodies of the invention are also capable of inhibiting the release of IL22-induced antimicrobial peptides, such as, for example, S100A7.

The affinity of an antibody, as well as the extent to which an antibody inhibits binding, can be determined by the skilled person using conventional techniques, for example those described by Scatchard et al. (Ann. KY. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In one embodiment, an anti-IL22 antibody according to the present invention binds to IL22 that is not bound to IL22 binding protein ("free IL22"). More specifically, an antibody according to the present invention binds to IL22 and prevents IL22 from binding to IL22 binding protein.

Preferably the antibody according to the present invention is specific for IL22.

Disclosure herein relating to antibodies, particularly with respect to binding affinity and specificity, and activity, also is applicable to antigen-binding fragments and antibody-like molecules.

Antibodies Binding to the Same Epitope

Antibodies may compete for binding to IL22 with, or bind to the same epitope as, those defined above in terms of light-chain, heavy-chain, light chain variable region (LCVR), heavy chain variable region (HCVR) or CDR sequences.

In particular, the present invention provides an antibody that competes for binding to IL22 with, or bind to the same epitope as, an antibody which comprises a CDR-L1/CDR-L2/CDR-L3/CDR-H1/CDR-H2/CDR-H3 sequence combination of SEQ ID NOs: 5/6/7/8/9/10. An antibody may compete for binding to IL22 with, or bind to the same epitope as, an antibody which comprises a LCVR and HCVR sequence pair of SEQ ID NOs: 22/24. An antibody may compete for binding to IL22 with, or bind to the same epitope as a Fab comprising the LC and HC sequence pair given in SEQ ID NO:26/28.

Alternatively, the present invention provides an antibody that competes for binding to IL22 with, or bind to the same epitope as, an antibody which comprises a CDR-L1/CDR-L2/CDR-L3/CDR-H1/CDR-H2/CDR-H3 sequence combination of SEQ ID NOs: 65/66/67/68/69/70. An antibody may compete for binding to IL22 with, or bind to the same epitope as, an antibody which comprises a LCVR and HCVR sequence pair of SEQ ID NOs: 72/74. An antibody may compete for binding to IL22 with, or bind to the same epitope as a Fab comprising the LC and HC sequence pair given in SEQ ID NO: 76/78.

In one embodiment, the present invention provides an anti-IL22 antibody which binds to an epitope on IL22, said epitope comprising the one or more residues VRLIGEKLFHGVSM (SEQ ID NO: 1, residues 72-85 of the amino-acid sequence of IL22). In some embodiments, the present invention provides an anti-IL22 antibody which binds to the polypeptide VRLIGEKLFHGVSM (SEQ ID NO: 96). In embodiments, the invention provides an antibody that binds to at least 1, at least 2, at least 3, at least 4, at least 5, or all residues selected from the residues 72-85 of the amino-acid sequence of IL22 defined by SEQ ID NO: 1.

In one embodiment, the present invention provides an anti-IL22 antibody which binds to an epitope on IL22, said epitope comprising least 3, at least 4, at least 5, at least 6, at least 7, at least 8, at least 9, at least 10, or all of residues selected from the list consisting of Gln48, Glu77, Phe80, His81, Gly82, Va183, Ser84, Met85, Arg88, Leu169, Met172, Ser173, Arg175, Asn176 and Ile179 of human IL22 (SEQ ID NO: 1) as determined at less than 4 Å contact distance. In embodiments, the invention provides an antibody that binds to an epitope on IL22, said epitope comprising at least 3, at least 4, at least 5, at least 6, at least 7, at least 8, at least 9, at least 10, or all of residues selected from the list consisting of Lys44, Phe47, Gln48, Ile75, Gly76, Glu77, Phe80, His81, Gly82, Va183, Ser84, Met85, Ser86, Arg88, Leu169, Met172, Ser173, Arg175, Asn176 and Ile179 of human IL22 (SEQ ID NO: 1) as determined at the distance of less than 5 Å contact distance between the antibody and IL22.

In particular, the invention provides an antibody which may compete for binding to IL22 with, or bind to the same epitope as, an antibody which comprises the residues of the heavy and light chains listed in Tables 4 or 5 below. More particular, an antibody of the invention comprises CDR-H3 sequence comprising residues 97-104, preferably, residues 99-104 of SEQ ID NO. 24 and binds to an epitope on IL22 as defined above. More specifically, an antibody of the invention comprises CDR-H1, CDR-H2 and CDR-H3 residues as defined in Tables 4 or 5 and binds to an epitope on IL22 as defined above.

TABLE 4

Amino acids of the light and heavy chains of the anti-IL22 antibody
of the present invention involved in interactions with IL22 which
have ≤4 Å contact distance between the antibody and
IL-22. The positions of the residues correspond to SEQ ID NO:
26 for the light chain and SEQ ID NO 28 for the heavy chain.

| light chain | heavy chain |
|---|---|
| Tyr30 (CDR1) | Ser31 (CDR1) |
| Thr31 (CDR1) | Tyr32 (CDR1) |
| Asn32 (CDR1) | Ala33 (CDR1) |
| Trp50 (CDR2) | Asp52 (CDR2) |
| Tyr93 (CDR3) | Ile53 (CDR2) |
| | Arg99 (CDR3) |
| | Phe100 (CDR3) |
| | Val101 (CDR3) |
| | Gly102 (CDR3) |
| | Val103 (CDR3) |
| | Asp104 (CDR3) |

TABLE 5

Amino acids of the light and heavy chains of the anti-IL22 antibody
of the present invention involved in interactions with IL22 which
have ≤5 Å contact distance between the antibody and
IL-22. The positions of the residues correspond to SEQ ID NO:
26 for the light chain and SEQ ID NO 28 for the heavy chain.

| light chain | heavy chain |
|---|---|
| Tyr30 (CDR1) | Ser30 (CDR1) |
| Thr31 (CDR1) | Ser31 (CDR1) |
| Asn32 (CDR1) | Tyr32 (CDR1) |
| Trp50 (CDR2) | Ala33 (CDR1) |
| Tyr93 (CDR3) | Ile50 (CDR2) |
| Gly94 (CDR3) | Asp52 (CDR2) |
| Tyr101 (CDR3) | Ile53 (CDR2 |
| | Glu54 (CDR2) |
| | Tyr58 (CDR2) |
| | Arg97 (CDR3) |
| | Asp98 (CDR3) |
| | Arg99 (CDR3) |
| | Phe100 (CDR3) |
| | Val101 (CDR3) |
| | Gly102 (CDR3) |
| | Val103 (CDR3) |
| | Asp104 (CDR3) |

More particularly, the present invention provides an anti-IL22 antibody which binds to an epitope on IL22 as defined above, and wherein said antibody prevents binding of IL22 to IL22R1 and IL22BP. More specifically the light chain of the antibody sterically prevents the binding of IL22R1 to IL22.

The epitope can be identified by any suitable binding site mapping method known in the art in combination with any one of the antibodies provided by the present invention. Examples of such methods include screening peptides of varying lengths derived from full length target protein for binding to the antibody or fragment thereof of the present invention and identify a fragment that can specifically bind to the antibody containing the sequence of the epitope recognized by the antibody. Target peptides may be produced synthetically. Peptides that bind the antibody can be identified by, for example, mass spectrometric analysis. In another example, NMR spectroscopy or X-ray crystallography can be used to identify the epitope bound by an antibody of the present invention. Typically, when the epitope determination is performed by X-ray crystallography, amino acid residues of the antigen within 4 Å from CDRs are considered to be amino acid residues part of the epitope. Once identified, the epitope may serve for preparing fragments which bind an antibody of the present invention and, if required, used as an immunogen to obtain additional antibodies which bind the same epitope.

In one embodiment the epitope of the antibody is determined by X-ray crystallography.

One can easily determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention or the reference antibody causes a conformation change in the antigen and hence preventing the binding of the test antibody.

To determine if an antibody competes for binding with a reference antibody, the above-described binding methodology is performed in two different experimental setups. In a first setup, the reference antibody is allowed to bind to the antigen under saturating conditions followed by assessment of binding of the test antibody to the antigen. In a second setup, the test antibody is allowed to bind to the antigen under saturating conditions followed by assessment of binding of the reference antibody to the protein/peptide. If, in both experimental setups, only the first (saturating) antibody is capable of binding to the protein/peptide, then it is concluded that the test antibody and the reference antibody compete for binding to the antigen. As will be appreciated by the skilled person, an antibody that competes for binding with a reference antibody may not necessarily bind to the identical epitope as the reference antibody, but may sterically block binding of the reference antibody by binding an overlapping or adjacent epitope or cause a conformational change leading to the lack of binding.

Two antibodies bind to the same or overlapping epitope if each competitively inhibits (blocks) binding of the other to the antigen. Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same part of the antigen as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody Variants

In certain embodiments, antibody variants having one or more amino acid substitutions, insertions, and/or deletions are provided. Sites of interest for substitutional mutagenesis include the CDRs and FRs. Amino acid substitutions may be introduced into an antibody of interest and the products screened for a desired activity, e.g., retained/improved antigen binding, decreased immunogenicity, or improved ADCC or CDC.

In certain embodiments, amino acid sequence variants of the antibodies described herein are contemplated. For example, it may be desirable to improve the binding affinity and/or other biological properties of the antibody. Amino acid sequence variants of the anti-IL22 antibody may be prepared by introducing appropriate modifications into the nucleotide sequence encoding the protein, or by peptide synthesis. Such modifications include, for example, deletions from, and/or insertions into and/or substitutions of residues within the amino acid sequences (such as in one or more CDRs and/or framework sequences or in a VH and/or a VL domain) of the anti-IL22 antibody. Any combination of deletion, insertion, and substitution can be made to arrive at the final construct, provided that the final construct possesses the desired characteristics.

In certain embodiments of the variant VH and VL sequences provided herein, each HVR either is unaltered, or contains no more than one, two or three amino acid substitutions.

It will be appreciated that one or more amino acid substitutions, additions and/or deletions may be made to the CDRs provided by the present invention without significantly altering the ability of the antibody to bind to IL22 and to neutralize IL22 activity. The effect of any amino acid substitutions, additions and/or deletions can be readily tested by one skilled in the art, for example by using the methods described herein, particularly those illustrated in the Examples, to determine IL22 binding and inhibition of the IL22 interactions with its receptor IL22R1 and IL22-binding protein.

Consequently, in certain embodiments of the variant VH and VL sequences, each CDR either contains no more than one, two or three amino acid substitutions, wherein such amino-acid substitutions are conservative, and wherein the antibody retains its binding properties to IL22 and blocks IL22 binding to IL22R1 and IL22 binding protein Accordingly, the present invention provides an anti-IL22 antibody comprising one or more CDRs selected from CDR-L1 (comprising SEQ ID NO:5), CDR-L2 (comprising SEQ ID NO:6), CDR-L3 (comprising SEQ ID NO:7), CDR-H1 (comprising SEQ ID NO:8), CDR-H2 (comprising SEQ ID NO:9) and CDR-H3 (comprising SEQ ID NO:10) in which one or more amino acids in one or more of the CDRs has been substituted with another amino acid, for example a similar amino acid as defined herein below.

In one embodiment, the present invention provides an anti-IL22 antibody comprising CDR-L1 (comprising SEQ ID NO:5), CDR-L2 (comprising SEQ ID NO:6), CDR-L3

(comprising SEQ ID NO:7), CDR-H1 (comprising SEQ ID NO:8), CDR-H2 (comprising SEQ ID NO:9) and CDR-H3 (comprising SEQ ID NO:10), for example in which one or more amino acids in one or more of the CDRs has been substituted with another amino acid, such as a similar amino acid as defined herein below. In embodiments, one or more amino acid substitutions in one or more CDRs replaces a free Cysteine residue or modifies a potential Asparagine deamidation site. In embodiments, one or more amino acid substitutions in one or more CDRs modifies a potential Aspartic acid isomerization site. In embodiments, one or more amino acid substitutions in one or more CDRs removes a potential DP hydrolysis site. In embodiments, with reference to CDR-L3 (SEQ ID NO:7) the substitutions are C91S or C91V; N95D; S96A; or a combination thereof; with reference to CDR-H2 (SEQ ID NO:9), the substitutions are D54E, G55A, or a combination thereof; with reference to CDR-H3 (SEQ ID NO:9), the substitutions is D107E, or a combination of the recited substitutions.

In one embodiment, an anti-IL22 antibody of the present invention comprises a light chain variable domain which comprises three CDRs wherein the sequence of CDR-L1 comprises a sequence that has at least 70%, 80%, 90%, 91%, 92%, 93%, 94%, 95%, 96%, 97%, 98%, or 99% identity or similarity to the sequence given in SEQ ID NO:5, CDR-L2 comprises a sequence that has at least 70%, 80%, 90%, 95% or 98% identity or similarity to the sequence given in SEQ ID NO:6 and/or CDR-L3 comprises a sequence that has at least 70%, 80%, 90%, 91%, 92%, 93%, 94%, 95%, 96%, 97%, 98%, or 99% identity or similarity to the sequence given in SEQ ID NO:7.

In one embodiment, an anti-IL22 antibody of the present invention comprises a heavy chain variable domain which comprises three CDRs wherein the sequence of CDR-H1 comprises a sequence that has at least 70%, 80%, 90%, 91%, 92%, 93%, 94%, 95%, 96%, 97%, 98%, or 99% identity or similarity to the sequence given in SEQ ID NO:8, CDR-H2 comprises a sequence that has at least 70%, 80%, 90%, 91%, 92%, 93%, 94%, 95%, 96%, 97%, 98%, or 99% identity or similarity to the sequence given in SEQ ID NO:9 and/or CDR-H3 comprises a sequence that has at least 70%, 80%, 90%, 91%, 92%, 93%, 94%, 95%, 96%, 97%, 98%, or 99% identity or similarity to the sequence given in SEQ ID NO:10.

In one embodiment, an anti-IL22 antibody of the present invention comprises a light chain variable region comprising a sequence having at least 70%, 80%, 90%, 91%, 92%, 93%, 94%, 95%, 96%, 97%, 98%, or 99% identity or similarity to the sequence given in SEQ ID NO:22.

In one embodiment, an antibody of the present invention comprises a heavy chain variable region comprising a sequence having at least 70%, 80%, 90%, 91%, 92%, 93%, 94%, 95%, 96%, 97%, 98%, or 99% identity or similarity to the sequence given in SEQ ID NO:24.

In one embodiment, an anti-IL22 antibody of the present invention comprises a light chain variable region and a heavy chain variable region, wherein the light chain variable region comprises a sequence having at least 70%, 80%, 90%, 91%, 92%, 93%, 94%, 95%, 96%, 97%, 98%, or 99% identity or similarity to given in SEQ ID NO:22 and/or the heavy chain variable region comprises a sequence having at least 70%, 80%, 90%, 91%, 92%, 93%, 94%, 95%, 96%, 97%, 98%, or 99% identity or similarity to given in SEQ ID NO:24.

In one embodiment, an anti-IL22 antibody of the present invention comprises CDR-L1/CDR-L2/CDR-L3/CDR-H1/CDR-H2/CDR-H3 sequences comprising SEQ ID NOs:65/

66/67/68/69/70 respectively, and the remainder of the light chain and heavy chain variable regions have at least 70%, 80%, 90%, 91%, 92%, 93%, 94%, 95%, 96%, 97%, 98%, or 99% identity or similarity to SEQ ID NO: 72 and 74 respectively.

In one embodiment, an anti-IL22 antibody of the present invention comprises CDR-L1/CDR-L2/CDR-L3/CDR-H1/CDR-H2/CDR-H3 sequences comprising SEQ ID NO s: 5/6/7/8/9/10 respectively, and the remainder of the light chain and heavy chain variable regions have at least 70%, 80%, 90%, 91%, 92%, 93%, 94%, 95%, 96%, 97%, 98%, or 99% identity or similarity to SEQ ID NO: 22 and 24 respectively.

In one embodiment an anti-IL22 antibody of the present invention is a Fab comprising a light chain comprising sequence having at least 70%, 80%, 90%, 91%, 92%, 93%, 94%, 95%, 96%, 97%, 98%, or 99% identity or similarity to the sequence given in SEQ ID NO:26 and a heavy chain comprising sequence having at least 70%, 80%, 90%, 91%, 92%, 93%, 94%, 95%, 96%, 97%, 98%, or 99% identity or similarity to the sequence given in SEQ ID NO:28.

In one embodiment, an anti-IL22 antibody of the present invention is a Fab comprising CDR-L1/CDR-L2/CDR-L3/CDR-H1/CDR-H2/CDR-H3 sequences given in SEQ ID NO s: 5/6/7/8/9/10 respectively, and the remainder of the of the light chain and heavy chain has at least 70%, 80%, 90%, 91%, 92%, 93%, 94%, 95%, 96%, 97%, 98%, or 99% identity or similarity to SEQ ID Nos:26 and 28 respectively.

In one embodiment, an antibody of the present invention comprises a light chain variable region and a heavy chain variable region, wherein the light chain variable region comprises the sequence given in SEQ ID NO:22, wherein one or more residues at the positions 91, 95, and/or 96 have been substituted by another amino-acid; and the heavy chain variable region comprises the sequence given in SEQ ID NO:24, wherein one or more residues at the positions 54, 55, and/or 107 have been substituted by another amino-acid.

The present invention provides an anti-IL22 antibody comprising one or more CDRs selected from CDR-L1 (comprising SEQ ID NO:65), CDR-L2 (comprising SEQ ID NO:66), CDR-L3 (comprising SEQ ID NO:67), CDR-H1 (comprising SEQ ID NO:68), CDR-H2 (comprising SEQ ID NO:69) and CDR-H3 (comprising SEQ ID NO:70) in which one or more amino acids in one or more of the CDRs has been substituted with another amino acid, for example a similar amino acid as defined herein below.

In one embodiment, the present invention provides an anti-IL22 antibody comprising CDR-L1 (comprising SEQ ID NO:65), CDR-L2 (comprising SEQ ID NO:66), CDR-L3 (comprising SEQ ID NO:67), CDR-H1 (comprising SEQ ID NO:68), CDR-H2 (comprising SEQ ID NO:69) and CDR-H3 (comprising SEQ ID NO:70), for example in which one or more amino acids in one or more of the CDRs has been substituted with another amino acid, such as a similar amino acid as defined herein below. In embodiments, one or more amino acid substitutions in one or more CDRs replaces a free Cysteine residue or modifies a potential Asparagine deamidation site. In embodiments, one or more amino acid substitutions in one or more CDRs modifies a potential Aspartic acid isomerization site. In embodiments, one or more amino acid substitutions in one or more CDRs removes a potential DP hydrolysis site. In embodiments, with reference to CDR-H2 (SEQ ID NO:69) the substitution is S61T.

In one embodiment, an anti-IL22 antibody of the present invention comprises a light chain variable domain which comprises three CDRs wherein the sequence of CDR-L1 comprises a sequence that has at least 70%, 80%, 90%, 91%, 92%, 93%, 94%, 95%, 96%, 97%, 98%, or 99% identity or similarity to the sequence given in SEQ ID NO:65, CDR-L2 comprises a sequence that has at least 70%, 80%, 90%, 91%, 92%, 93%, 94%, 95%, 96%, 97%, 98%, or 99% identity or similarity to the sequence given in SEQ ID NO:66 and/or CDR-L3 comprises a sequence that has at least 70%, 80%, 90%, 91%, 92%, 93%, 94%, 95%, 96%, 97%, 98%, or 99% identity or similarity to the sequence given in SEQ ID NO:67.

In one embodiment, an anti-IL22 antibody of the present invention comprises a heavy chain variable domain which comprises three CDRs wherein the sequence of CDR-H1 comprises a sequence that has at least 70%, 80%, 90%, 91%, 92%, 93%, 94%, 95%, 96%, 97%, 98%, or 99% identity or similarity to the sequence given in SEQ ID NO: 68, CDR-H2 comprises a sequence that has at least 70%, 80%, 90%, 91%, 92%, 93%, 94%, 95%, 96%, 97%, 98%, or 99% identity or similarity to the sequence given in SEQ ID NO:69 and/or CDR-H3 comprises a sequence that has at least 70%, 80%, 90%, 91%, 92%, 93%, 94%, 95%, 96%, 97%, 98%, or 99% identity or similarity to the sequence given in SEQ ID NO:70.

In one embodiment, an anti-IL22 antibody of the present disclosure comprises a light chain variable region comprising a sequence having at least 70%, 80%, 90%, 91%, 92%, 93%, 94%, 95%, 96%, 97%, 98%, or 99% identity or similarity to the sequence given in SEQ ID NO:72.

In one embodiment, an antibody of the present disclosure comprises a heavy chain variable region comprising a sequence having at least 70%, 80%, 90%, 91%, 92%, 93%, 94%, 95%, 96%, 97%, 98%, or 99% identity or similarity to the sequence given in SEQ ID NO:74.

In one embodiment, an anti-IL22 antibody of the present invention comprises a light chain variable region and a heavy chain variable region, wherein the light chain variable region comprises a sequence having at least 70%, 80%, 90%, 91%, 92%, 93%, 94%, 95%, 96%, 97%, 98%, or 99% identity or similarity to given in SEQ ID NO:72 and/or the heavy chain variable region comprises a sequence having at least 70%, 80%, 90%, 91%, 92%, 93%, 94%, 95%, 96%, 97%, 98%, or 99% identity or similarity to given in SEQ ID NO:74.

In one embodiment, an anti-IL22 antibody of the present invention comprises CDR-L1/CDR-L2/CDR-L3/CDR-H1/CDR-H2/CDR-H3 sequences comprising SEQ ID NOs: 65/66/67/68/69/70 respectively, and the remainder of the light chain and heavy chain variable regions have at least 70%, 80%, 90%, 91%, 92%, 93%, 94%, 95%, 96%, 97%, 98%, or 99% identity or similarity to SEQ ID Nos: 72 and 74 respectively.

In one embodiment an anti-IL22 antibody of the present invention is a Fab comprising a light chain comprising sequence having at least 70%, 80%, 90%, 91%, 92%, 93%, 94%, 95%, 96%, 97%, 98%, or 99% identity or similarity to the sequence given in SEQ ID NO:76 and a heavy chain comprising sequence having at least 70%, 80%, 90%, 91%, 92%, 93%, 94%, 95%, 96%, 97%, 98%, or 99% identity or similarity to the sequence given in SEQ ID NO:78.

In one embodiment, an anti-IL22 antibody of the present invention is a Fab comprising CDR-L1/CDR-L2/CDR-L3/CDR-H1/CDR-H2/CDR-H3 sequences given in SEQ ID NOs: respectively, and the remainder of the of the light chain and heavy chain has at least 70%, 80%, 90%, 95% or 98% identity or similarity to SEQ ID NO:76 and 78 respectively.

Sequence Identity and Similarity

Degrees of identity and similarity between sequences can be readily calculated. The "% sequence identity" (or "% sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) amino-acids (e.g., identical amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to obtain the % sequence identity or percent sequence similarity.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). Polypeptide sequences also can be compared using FASTA using default or recommended parameters. FASTA (e.g., FASTA2 and FASTA3) provides alignments and percent sequence identity of the regions of the best overlap between the query and search sequences.

In certain embodiments, substitutions, insertions, or deletions may occur within one or more CDR so long as such alterations do not substantially reduce the ability of the antibody to bind the target.

For example, conservative alterations that do not substantially reduce binding affinity may be made in CDRs. Such alterations may be made outside of antigen contacting residues in the CDRs.

Conservative substitutions are shown in Table 6 together with more substantial "exemplary substitutions".

TABLE 6

| Examples of amino-acid substitutions | | |
| --- | --- | --- |
| Original Residue | Exemplary Substitutions | Conservative Substitution |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys(C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |

TABLE 6-continued

Examples of amino-acid substitutions

| Original Residue | Exemplary Substitutions | Conservative Substitution |
|---|---|---|
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; | Leu |

Substantial modifications in the biological properties of an antibody variant can be accomplished by selecting substitutions that differ significantly in their effect on maintaining the structure of the polypeptide backbone in the area of the substitution, the charge or hydrophobicity of the molecule at the target site, or the bulk of the side chain. Amino acids may be grouped according to similarities in the properties of their side chains (in A. L. Lehninger, Biochemistry second ed., pp. 73-75, Worth Publishers, New York (1975))

One type of substitutional variant involves substituting one or more CDR region residues of a parent antibody (humanized or human antibody). Generally, the resulting variant(s) selected for further study will have changes in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207: 179-196 (2008)), and/or residues that contact antigen, with the resulting variant VH or VL being tested for binding affinity Affinity maturation by constructing and reselecting from secondary libraries has been described, e.g., in Hoogenboom et al. m Methods in Molecular Biology 178: 1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity.

One of the methods that can be used for identification of residues or regions of an antibody that may be targeted for mutagenesis is alanine scanning mutagenesis (Cunningham and Wells (1989) Science, 244: 1081-1085). In this method, a residue or a number of target residues are identified and replaced by alanine to determine whether the interaction of the antibody with antigen is affected. Alternatively, or additionally, an X-ray structure of an antigen-antibody complex can be used to identify contact points between the antibody and its antigen. Variants may be screened to determine whether they contain the desired properties.

Constant Region Variants

In some embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

Antibodies with increased half-lives and improved binding to the neonatal Fc receptor (FcRn) are described in US2005/0014934A1. Those antibodies comprise an Fc region with one or more substitutions therein which improve binding of the Fc region to FcRn.

In certain embodiments, an antibody variant comprises an Fc region with one or more amino acid substitutions which improve ADCC, e.g., substitutions at positions 298, 333, and/or 334 of the Fc region (EU numbering of residues).

Antibodies with reduced effector function include those with substitution of one or more of Fc region residues 234, 235, 237, 238, 265, 269, 270, 297, 327 and 329 (see, e.g., U.S. Pat. No. 6,737,056). Such Fc mutants include Fc mutants with substitutions at two or more of amino acid positions 265, 269, 270, 297 and 327 wherein the amino acid residue is numbered according to the EU numbering system.

In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FORT, FcγRII and FcγRIII. FcR expression on hematopoietic cells is summarized in Ravetch and Kinet, Annu. Rev. Immunol. 9:457-492 (1991). Non-limiting examples of in vitro assays to assess ADCC activity of a molecule of interest is described in U.S. Pat. Nos. 5,500,362; 5,821,337. Alternatively, or additionally, ADCC activity of the molecule of interest may be assessed in vivo, e.g., in an animal model such as that disclosed in Clynes et al. Proc. Nat 1 Acad. Sci. USA 95:652-656 (1998). Clq binding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al, J. Immunol. Methods 202: 163 (1996); Cragg, M. S. et al, Blood 101: 1045-1052 (2003); and Cragg, M. S. and M. I Glennie, Blood 103:2738-2743 (2004)). FcRn binding and in vivo clearance/half-life determinations can also be performed using methods known in the art (see, e.g., Petkova, S. B. et al, Intl. Immunol. 18(12): 1759-1769 (2006)).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Humanized, Human, and Chimeric Antibodies

The antibodies of the present invention may be, but are not limited to, humanized, fully human or chimeric antibodies.

In one embodiment, the antibody is humanized. More particular the anti-IL22 antibody is a chimeric, human, or humanized antibody.

In certain embodiments, an antibody provided herein is a chimeric antibody. Examples of chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In another example, a chimeric antibody is a "class switched" antibody in which the class or subclass has been changed from that of the parent antibody.

Chimeric antibodies are composed of elements derived from two different species such that the element retains the characteristics of the species from which it is derived. Generally a chimeric antibody will comprise a variable region from one species, for example a mouse, rat, rabbit or similar and constant region from another species such as a human.

In certain embodiments, a chimeric antibody is a humanized antibody.

It will be appreciated that it may only be necessary to transfer the specificity determining residues of the CDRs rather than the entire CDR (see for example, Kashmiri et al., 2005, Methods, 36, 25-34). Humanized antibodies may optionally further comprise one or more framework residues derived from the non-human species from which the CDRs were derived.

Suitably, the humanized antibody according to the present invention has a variable domain comprising human acceptor framework regions as well as one or more of the CDRs and optionally further including one or more donor framework residues.

In one embodiment the antibody is a humanized antibody, wherein the variable domain comprises human acceptor framework regions and non-human donor CDRs.

When the CDRs are grafted, any appropriate acceptor variable region framework sequence may be used having regard to the class/type of the donor antibody from which the CDRs are derived, including mouse, primate and human framework regions.

Examples of human frameworks which can be used in the present invention are KOL, NEWM, REI, EU, TUR, TEI, LAY and POM (Kabat et al). For example, KOL and NEWM can be used for the heavy chain, REI can be used for the light chain and EU, LAY and POM can be used for both the heavy chain and the light chain. Alternatively, human germline sequences may be used; these are available at: www.imgt.org. In embodiments, the acceptor framework is IGKV1D-13 human germline, IGHV3-66 human germline, IGKV1-12 human germline, and/or IGHV4-31 human germline. In embodiments, the human framework contains 1-5, 1-4, 1-3 or 1-2 donor antibody amino acid residues.

In a humanized antibody of the present invention, the acceptor heavy and light chains do not necessarily need to be derived from the same antibody and may, if desired, comprise composite chains having framework regions derived from different chains.

In some embodiments, the antibody is a human antibody. Human antibodies can be produced using various techniques known in the art. More particular the anti-IL22 antibody comprises a human antibody heavy chain constant region and a human light chain constant region.

Human antibodies comprise heavy or light chain variable regions or full length heavy or light chains that are derived from a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is derived from a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is derived from a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertories (Winter G; (1994) Annu Rev Immunol 12:433-455, Green L L, (1999) J Immunol Methods 231:1 1-23). Human antibodies may be produced, for example, by mice in which the murine immunoglobulin variable and optionally the constant region genes have been replaced by their human counterparts as described, for example, in U.S. Pat. Nos. 5,545,806, 5,569, 825, 5,625,126, 5,633,425, 5,661,016, and 5,770,429.

Effector Molecules

If desired an antibody according to the present invention may be conjugated to one or more effector molecule(s). In one embodiment the antibody is not attached an effector molecule.

It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 1251, 1311, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO2005/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment, the polymer is albumin or a fragment thereof, such as human serum albumin or a fragment thereof.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example, the antibody according to the present invention are attached to poly(ethyleneglycol) (PEG) moieties. In one particular embodiment, the antigen-binding fragment according to the present invention and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the antibody is a modified Fab' fragment having at the C-terminal end of its heavy chain a modified hinge region containing at least one cysteine residue to which an effector molecule is attached. Suitably the effector molecule is PEG and is attached using the methods described in (WO 98/25971 and WO 2004072116 or in WO 2007/003898. Effector molecules may be attached to antibody fragments using the methods described in International patent applications WO 2005/003169, WO 2005/003170 and WO 2005/003171.

In one embodiment the antibody is not attached an effector molecule.

Polynucleotides and Vectors

The present invention also provides an isolated polynucleotide encoding the antibody or a part thereof according to the present invention. The isolated polynucleotide according to the present invention may comprise synthetic DNA, for instance produced by chemical processing, cDNA, genomic DNA or any combination thereof.

TABLE 7

| Amino-acid sequences of the anti-IL22 antibodies and their corresponding nucleic acid sequences. | | |
|---|---|---|
| Antibody sequence | Amino-acid SEQ ID NO | Nucleic acid SEQ ID NO |
| 11041 | | |
| 11041 light chain V region | 22 | 23 |
| 11041 heavy chain V region | 24 | 25 |
| 11041 light chain | 26 | 27 |
| 11041 heavy chain Fab | 28 | 29 |
| 11041 heavy chain IgG1 | 30 | 31 |
| 11041 heavy chain IgG4P | 32 | 33 |
| 11070 | | |
| 11070 light chain V region | 72 | 73 |
| 11070 heavy chain V region | 74 | 75 |
| 11070 light chain | 76 | 77 |
| 11070 heavy chain Fab | 78 | 79 |
| 11070 heavy chain IgG1 | 80 | 81 |
| 11070 heavy chain IgG4P | 82 | 83 |

Examples of suitable sequences are provided herein. Thus in one embodiment the present invention provides an isolated polynucleotide encoding an antibody, comprising a sequence given in SEQ ID NOs 23, 25, 27, 29, 31, 33, 73, 75, 77, 79, 81, and 83.

In one embodiment, the present invention provides an isolated polynucleotide encoding the heavy chain of an antibody Fab fragment or of an IgG1 or IgG4P antibody of the present invention which comprises the sequence given in SEQ ID NO:29, 31, 33 respectively.

Also provided is an isolated polynucleotide encoding the light chain of an antibody Fab fragment or of an IgG1 or IgG4 antibody of the present invention which comprises the sequence given in SEQ ID NO: 79, 81, 83 respectively.

In another embodiment, the present invention provides an isolated polynucleotide encoding the heavy chain and the light chain of an Fab antibody of the present invention in which the polynucleotide encoding the heavy chain comprises the sequence given in SEQ ID NO: 29 or 79 and the polynucleotide encoding the light chain comprises the sequence given in SEQ ID NO: 27 or 77.

The present invention also provides for a cloning or expression vector comprising one or more polynucleotides described herein. In one example, the cloning or expression vector according to the present invention comprises one or more isolated polynucleotides comprising a sequence selected from SEQ ID NO: 23, 25, 27, 29, 31, 33, 73, 75, 77, 79, 81, and 83.

Standard techniques of molecular biology may be used to prepare DNA sequences coding for the antibody or antigen-binding fragment thereof of the present invention. Desired DNA sequences may be synthesized completely or in part using oligonucleotide synthesis techniques. Site-directed mutagenesis and polymerase chain reaction (PCR) techniques may be used as appropriate.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Host Cells for Production of the Antibodies and Antigen-Binding Fragments Thereof Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody or antigen-binding fragment thereof of the present invention. Bacterial, for example E. coli, and other microbial systems may be used or eukaryotic, for example mammalian, host cell expression systems may also be used. Suitable mammalian host cells include CHO, myeloma or hybridoma cells.

In a further embodiment, a host cell comprising such nucleic acid(s) or vector(s) is provided. In one such embodiment, a host cell comprises (e.g., has been transformed with): (1) a vector comprising a nucleic acid that encodes an amino acid sequence comprising the VL of the anti-IL22 antibody and an amino acid sequence comprising the VH of the anti-IL22 antibody, or (2) a first vector comprising a nucleic acid that encodes an amino acid sequence comprising the VL of the anti-IL22 antibody and a second vector comprising a nucleic acid that encodes an amino acid sequence comprising the VH of the anti-IL22 antibody. In one embodiment, the host cell is eukaryotic, e.g. a Chinese Hamster Ovary (CHO) cell or lymphoid cell (e.g., Y0, NS0, Sp20 cell). In one embodiment, the host cell is prokaryotic, e.g. an E. coli cell. In one embodiment, a method of making an anti-IL22 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N J, 2003), pp. 245-254, describing expression of antibody fragments in E. coli.). After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22: 1409-1414 (2004), and Li et al., Nat. Biotech. 24:210-215 (2006).

Suitable types of Chinese Hamster Ovary (CHO cells) for use in the present invention may include CHO and CHO-K1 cells including dhfr-CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NS0 myeloma cells and SP2 cells, COS cells. The host cell may be stably transformed or transfected with the isolated polynucleotide sequences or the expression vectors according to the present invention.

Process for the Production of the Antibodies

The present invention also provides a process for the production of an antibody according to the present invention comprising culturing a host cell according to the present invention under conditions suitable for producing the antibody according to the invention and isolating the antibody.

The antibody may comprise only a heavy or light chain polypeptide, in which case only a heavy chain or light chain polypeptide coding sequence needs to be used to transfect the host cells. For production of antibodies or antigen-binding fragments thereof comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Thus, there is provided a process for culturing a host cell and expressing an antibody, isolating the antibody and optionally purifying the antibody to provide an isolated antibody. In one embodiment, the process further comprises the step of conjugating an effector molecule to the isolated antibody.

The present invention also provides a process for the production of an antibody according to the present invention comprising culturing a host cell containing a vector of the present invention under conditions suitable for leading to expression of protein from DNA encoding the antibody molecule of the present invention and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies according to the present invention are expressed at good levels from host cells. Thus the properties of the antibodies appear to be optimized for commercial processing.

Purified Antibody

In one embodiment there is provided a purified antibody, for example a humanized antibody, in particular an antibody according to the invention, in substantially purified from, in particular free or substantially free of endotoxin and/or host cell protein or DNA.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

In Vitro and Ex Vivo Use of Antibody

The present invention also provides an in vitro or ex vivo method of inhibiting IL-22 induced STAT3 phosphorylation, the method comprising contacting and incubating keratinocyte cells with an antibody of the invention. Any keratinocyte cells and their derivatives can be used, including, for example, HaCaT cells.

The present invention further provides an in vitro or ex vivo method of inhibiting IL-22 induced IL-10 release, the method comprising contacting and incubating epithelial cells with an antibody according to the present invention. More specifically COLO205 cells may be used.

Also is provided an in vitro or ex vivo method of inhibiting IL22 induced s100A7 release, the method comprising contacting and incubating keratinocytes with an antibody according to the present invention.

Also is provided an in vitro or ex vivo method of inhibiting IL22 induced epidermal or corneal thickening associated with aberrant keratinocyte differentiation and parakeratosis, the method comprising contacting and incubating a reconstituted epithelium consisting of keratinocytes and dermal fibroblasts with an antibody according to the present invention. In particular the aberrant keratinocyte proliferation and differentiation demonstrated by epidermal/corneal thickening and parakeratosis induced by IL22 is inhibited.

The cells are generally incubated for the time sufficient to allow an antibody to bind to IL22 and cause the biological effect.

The Examples provides the descriptions of the methods involving anti-IL22 antibodies that can be used to achieve certain biological effects.

Therapeutic Use of the Antibodies

The antibodies of the invention, formulations, or pharmaceutical compositions thereof may be administered for prophylactic and/or therapeutic treatments.

The present invention provides an anti-IL22 antibody of the invention or pharmaceutical composition thereof for use as a medicament.

In prophylactic applications, antibodies, formulations, or compositions are administered to a subject at risk of a disorder or condition as described herein, in an amount sufficient to prevent or reduce the subsequent effects of the condition or one or more of its symptoms.

In therapeutic applications, the antibodies are administered to a subject already suffering from a disorder or condition as described herein, in an amount sufficient to cure, alleviate or partially arrest the condition or one or more of its symptoms. Such therapeutic treatment may result in a decrease in severity of disease symptoms, or an increase in frequency or duration of symptom-free periods.

The subjects to be treated can be animals. Preferably, the pharmaceutical compositions according to the present invention are adapted for administration to human subjects.

The present invention provides a method of treating a disorder or condition as described herein in a subject in need thereof, the method comprising administering to the subject an antibody according to the present invention. Such antibody is administered in a therapeutically effective amount.

The present invention also provides an antibody of the invention for use in the treatment of a disorder or condition as described herein.

Therapeutic Indications

Antibodies of present invention may be used in treating, preventing or ameliorating any condition that is associated with IL22 or IL22R1 activity; for example, any condition which results in whole or in part from signaling through IL22R1 receptor.

High levels of IL22 have been found in human psoriatic plaques (Boniface et al., Clin Exp Immunol. 150: 407-415 (2007)) and the involvement of this cytokine in the pathogenesis of psoriasis has been demonstrated in mouse models of skin inflammation (Van Belle et al. J Immunol. January 1; 188(1):462-9 (2012)). The ligands, such as IL22, that signal via the IL22R1 have been implicated in a number of diseases and since IL22R1 is predominantly expressed in epithelial and stromal cells, the key diseases are those affecting stroma and epithelia, for example, in the skin.

The antibodies and compositions of the present invention can be used to treat an inflammatory skin condition. In certain embodiments, inflammatory skin condition is selected from psoriasis, psoriatic arthritis, contact dermatitis, chronic hand eczema or atopic dermatitis. More specifically, the inflammatory skin condition is atopic dermatitis.

In particular, the antibodies and compositions of the invention may be used to inhibit IL22 mediated epidermal thickening associated with aberrant keratinocyte differentiation and parakeratosis in a subject diagnosed with an inflammatory skin condition by reducing aberrant IL22 mediated keratinocyte proliferation and differentiation.

Consequently, the invention provides a method of attenuating impaired barrier function of the skin, and/or parakeratosis, and/or the release of cytokines and/or antimicrobial peptides, such as, for example, S100A7 in a subject diagnosed with an inflammatory skin condition, the method comprising administering to said subject an antibody as provided in the present invention.

In yet another embodiment the present invention provides an antibody of the invention for use in attenuating impaired barrier function of the skin, and/or parakeratosis, and/or the release of cytokines and/or antimicrobial peptides, such as, for example, S100A7 in a subject diagnosed with an inflammatory skin condition.

In yet another embodiment the present invention provides use of an antibody of the invention for the manufacture of a medicament for attenuating impaired barrier function of the skin, and/or parakeratosis, and/or the release of cytokines and/or antimicrobial peptides, such as, for example, S100A7 in a subject diagnosed with a skin inflammatory disease.

In particular, such attenuation of impaired barrier function of the skin is achieved by reducing aberrant IL-22 mediated keratinocyte proliferation and differentiation.

The antibodies and compositions of the present invention can be used to directly or indirectly inhibit the proliferation, differentiation, and/or survival of immune or hematopoietic cells, such as myeloid, lymphoid, or erythroid cells, or precursor cells thereof.

The antibodies and compositions of the present invention can be used to treat a variety of immune disorders and hyperproliferative disorders.

Examples of immune disorders that can be treated include, but are not limited to, autoimmune disorders, e.g., arthritis (including rheumatoid arthritis (RA), juvenile rheumatoid arthritis, osteoarthritis, psoriatic arthritis, lupus-associated arthritis or ankylosing spondylitis), scleroderma, systemic lupus erythematosis, HIV, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); cardiovascular disorders, e.g., cholesterol metabolic disorders, oxygen free radical injury, ischemia; disorders associated with wound healing; respiratory disorders, e.g., asthma and COPD (e.g., cystic fibrosis); acute inflammatory conditions (e.g., endotoxemia, sepsis and septicaemia, toxic shock syndrome and infectious disease); transplant rejection and allergy The antibodies and compositions of the present invention can be used to treat an IL-22-associated disorder such as, an arthritic disorder, e.g., rheumatoid arthritis, juvenile rheumatoid arthritis, osteoarthritis, psoriatic arthritis, or ankylosing spondylitis; a respiratory disorder (e.g., asthma, chronic obstructive pulmonary disease (COPD); cardiovascular system (e.g., atherosclerosis), nervous system (e.g., Alzheimer's disease), liver (e.g., hepatitis), kidney (e.g., nephritis), pancreas (e.g., pancreatitis), and gastrointestinal organs, e.g., colitis, Crohn's disease and IBD; acute inflammatory conditions, e.g., endotoxemia, sepsis and septicaemia, toxic shock syndrome and infectious disease; multiple organ failure; respiratory disease (ARD); amyloidosis; nephropathies such as glomerulosclerosis, membranous neuropathy, renal arteriosclerosis, glomerulonephritis, fibroproliferative diseases of the kidney, as well as other kidney disfunctions and renal tumors.

The anti-IL-22 antibodies and compositions of the invention can be used to treat epithelial cancers, e.g., carcinoma, melanoma and others. IL-22 inhibition in these and other disease states is disclosed in WO 03/083062

The antibodies and compositions of the present invention may similarly be used to treat multiple sclerosis in humans. In the mouse model for multiple sclerosis (Tuohy et al. (J. Immunol. (1988) 141: 1126-1130), Sobel et al. (J. Immunol. (1984) 132: 2393-2401), and Traugott (Cell Immunol. (1989) 119: 114-129), treatment of mice with anti-IL22 antibodies may profoundly delay the onset of the disease.

The antibodies and compositions of the present invention may be used to treat rheumatoid arthritis (RA) or other arthritic diseases. In RA synovial biopsies, IL22 protein is detected in vimentin+synovial fibroblasts and some CD68+ macrophages while IL22R1 is detected in synovial fibroblasts. Inhibitors of IL22 ameliorate symptoms of rheumatoid arthritis (WO2005/000897; U.S. Pat. No. 6,939,545).

The antibodies and compositions of the present invention may be used to reduce the mixed lymphocyte reaction (MLR) and treat transplant rejection and related diseases (e.g., graft versus host disease) that are dependent on IL22. MLR and transplantation models have been described by Current Protocols in Immunology, Second Edition, Coligan et al. eds., John Wiley & Sons, 1994; Kasaian et al. (Immunity (2002) 16: 559-569)).

The antibodies and compositions of the present invention may also be used to treat hyperproliferative disorders associated with aberrant activity of IL22-responsive cells and IL22R1/IL10R2-responsive cells by administering the antibodies in an amount sufficient to inhibit or reduce hyperproliferation of IL22 and/or IL22R1 and/or IL10R2-responsive cells in a subject.

Hence, the antibodies of the invention may be used to inhibit the progression of neoplasms, e.g. squamous cell carcinomas, basal cell carcinomas, transitional cell papillomas and carcinomas, adenomas, adenocarcinoma, linitis plastica, insulinoma, glucagonoma, gastrinoma, vipoma, cholangiocarcinoma, hepatocellular carcinoma, adenoid cyctic carcinoma, carcinoid tumor of appendix, prolactinoma, oncocytoma, hurthle cell adenoma, renal cell carcinoma, Grawitz tumor, multiple endocrine adenomas, endometroid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, Warthin's tumor, thymoma, specialized gonadal neoplasms, sex cord-stromal tumor, thecoma, granulosa cell tumor, arrhenoblastoma, sertoli-leydig cell tumor, paraganglioma, pheochromocytoma, glomus tumor, melanocytic nevus, malignant melanoma, melanoma, nodular melanoma, dysplastic nevus, lentigo maligna, superficial spreading melanoma, or acral lentiginous melanoma.

The antibodies and compositions of the present invention may also be used to reduce an acute phase response in a subject.

The antibodies and compositions of the present invention may also be used to treat Sjögren syndrome, or cancers selected from hepatocarcinoma, liposarcoma, oral squamous cell carcinoma, colon and colorectal cancer, pancreatic cancer, small- and large-cell lung cancer, breast cancer, glioblastoma, cutaneous T-cell lymphoma, anaplastic large cell lymphoma, mantle cell lymphoma Diagnostic Use of the Antibodies and Antigen-Binding Fragments Thereof The present invention also provides the use of the antibodies of the present invention as diagnostically active agents or in diagnostic assays, for example, for diagnosing skin inflammatory diseases or their severity.

The diagnosis may preferably be performed on biological samples. A "biological sample" encompasses a variety of sample types obtained from an individual and can be used in a diagnostic or monitoring assay. The definition encompasses cerebrospinal fluid, blood such as plasma and serum, and other liquid samples of biological origin such as urine and saliva, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting of free IL22 (e.g. not bound to IL22BP) in a biological sample, which has been obtained from a subject.

Pharmaceutical and Diagnostic Compositions

An antibody of the invention may be provided in a pharmaceutical composition. The pharmaceutical composition will normally be sterile and may additionally comprise a pharmaceutically acceptable adjuvant and/or carrier.

As the antibodies of the present invention are useful in the treatment, diagnosis and/or prophylaxis of a disorder or condition as described herein, the present invention also provides for a pharmaceutical or diagnostic composition comprising an antibody or antigen-binding fragment thereof according to the present invention in combination with one or more of a pharmaceutically acceptable carrier, excipient or diluent.

In particular the antibody or antigen-binding fragment thereof is provided as a pharmaceutical composition comprising one or more of a pharmaceutically acceptable excipient, diluent or carrier.

These compositions may comprise, in addition to the therapeutically active ingredient(s), a pharmaceutically acceptable excipient, carrier, diluent, buffer, stabilizer or other materials well known to those skilled in the art. Such materials should be non-toxic and should not interfere with the efficacy of the active ingredient.

Also provided are compositions, including pharmaceutical formulations, comprising an anti-IL22 antibody of the invention, or polynucleotides comprising sequences encoding an antibody of the invention. In certain embodiments, compositions comprise one or more antibodies of the invention, or one or more polynucleotides comprising sequences encoding one or more antibodies of the invention. These compositions may further comprise suitable carriers, such as pharmaceutically acceptable excipients and/or adjuvants including buffers, which are well known in the art.

Pharmaceutical compositions of an antibody of the present invention are prepared by mixing such antibody having the desired degree of purity with one or more optional pharmaceutically acceptable carriers in the form of lyophilized formulations or aqueous solutions.

Examples of the techniques and protocols mentioned above can be found in Remington's Pharmaceutical Sciences, 20th Edition, 2000, pub. Lippincott, Williams & Wilkins.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be also prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The pharmaceutical compositions of the invention may include one or more pharmaceutically acceptable salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Pharmaceutical compositions typically must be sterile and stable under the conditions of manufacture and storage. The composition can be formulated as a solution, microemulsion, liposome, or other ordered structure suitable to high drug concentration.

In one embodiment, the antibody of the present invention is the sole active ingredient. In another embodiment, an antibody of the present invention is in combination with one or more additional active ingredients. Alternatively, the pharmaceutical compositions comprise the antibody of the present invention which is the sole active ingredient and it may be administered individually to a patient in combination (e.g. simultaneously, sequentially or separately) with other agents, drugs or hormones.

The precise nature of the carrier or other material may depend on the route of administration, e.g. oral, intravenous, cutaneous or subcutaneous, nasal, intramuscular and intra-peritoneal routes. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Solutions for intravenous administration or infusion may contain as carrier, for example, sterile water or preferably they may be in the form of sterile, aqueous, isotonic saline solutions.

Preferably, the pharmaceutical or diagnostic composition comprises a humanized antibody according to the present invention.

Therapeutically Effective Amount and Dosage Determination

The antibodies and pharmaceutical compositions according to the present invention may be administered suitably to a patient to identify the therapeutically effective amount required. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. Compositions may be conveniently presented in unit dose forms containing a predetermined amount of an active agent of the disclosure per dose. Dose ranges and regimens for any of the embodiments described herein include, but are not limited to, dosages ranging from 1 mg-1000 mg unit doses.

A suitable dosage of an antibody or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration of Pharmaceutical Compositions or Formulations

The antibodies described herein or formulations or compositions thereof may be administered for prophylactic and/or therapeutic treatments.

An antibody or pharmaceutical composition of the invention may be administered via one or more routes of administration using one or more of a variety of methods known in the art. As will be appreciated by the skilled person, the route and/or mode of administration will vary depending upon the desired results. Examples of routes of administration for the antibodies or pharmaceutical compositions of the invention include intravenous, intramuscular, intradermal, intraocular, intraperitoneal, subcutaneous, spinal or other parenteral routes of administration, for example by injection or infusion. Alternatively, the antibody or pharmaceutical composition of the invention may be administered via a non-parenteral route, such as a topical, epidermal or mucosal route of administration. The antibody or pharmaceutical composition of the invention may be for oral administration.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain additional agents, such as suspending, preservative, stabilizing and/or dispersing agents. Alternatively, the antibody or antigen-binding fragment thereof according to the invention may be in dry form, for reconstitution before use with an appropriate sterile liquid. Solid forms suitable for solution in, or suspension in, liquid vehicles prior to injection may also be prepared.

Once formulated, the pharmaceutical compositions of the invention can be administered directly to the subject. Accordingly, provided herein is the use of an antibody or an antigen-binding fragment thereof according to the invention for the manufacture of a medicament.

Articles of Manufacture and Kits

The present disclosure also provides kits comprising the anti-IL22 antibodies of the present invention and instructions for use. The kit may further contain one or more additional reagents, such as an additional therapeutic or prophylactic agent as discussed above.

The present invention provides use of an antibody according to the invention or pharmaceutical composition thereof for the manufacture of a medicament.

The present invention also provides use of an antibody of the present invention for the manufacture of a medicament for the treatment of a disorder or condition as described herein.

In certain embodiments, the article of manufacture or kit comprises a container containing one or more of the antibodies of the invention, or the compositions described herein. In certain embodiments, the article of manufacture or kit comprises a container containing nucleic acids(s) encoding one (or more) of the antibodies or the compositions described herein. In some embodiments, the kit includes a cell or cell line that produces an antibody as described herein.

In certain embodiments, the article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treatment, prevention and/or diagnosis and may have a sterile access port. At least one agent in the composition is an antibody of the present invention. The label or package insert indicates that the composition is used for the treatment of an inflammatory skin condition, more specifically atopic dermatitis.

It should be noted that the above-mentioned embodiments illustrate rather than limit the invention, and that those skilled in the art will be able to design many alternative embodiments without departing from the scope of the claims. In the claims, any reference signs placed between parentheses shall not be construed as limiting the claim.

The sequences included in the present invention are shown in Tables 8-10:

TABLE 8

Sequences of IL22

| Name | Sequence | SEQ ID NO |
|------|----------|-----------|
| IL22 | MAALQKSVSSFLMGTLATSCLLLLALLVQGGAAAPISSHCRLDKSNFQ QPYITNRTFMLAKEASLADNNTDVRLIGEKLFHGVSMSERCYLMKQVL NFTLEEVLFPQSDRFQPYMQEVVPFLARLSNRLSTCHIEGDDLHIQRN VQKLKDTVKKLGESGEIKAIGELDLLFMSLRNACI | 1 |
| IL22 (34-179) Without signal peptide | APISSHCRLDKSNFQQPYITNRTFMLAKEASLADNNTDVRLIGEKLFH GVSMSERCYLMKQVLNFTLEEVLFPQSDRFQPYMQEVVPFLARLSNRL STCHIEGDDLHIQRNVQKLKDTVKKLGESGEIKAIGELDLLFMSLRNA CI | 2 |
| His-tagged IL22 | MGSSHHHHHHSSGENLYFQGSQGGAAAPISSHCRLDKSNFQQPYITNR TFMLAKEASLADNNTDVRLIGEKLFHGVSMSERCYLMKQVLNFTLEEV LFPQSDRFQPYMQEVVPFLARLSNRLSTCHIEGDDLHIQRNVQKLKDT VKKLGESGEIKAIGELDLLFMSLRNACI | 3 |
| Cleaved IL22 | GSQGGAAAPISSHCRLDKSNFQQPYITNRTFMLAKEASLADNNTDVRL IGEKLFHGVSMSERCYLMKQVLNFTLEEVLFPQSDRFQPYMQEVVPFL ARLSNRLSTCHIEGDDLHIQRNVQKLKDTVKKLGESGEIKAIGELDLL FMSLRNACI | 4 |

TABLE 9

Sequences of the 11041 antibody and related variants

| Name | Sequence | SEQ ID NO |
|------|----------|-----------|
| 11041 CDRL1 | QASEDIYTNLA | 5 |
| 11041 CDRL2 | WASTLAS | 6 |
| 11041 CDRL3 | QASVYGNAADSRYT | 7 |
| 11041 CDRH1 | GFSLSSYAMI | 8 |
| 11041 CDRH2 | IIDIEGSTYYASWAKG | 9 |
| 11041 CDRH3 | DRFVGVDIFDP | 10 |
| 11041 CDRL1 (not mutated) | Same as SEQ ID NO: 5 | 5 |
| 11041 CDRL2 (not mutated) | Same as SEQ ID NO: 6 | 6 |
| 11041 CDRL3 (not mutated) | QACVYGNSADSRYT | 11 |

TABLE 9-continued

| Name | Sequence | SEQ ID NO |
|------|----------|-----------|
| 11041 CDRL3 C91S | QASVYGNSADSRYT | 12 |
| 11041 CDRL3 C91V | QAVVYGNSADSRYT | 13 |
| 11041 CDRL3 S96A | QACVYGNAADSRYT | 14 |
| 11041 CDRL3 C91S S96A | Same as SEQ ID NO: 7 | 7 |
| 11041 CDRL3 C91V S96A | QAVVYGNAADSRYT | 15 |
| 11041 CDRL3 N95D | QACVYGDSADSRYT | 16 |
| 11041 CDRL3 C91S N95D | QASVYGDSADSRYT | 17 |
| 11041 CDRL3 C91V N95D | QAVVYGDSADSRYT | 18 |
| 11041 CDRH1 (not mutated) | Same as SEQ ID NO: 8 | 8 |
| 11041 CDRH2 (not mutated) | IIDIDGSTYYASWAKG | 19 |
| 11041 CDRH2 G55A | IIDIDASTYYASWAKG | 20 |
| 11041 CDRH2 D54E | Same as SEQ ID NO: 9 | 9 |
| 11041 CDRH3 (not mutated) | Same as SEQ ID NO: 10 | 10 |
| 11041 CDRH3 D107E | DRFVGVDIFEP | 21 |
| 11041 gL6 C91S S96A (gL13) V-region | AVQLTQSPSSLSASVGDRVTITCQASEDIYTNLAWYQQKPGKAPKLLI YWASTLASGVPSRFSGSGSGTDFTLTISSLQPEDFATYYCQASVYGNA ADSRYTFGGGTKVEIK | 22 |
| 11041 gL6 C91S S96A (gL13) V-region | gccgtccaactgactcagtccccgagctcactttccgcgagcgtggga gatcgcgtgaccattacgtgccaggcctcggaggacatctacaccaac ctcgcctggtatcaacagaagcctggcaaagctcccaagctgttgatc tactgggcctccactctggcctccggagtgccttcgcggttctccggt tctggatcaggcaccgacttcaccctgacaatcagcagcctccagccg gaagattttgccacttactactgccaagcatccgtctacgggaacgca gcggactccagatataccttcggcggggggaaccaaagtggagattaag cgtacg | 23 |
| 11041 gH5 D54E (gH14) V-region | EVQLVESGGGLVQPGGSLRLSCAVSGFSLSSYAMIWVRQAPGKGLEWI GIIDIEGSTYYASWAKGRFTISRDNSKNTVYLQMNSLRAEDTAVYYCA RDRFVGVDIFDPWGQGTLVTVSS | 24 |
| 11041 gH5 D54E (gH14) V-region | gaggtgcagctcgtggaaagcggaggaggactggtgcagccaggaggg tccttgcggcttagctgtgccgtgtccggcttctccctgtcctcctac gccatgatctgggtccgccaagctcctgggaagggcctcgaatggatt ggtattatcgacatcgagggatcaacctactacgcctcgtgggccaag ggacggttcaccatctcgcgggacaactccaagaacactgtgtatctg cagatgaacagcctgagggcagaagataccgccgtgtactactgcgcg agagatcgcttcgtgggcgtggacatctttgacccgtggggtcaaggc accctggtcactgtctcgagc | 25 |
| 11041gL13 Light chain | AVQLTQSPSSLSASVGDRVTITCQASEDIYTNLAWYQQKPGKAPKLLI YWASTLASGVPSRFSGSGSGTDFTLTISSLQPEDFATYYCQASVYGNA ADSRYTFGGGTKVEIKRTVAAPSVFIFPPSDEQLKSGTASVVCLLNNE YPREAKVQWKVDNALQSGNSQESVTEQDSKDSTYSLSSTLTLSKADYE KHKVYACEVTHQGLSSPVTKSENRGEC | 26 |
| 11041gL13 Light chain | gccgtccaactgactcagtccccgagctcactttccgcgagcgtggga gatcgcgtgaccattacgtgccaggcctcggaggacatctacaccaac ctcgcctggtatcaacagaagcctggcaaagctcccaagctgttgatc tactgggcctccactctggcctccggagtgccttcgcggttctccggt tctggatcaggcaccgacttcaccctgacaatcagcagcctccagccg gaagattttgccacttactactgccaagcatccgtctacgggaacgca gcggactccagatataccttcggcggggggaaccaaagtggagattaag cgtacggtggccgctcccctccgtgttcatcttcccaccctccgacgag | 27 |

TABLE 9-continued

Sequences of the 11041 antibody and related variants

| Name | Sequence | SEQ ID NO |
|---|---|---|
| | cagctgaagtccggcaccgcctccgtcgtgtgcctgctgaacaacttc taccccgcgaggccaaggtgcagtggaaggtggacaacgccctgcag tccggcaactcccaggaatccgtcaccgagcaggactccaaggacagc acctactccctgtcctccaccctgaccctgtccaaggccgactacgag aagcacaaggtgtacgcctgcgaagtgacccaccagggcctgtccagc cccgtgaccaagtccttcaaccggggcgagtgc | |
| 11041gH14 Fab Heavy chain | EVQLVESGGGLVQPGGSLRLSCAVSGESLSSYAMIWVRQAPGKGLEWI GIIDIEGSTYYASWAKGRFTISRDNSKNTVYLQMNSLRAEDTAVYYCA RDRFVGVDIFDPWGQGTLVTVSSASTKGPSVFPLAPSSKSTSGGTAAL GCLVKDYFPEPVTVSWNSGALTSGVHTFPAVLQSSGLYSLSSVVTVPS SSLGTQTYICNVNHKPSNTKVDKKVEPKSC | 28 |
| 11041gH14 Fab Heavy chain | gaggtgcagctcgtggaaagcggaggaggactggtgcagccaggaggg tccttgcggcttagctgtgccgtgtccggcttctccctgtcctcctac gccatgatctgggtccgccaagctcctgggaagggcctcgaatggatt ggtattatcgacatcgagggatcaacctactacgcctcgtgggccaag ggacggttcaccatctcgcgggacaactccaagaacactgtgtatctg cagatgaacagcctgagggcagaagataccgccgtgtactactgcgcg agagatcgcttcgtgggcgtggacatctttgacccgtggggtcaaggc accctggtcactgtctcgagcgcgtccacaaagggcccatcggtcttc cccctggcaccctcctccaagagcacctctgggggcacagcggccctg ggctgcctggtcaaggactacttccccgaaccagtgacggtgtcgtgg aactcaggtgccctgaccagcggcgttcacaccttcccggctgtccta cagtcttcaggactctactccctgagcagcgtggtgaccgtgccctcc agcagcttgggcacccagacctacatctgcaacgtgaatcacaagccc agcaacaccaaggtcgataagaaagttgagcccaaatcttgt | 29 |
| 11041gH14 heavy chain (IgG1) | EVQLVESGGGLVQPGGSLRLSCAVSGFSLSSYAMIWVRQAPGKGLEWI GIIDIEGSTYYASWAKGRFTISRDNSKNTVYLQMNSLRAEDTAVYYCA RDRFVGVDIFDPWGQGTLVTVSSASTKGPSVFPLAPSSKSTSGGTAAL GCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEK TISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHE ALHNHYTQKSLSLSPGK | 30 |
| 11041gH14 heavy chain (IgG1) | gaggtgcagctcgtggaaagcggaggaggactggtgcagccaggaggg tccttgcggcttagctgtgccgtgtccggcttctccctgtcctcctac gccatgatctgggtccgccaagctcctgggaagggcctcgaatggatt ggtattatcgacatcgagggatcaacctactacgcctcgtgggccaag ggacggttcaccatctcgcgggacaactccaagaacactgtgtatctg cagatgaacagcctgagggcagaagataccgccgtgtactactgcgcg agagatcgcttcgtgggcgtggacatctttgacccgtggggtcaaggc accctggtcactgtctcgagcgcttctacaaagggcccatcggtcttc cccctggcaccctcctccaagagcacctctggggggcacagcggccctg ggctgcctggtcaaggactacttccccgaaccggtgacggtgtcgtgg aactcaggtgccctgaccagcggcgtgcacaccttcccggctgtccta cagtcctcaggactctactccctcagcagcgtggtgaccgtgccctcc agcagcttgggcacccagacctacatctgcaacgtgaatcacaagccc agcaacaccaaggtggacaagaaagttgagcccaaatcttgtgacaaa actcacacatgcccaccgtgcccagcacctgaactcctggggggaccg tcagtcttcctcttccccccaaaacccaaggacaccctcatgatctcc cggacccctgaggtcacatgcgtggtggtggacgtgagccacgaagac cctgaggtcaagttcaactggtacgtggacggcgtggaggtgcataat gccaagacaaagccgcgggaggagcagtacaacagcacgtaccgtgtg gtcagcgtcctcaccgtcctgcaccaggactggctgaatggcaaggag tacaagtgcaaggtctccaacaaagccctcccagcccccatcgagaaa accatctccaaagccaaagggcagccccgagaaccacaggtgtacacc ctgcccccatcccgggatgagctgaccaagaaccaggtcagcctgacc tgcctggtcaaaggcttctatcccagcgacatcgccgtggagtgggag agcaatgggcagccggagaacaactacaagaccacgcctcccgtgctg gactccgacggctccttcttcctctacagcaagctcaccgtggacaag agcaggtggcagcaggggaacgtcttctcatgctccgtgatgcatgag gctctgcacaaccactacacgcagaagagcctctccctgtctccgggt aaa | 31 |
| 11041 gH5 D54E (gH14) heavy chain (IgG4P) | EVQLVESGGGLVQPGGSLRLSCAVSGFSLSSYAMIWVRQAPGKGLEWI GIIDIEGSTYYASWAKGRFTISRDNSKNTVYLQMNSLRAEDTAVYYCA RDRFVGVDIFDPWGQGTLVTVSSASTKGPSVFPLAPCSRSTSESTAAL GCLVKDYFPEPVTVSWNSGALTSGVHTFPAVLQSSGLYSLSSVVTVPS SSLGTKTYTCNVDHKPSNTKVDKRVESKYGPPCPPCPAPEFLGGPSVF LFPPKPKDTLMISRTPEVTCVVVDVSQEDPEVQFNWYVDGVEVHNAKT KPREEQENSTYRVVSVLTVLHQDWLNGKEYKCKVSNKGLPSSIEKTIS | 32 |

TABLE 9-continued

Sequences of the 11041 antibody and related variants

| Name | Sequence | SEQ ID NO |
|------|----------|-----------|
| | KAKGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALH<br>NHYTQKSLSLSLGK | |
| 11041 gH5 D54E<br>(gH14) heavy chain<br>(IgG4P) | gaggtgcagctcgtggaaagcggaggaggactggtgcagccaggaggg<br>tccttgcggcttagctgtgccgtgtccggcttctccctgtcctcctac<br>gccatgatctgggtccgccaagctcctgggaagggcctcgaatggatt<br>ggtattatcgacatcgagggatcaacctactacgcctcgtgggccaag<br>ggacggttcaccatctcgcgggacaactccaagaacactgtgtatctg<br>cagatgaacagcctgagggcagaagataccgccgtgtactactgcgcg<br>agagatcgcttcgtgggcgtggacatctttgacccgtggggtcaaggc<br>accctggtcactgtctcgagcgcttctacaaagggcccctccgtgttc<br>cctctggccccttgctcccggtccacctccgagtctaccgccgctctg<br>ggctgcctggtcaaggactacttccccgagcccgtgacagtgtcctgg<br>aactctggcgccctgacctccggcgtgcacaccttccctgccgtgctg<br>cagtcctccggcctgtactccctgtcctccgtcgtgaccgtgccctcc<br>tccagcctgggcacccaagacctacacctgtaacgtggaccacaagccc<br>tccaacaccaaggtggacaagcgggtggaatctaagtacggccctccc<br>tgccccccctgcccctgcccctgaatttctgggcggaccttccgtgttc<br>ctgttccccccaaagcccaaggacaccctgatgatctcccggacccccc<br>gaagtgacctgcgtggtggtggacgtgtcccaggaagatcccgaggtc<br>cagttcaattggtacgtggacggcgtggaagtgcacaatgccaagacc<br>aagcccagagaggaacagttcaactccacctaccgggtggtgtccgtg<br>ctgaccgtgctgcaccaggactggctgaacggcaaagagtacaagtgc<br>aaggtgtccaacaaggcctgccctccagcatcgaaaagaccatctcc<br>aaggccaagggccagcccccgcgagcccaggtgtacaccctgcccccct<br>agccaggaagagatgaccaagaaccaggtgtccctgacctgtctggtc<br>aagggcttctacccctccgacattgccgtggaatgggagtccaacggc<br>cagcccgagaacaactacaagaccacccccccctgtgctggacagcgac<br>ggctccttcttcctgtactctcggctgaccgtggacaagtcccggtgg<br>caggaaggcaacgtcttctcctgctccgtgatgcacgaggccctgcac<br>aaccactacacccagaagtccctgtccctgagcctgggcaag | 33 |
| Rabbit 11041<br>VL-region | AVVLTQTASPVSAPVGGTVTIKCQASEDIYTNLAWYQQKPGQPPKLLI<br>YWASTLASGVPSRFKGSGSGTEFTLTISDLECADAATYYCQACVYGNS<br>ADSRYTFGGGTEVVVK | 34 |
| Rabbit 11041<br>VL-region | gccgtcgtgctgacccagactgcatccccccgtgtctgcacctgtggga<br>ggcacagtcaccatcaagtgccaggccagtgaggacatttacaccaat<br>ttagcctggtatcaacagaaaccaggacagcctcccaagctcctgatc<br>tactgggcatccactctggcatctggggtcccatcgcggttcaaaggc<br>agtggatctgggacagagttcactctcaccatcagcgacctggagtgt<br>gccgatgctgccacttactactgtcaagcctgtgtttatggcaatagt<br>gctgatagtcggtatactttcggcggagggaccgaggtggtggtcaaa | 35 |
| Rabbit 11041<br>VH-region | QSVEESGGRLVTPGTPLTLTCTVSGFSLSSYAMIWVRQAPGEGLEWIG<br>IIDIDGSTYYASWAKGRFTISRTSTTVDLKITSPTTGDTATYFCARDR<br>FVGVDIFDPWGPGTLVTVSS | 36 |
| Rabbit 11041<br>VH-region | cagtcggtggaggagtccgggggtcgcctggtcacgcctgggacaccc<br>ctgacactcacctgcaccgtctctggattctccctcagtagctatgca<br>atgatctgggtccgccaggctccaggggagggggctggaatggatcgga<br>atcattgatattgatgggagcacatactacgcgagctgggcgaaaggc<br>cgattcaccatctccagaacctcgaccacggtggatctgaaaatcacc<br>agtccgacaaccggggacacggccacctatttctgtgccagagatcgt<br>tttgttggtgttgatattttttgatccctggggcccaggcaccctggtc<br>accgtctcgagc | 37 |
| 11041gL1 V-region | AVVLTQSPSSLSASVGDRVTITCQASEDIYTNLAWYQQKPGKAPKLLI<br>YWASTLASGVPSRFSGSGSGTDFTLTISSLQPEDFATYYCQACVYGNS<br>ADSRYTFGGGTKVEIK | 38 |
| 11041 gL1 C91S<br>V-region (gL2) | AVVLTQSPSSLSASVGDRVTITCQASEDIYTNLAWYQQKPGKAPKLLI<br>YWASTLASGVPSRFSGSGSGTDFTLTISSLQPEDFATYYCQASVYGNS<br>ADSRYTFGGGTKVEIK | 39 |
| 11041 gL1 C91V<br>V-region (gL3) | AVVLTQSPSSLSASVGDRVTITCQASEDIYTNLAWYQQKPGKAPKLLI<br>YWASTLASGVPSRFSGSGSGTDFTLTISSLQPEDFATYYCQAVVYGNS<br>ADSRYTFGGGTKVEIK | 40 |
| 11041gL6 V-region | AVQLTQSPSSLSASVGDRVTITCQASEDIYTNLAWYQQKPGKAPKLLI<br>YWASTLASGVPSRFSGSGSGTDFTLTISSLQPEDFATYYCQACVYGNS<br>ADSRYTFGGGTKVEIK | 41 |

TABLE 9-continued

Sequences of the 11041 antibody and related variants

| Name | Sequence | SEQ ID NO |
|---|---|---|
| 11041gL7 V-region | AIQLTQSPSSLSASVGDRVTITCQASEDIYTNLAWYQQKPGKAPKLLI YWASTLASGVPSRFSGSGSGTDFTLTISSLQPEDFATYYCQACVYGNS ADSRYTFGGGTKVEIK | 42 |
| 11041 gL1 N95D V-region (gL8) | AVVLTQSPSSLSASVGDRVTITCQASEDIYTNLAWYQQKPGKAPKLLI YWASTLASGVPSRFSGSGSGTDFTLTISSLQPEDFATYYCQACVYGDS ADSRYTFGGGTKVEIK | 43 |
| 11041 gL1 S96A V-region (gL9) | AVVLTQSPSSLSASVGDRVTITCQASEDIYTNLAWYQQKPGKAPKLLI YWASTLASGVPSRFSGSGSGTDFTLTISSLQPEDFATYYCQACVYGNA ADSRYTFGGGTKVEIK | 44 |
| 11041 gL1 C91S S96A V-region (gL10) | AVVLTQSPSSLSASVGDRVTITCQASEDIYTNLAWYQQKPGKAPKLLI YWASTLASGVPSRFSGSGSGTDFTLTISSLQPEDFATYYCQASVYGNA ADSRYTFGGGTKVEIK | 45 |
| 11041 gL6 C91S V-region (gL11) | AVQLTQSPSSLSASVGDRVTITCQASEDIYTNLAWYQQKPGKAPKLLI YWASTLASGVPSRFSGSGSGTDFTLTISSLQPEDFATYYCQASVYGNS ADSRYTFGGGTKVEIK | 46 |
| 11041 gL7 C91S V-region (gL12) | AIQLTQSPSSLSASVGDRVTITCQASEDIYTNLAWYQQKPGKAPKLLI YWASTLASGVPSRFSGSGSGTDFTLTISSLQPEDFATYYCQASVYGNS ADSRYTFGGGTKVEIK | 47 |
| 11041 gL7 C91s S96A V-region (gL14) | AIQLTQSPSSLSASVGDRVTITCQASEDIYTNLAWYQQKPGKAPKLLI YWASTLASGVPSRFSGSGSGTDFTLTISSLQPEDFATYYCQASVYGNA ADSRYTFGGGTKVEIK | 48 |
| 11041gH1 V-region | EVQLVESGGGLVQPGGSLRLSCAVSGFSLSSYAMIWVRQAPGKGLEWI GIIDIDGSTYYASWAKGRFTISRDSSKNTVYLQMNSLRAEDTAVYYCA RDRFVGVDIFDPWGQGTLVTVSS | 49 |
| 11041 gH1 G55A V-region (gH2) | EVQLVESGGGLVQPGGSLRLSCAVSGFSLSSYAMIWVRQAPGKGLEWI GIIDIDASTYYASWAKGRFTISRDSSKNTVYLQMNSLRAEDTAVYYCA RDRFVGVDIFDPWGQGTLVTVSS | 50 |
| 11041 gH1 D54E- V-region (gH3) | EVQLVESGGGLVQPGGSLRLSCAVSGFSLSSYAMIWVRQAPGKGLEWI GIIDIEGSTYYASWAKGRFTISRDSSKNTVYLQMNSLRAEDTAVYYCA RDRFVGVDIFDPWGQGTLVTVSS | 51 |
| 11041 gH1 D107E V-region (gH4) | EVQLVESGGGLVQPGGSLRLSCAVSGFSLSSYAMIWVRQAPGKGLEWI GIIDIDGSTYYASWAKGRFTISRDSSKNTVYLQMNSLRAEDTAVYYCA RDRFVGVDIFEPWGQGTLVTVSS | 52 |
| 11041gH5 V-region | EVQLVESGGGLVQPGGSLRLSCAVSGESLSSYAMIWVRQAPGKGLEWI GIIDIDGSTYYASWAKGRFTISRDNSKNTVYLQMNSLRAEDTAVYYCA RDRFVGVDIFDPWGQGTLVTVSS | 53 |
| 11041gH8 V-region | EVQLVESGGGLVQPGGSLRLSCAVSGFSLSSYAMIWVRQAPGKGLEWI GIIDIDGSTYYASWAKGRFTISRDSSKNTLYLQMNSLRAEDTAVYYCA RDRFVGVDIFDPWGQGTLVTVSS | 54 |
| 11041gH9 V-region | EVQLVESGGGLVQPGGSLRLSCAASGESLSSYAMIWVRQAPGKGLEWI GIIDIDGSTYYASWAKGRFTISRDSSKNTVYLQMNSLRAEDTAVYYCA RDRFVGVDIFDPWGQGTLVTVSS | 55 |
| 11041gH11 V-region | EVQLVESGGGLVQPGGSLRLSCAVSGFSLSSYAMIWVRQAPGKGLEWV GIIDIDGSTYYASWAKGRFTISRDNSKNTLYLQMNSLRAEDTAVYYCA RDRFVGVDIFDPWGQGTLVTVSS | 56 |
| 11041gH12 V-region | EVQLVESGGGLVQPGGSLRLSCAVSGFSLSSYAMIWVRQAPGKGLEWI SIIDIDGSTYYASWAKGRFTISRDNSKNTLYLQMNSLRAEDTAVYYCA RDRFVGVDIFDPWGQGTLVTVSS | 57 |
| 11041 gH8 D54E V-region (gH15) | EVQLVESGGGLVQPGGSLRLSCAVSGFSLSSYAMIWVRQAPGKGLEWI GIIDIEGSTYYASWAKGRFTISRDSSKNTLYLQMNSLRAEDTAVYYCA RDRFVGVDIFDPWGQGTLVTVSS | 58 |
| 11041 gH11 D54E V-region (gH17) | EVQLVESGGGLVQPGGSLRLSCAVSGFSLSSYAMIWVRQAPGKGLEWV GIIDIEGSTYYASWAKGRFTISRDNSKNTLYLQMNSLRAEDTAVYYCA RDRFVGVDIFDPWGQGTLVTVSS | 59 |
| 11041 gH12 D54E V-region (gH18) | EVQLVESGGGLVQPGGSLRLSCAVSGFSLSSYAMIWVRQAPGKGLEWI SIIDIEGSTYYASWAKGRFTISRDNSKNTLYLQMNSLRAEDTAVYYCA RDRFVGVDIFDPWGQGTLVTVSS | 60 |

TABLE 9-continued

Sequences of the 11041 antibody and related variants

| Name | Sequence | SEQ ID NO |
|---|---|---|
| 11041 gL6 C91S S96A V-region (gL13) | Same as SEQ ID NO: 22 | 22 |
| 11041 gH5 D54E V-region (gH14) | Same as SEQ ID NO: 24 | 24 |
| Human IGKV1D-13 IGKJ4 acceptor framework | AIQLTQSPSSLSASVGDRVTITCRASQGISSALAWYQQKPGKAPKLLI YDASSLESGVPSRFSGSGSGTDFTLTISSLQPEDFATYYCQQFNSYPL TFGGGTKVEIK | 61 |
| Human IGKV1D-13 IGKJ4 acceptor framework | gccatccagttgacccagtctccatcctccctgtctgcatctgtagga gacagagtcaccatcacttgccgggcaagtcagggcattagcagtgct ttagcctggtatcagcagaaaccagggaaagctcctaagctcctgatc tatgatgcctccagtttggaaagtggggtcccatcaaggttcagcggc agtggatctgggacagatttcactctcaccatcagcagcctgcagcct gaagattttgcaacttattactgtcaacagtttaatagttaccctctc actttcggcggagggaccaaggtggagatcaaa | 62 |
| Human IGHV3-66 IGHJ4 acceptor framework | EVQLVESGGGLVQPGGSLRLSCAASGFTVSSNYMSWVRQAPGKGLEWV SVIYSGGSTYYADSVKGRFTISRDNSKNTLYLQMNSLRAEDTAVYYCA RYFDYWGQGTLVTVSS | 63 |
| Human IGHV3-66 IGHJ4 acceptor framework | gaggtgcagctggtggagtctggggggggcttggtccagcctggggggg tccctgagactctcctgtgcagcctctggattcaccgtcagtagcaac tacatgagctgggtccgccaggctccagggaagggggctggagtgggtc tcagttatttatagcggtggtagcacatactacgcagactccgtgaag ggcagattcaccatctccagagacaattccaagaacacgctgtatctt caaatgaacagcctgagagccgaggacacggctgtgtattactgtgcg agatactttgactactgggggccaaggaaccctggtcaccgtctcctca | 64 |

TABLE 9

Sequences of the 11070 antibody and related variants

| Name | Sequence | SEQ ID NO |
|---|---|---|
| 11070 CDRL1 | KASKTISKYLA | 65 |
| 11070 CDRL2 | SGSTLQS | 66 |
| 11070 CDRL3 | QQHNEYPLT | 67 |
| 11070 CDRH1 | GFSLTSYSVH | 68 |
| 11070 CDRH2 | RMWSDGDTSYNTAFTS | 69 |
| 11070 CDRH3 | SLDFYYDTTLAF | 70 |
| 11070 CDRH2 (not mutated) | RMWSDGDTSYNSAFTS | 71 |
| 11070 CDRH2 S61T | Same as SEQ ID NO: 69 | 69 |
| 11070gL7 V-region | DIQMTQSPSSVSASVGDRVTITCKASKTISKYLAWYQQKPGKAN KLLIYSGSTLQSGVPSRESGSGSGTDFTLTISSLQPEDFATYYC QQHNEYPLTFGQGTKLEIK | 72 |
| 11070gL7 V-region | gacattcagatgactcagtcgccttcgtccgtgagcgccagcgt cggagacagagtgacaatcacctgtaaagcgtccaagaccatct ccaagtacctggcttggtatcagcagaaaccgggggaaggccaac aagttgcttatctactccggttctactctccaatcgggagtgcc aagccggttttccgggtccggatcaggcaccgacttcaccctca ccatctcatccctgcaaccggaggatttcgccacgtactactgc cagcagcacaacgaataccccctgaccttcggccaaggaactaa gctggaaattaag | 73 |
| 11070gH16 V-region | EVQLQESGPGLVKPSQTLSLTCTVSGFSLTSYSVHWVRQHPGKG LEWIGRMWSDGDTSYNTAFTSRLTISRDTSKNQVSLKLSSVTAA DTAVYYCARSLDFYYDTTLAFWGQGTTVTVSS | 74 |

TABLE 9-continued

Sequences of the 11070 antibody and related variants

| Name | Sequence | SEQ ID NO |
|------|----------|-----------|
| 11070gH16 V-region | gaggtgcagctgcaagaatccggtcctggcctcgtgaagccgtc gcagaccttgagcctgacctgtactgtgtccggattcagcctca catcctactcggtgcactgggtcagacagcatcccggaaaaggc ctggaatggattgggaggatgtggtctgatggagacacctcct a caacacggcgttcaccagccggctgaccatctcccgcgacacct ccaagaaccaagtgtcgcttaagctgtcctcagtcactgccgcc gataccgcagtgtattactgcgctcggtcactggactttacta cgacaccaccctggccttctggggacaggggactactgtgactg tctcgagc | 75 |
| 11070gL7 Light chain | DIQMTQSPSSVSASVGDRVTITCKASKTISKYLAWYQQKPGKAN KLLIYSGSTLQSGVPSRFSGSGSGTDFTLTISSLQPEDFATYYC QQHNEYPLTFGQGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSENRGEC | 76 |
| 11070gL7 Light chain | gacattcagatgactcagtcgccttcgtccgtgagcgccagcgt cggagacagagtgacaatcacctgtaaagcgtccaagaccatct ccaagtacctggcttggtatcagcagaaaccggggaaggccaac aagttgcttatctactccggttctactctccaatcgggagtgcc aagccggtttccgggtccggatcaggcaccgacttcaccctca ccatctcatccctgcaaccggaggatttcgccacgtactactgc cagcagcacaacgaatacccctgaccttcggcaaggaactaa gctggaaattaagcgtacggtggccgctcctccgtgttcatct tcccaccctccgacgagcagctgaagtccggcaccgcctccgtc gtgtgcctgctgaacaacttctaccccgcgaggccaaggtgca gtggaaggtggacaacgccctgcagtccggcaactcccaggaat ccgtcaccgagcaggactccaaggacagcacctactccctgtcc tccaccctgaccctgtccaaggccgactacgagaagcacaaggt gtacgcctgcgaagtgacccaccagggcctgtccagccccgtga ccaagtccttcaaccggggcgagtgc | 77 |
| 11070gH16 Fab Heavy chain | EVQLQESGPGLVKPSQTLSLTCTVSGFSLTSYSVHWVRQHPGKG LEWIGRMWSDGDTSYNTAFTSRLTISRDTSKNQVSLKLSSVTAA DTAVYYCARSLDFYYDTTLAFWGQGTTVTVSSASTKGPSVEPLA PSSKSTSGGTAALGCLVKDYFPEPVTVSWNSGALTSGVHTEPAV LQSSGLYSLSSVVTVPSSSLGTQTYICNVNHKPSNTKVDKKVEP KSC | 78 |
| 11070gH16 Fab Heavy chain | gaggtgcagctgcaagaatccggtcctggcctcgtgaagccgtc gcagaccttgagcctgacctgtactgtgtccggattcagcctca catcctactcggtgcactgggtcagacagcatcccggaaaaggc ctggaatggattgggaggatgtggtctgatggagacacctcct a caacacggcgttcaccagccggctgaccatctcccgcgacacct ccaagaaccaagtgtcgcttaagctgtcctcagtcactgccgcc gataccgcagtgtattactgcgctcggtcactggactttacta cgacaccaccctggccttctggggacaggggactactgtgactg tctcgagcgcgtccacaaagggcccatcggtcttcccccctggca ccctcctccaagagcacctctgggggcacagcggccctgggctg cctggtcaaggactacttccccgaaccagtgacggtgtcgtgga actcaggtgccctgaccagcggcgttcacaccttcccggctgtc ctacagtcttcaggactctactccctgagcagcgtggtgaccgt gccctccagcagcttgggcacccagacctacatctgcaacgtga atcacaagcccagcaacaccaaggtcgataagaaagttgagccc aaatcttgt | 79 |
| 11070gH16 IgG1 Heavy chain | EVQLQESGPGLVKPSQTLSLTCTVSGFSLTSYSVHWVRQHPGKG LEWIGRMWSDGDTSYNTAFTSRLTISRDTSKNQVSLKLSSVTAA DTAVYYCARSLDFYYDTTLAFWGQGTTVTVSSASTKGPSVEPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVY TLPPSRDELTKNQVSLTCLVKGFYPSDIAVEWESNGQPENNYKT TPPVLDSDGSFFLYSKLTVDKSRWQQGNVFSCSVMHEALHNHYT QKSLSLSPGK | 80 |
| 11070gH16 IgG1 Heavy chain | gaggtgcagctgcaagaatccggtcctggcctcgtgaagccgtc gcagaccttgagcctgacctgtactgtgtccggattcagcctca catcctactcggtgcactgggtcagacagcatcccggaaaaggc ctggaatggattgggaggatgtggtctgatggagacacctcct a caacacggcgttcaccagccggctgaccatctcccgcgacacct ccaagaaccaagtgtcgcttaagctgtcctcagtcactgccgcc gataccgcagtgtattactgcgctcggtcactggactttacta cgacaccaccctggccttctggggacaggggactactgtgactg | 81 |

TABLE 9-continued

| Sequences of the 11070 antibody and related variants | | |
|---|---|---|
| Name | Sequence | SEQ ID NO |

|  | tctcgagcgcttctacaaagggcccatcggtcttccccctggca<br>ccctcctccaagagcacctctggggggcacagcggccctgggctg<br>cctggtcaaggactacttccccgaaccggtgacggtgtcgtgga<br>actcaggcgccctgaccagcggcgtgcacaccttcccggctgtc<br>ctacagtcctcaggactctactccctcagcagcgtggtgaccgt<br>gccctccagcagcttgggcacccagacctacatctgcaacgtga<br>atcacaagcccagcaacaccaaggtggacaagaaagttgagccc<br>aaatcttgtgacaaaactcacacatgcccaccgtgcccagcacc<br>tgaactcctggggggaccgtcagtcttcctcttccccccaaaac<br>ccaaggacaccctcatgatctcccggacccctgaggtcacatgc<br>gtggtggtggacgtgagccacgaagaccctgaggtcaagttcaa<br>ctggtacgtggacggcgtggaggtgcataatgccaagacaaagc<br>cgcgggaggagcagtacaacagcacgtaccgtgtggtcagcgtc<br>ctcaccgtcctgcaccaggactggctgaatggcaaggagtacaa<br>gtgcaaggtctccaacaaagccctcccagcccccatcgagaaaa<br>ccatctccaaagccaaagggcagccccgagaaccacaggtgtac<br>accctgcccccatcccgggatgagctgaccaagaaccaggtcag<br>cctgacctgcctggtcaaaggcttctatcccagcgacatcgccg<br>tggagtgggagagcaatgggcagccggagaacaactacaagacc<br>acgcctcccgtgctggactccgacggctccttcttcctctacag<br>caagctcaccgtggacaagagcaggtggcagcaggggaacgtct<br>tctcatgctccgtgatgcatgaggctctgcacaaccactacacg<br>cagaagagcctctccctgtctccgggtaaa |  |
| 11070gH16 IgG4P<br>Heavy chain | EVQLQESGPGLVKPSQTLSLTCTVSGFSLTSYSVHWVRQHPGKG<br>LEWIGRMWSDGDTSYNTAFTSRLTISRDTSKNQVSLKLSSVTAA<br>DTAVYYCARSLDFYYDTTLAFWGQGTTVTVSSASTKGPSVEPLA<br>PCSRSTSESTAALGCLVKDYFPEPVTVSWNSGALTSGVHTFPAV<br>LQSSGLYSLSSVVTVPSSSLGTKTYTCNVDHKPSNTKVDKRVES<br>KYGPPCPPCPAPEFLGGPSVFLFPPKPKDTLMISRTPEVTCVVV<br>DVSQEDPEVQFNWYVDGVEVHNAKTKPREEQFNSTYRVVSVLTV<br>LHQDWLNGKEYKCKVSNKGLPSSIEKTISKAKGQPREPQVYTLP<br>PSQEEMTKNQVSLTCLVKGFYPSDIAVEWESNGQPENNYKTTPP<br>VLDSDGSFFLYSRLTVDKSRWQEGNVFSCSVMHEALHNHYTQKS<br>LSLSLGK | 82 |
| 11070gH16 IgG4P<br>Heavy chain | gaggtgcagctgcaagaatccggtcctggcctcgtgaagccgtc<br>gcagaccttgagcctgacctgtactgtgtccggattcagcctca<br>catcctactcggtgcactgggtcagacagcatcccggaaaaggc<br>ctggaatggattgggaggatgtggtctgatggagacacctccta<br>caacacggcgttcaccagccggctgaccatctcccgcgacacct<br>ccaagaaccaagtgtcgcttaagctgtcctcagtcactgccgcc<br>gataccgcagtgtattactgcgcgctcggtcactggactttacta<br>cgacaccaccctggccttctggggacaggggactactgtgactg<br>tctcgagcgcttctacaaagggcccctccgtgttcctctggcc<br>ccttgctcccggtccacctccgagtctaccgccgctctgggctg<br>cctggtcaaggactacttccccgagcccgtgacagtgtcctgga<br>actctggcgccctgacctccggcgtgcacaccttccctgccgtg<br>ctgcagtcctccggcctgtactccctgtcctccgtcgtgaccgt<br>gccctcctccagcctgggcaccaagacctacacctgtaacgtgg<br>accacaagccctccaacaccaaggtggacaagcgggtggaatct<br>aagtacggccctccctgccccccctgccctgccctgaatttct<br>gggcggaccttccgtgttcctgttcccccccaaagcccaaggaca<br>ccctgatgatctcccggacccccgaagtgacctgcgtggtggtg<br>gacgtgtcccaggaagatcccgaggtccagttcaattggtacgt<br>ggacggcgtggaagtgcacaatgccaagaccaagcccagagagg<br>aacagttcaactccacctaccgggtggtgtccgtgctgaccgtg<br>ctgcaccaggactggctgaacggcaaagagtacaagtgcaaggt<br>gtccaacaagggcctgcctccagcatcgaaaagaccatctcca<br>aggccaagggccagccccgcgagccccaggtgtacaccctgccc<br>cctagccaggaagagatgaccaagaaccaggtgtccctgacctg<br>tctggtcaagggcttctaccctccgacattgccgtggaatggg<br>agtccaacggccagcccgagaacaactacaagaccacccccct<br>gtgctggacagcgacggctccttcttcctgtactctcggctgac<br>cgtgtacaagtcccggtggcaggaaggcaacgtcttctcctgct<br>ccgtgatgcacgaggccctgcacaaccactacacccagaagtcc<br>ctgtccctgagcctgggcaag | 83 |
| Rat Ab 11070<br>VL-region | DIVMTQTPSNLAASPGESVSINCKASKTISKYLAWYQQKPGKAN<br>KLLIYSGSTLQSGTPSRESGSGSSTDETLTIRNLEPEDFGLYYC<br>QQHNEYPLTFGSGTKLEIK | 84 |
| Rat Ab 11070<br>VL-region | gatattgtgatgacacagactccatctaatcttgctgcctctcc<br>tggagaaagtgtttccatcaattgcaaggcaagtaagaccatta<br>gcaagtatttagcctggtatcaacagaaacctgggaaagcaaat<br>aagcttcttatctattctgggtcaactttgcaatctggaactcc | 85 |

TABLE 9-continued

| Sequences of the 11070 antibody and related variants | | |
| --- | --- | --- |
| Name | Sequence | SEQ ID NO |
| | atcgaggttcagtggcagtggatctagtacagatttcactctca ccatcagaaacctggagcctgaagattttggactctattactgt caacagcataatgaatacccgctcacgttcggttctgggaccaa gttggaaataaaa | |
| Rat Ab 11070 VH-region | EVQLQESGPGLVQPSQTLSPTCTVSGFSLTSYSVHWVRQHSGKS LEWMGRMWSDGDTSYNSAFTSRLSITRDTSKSQVELKMNSLQTE DTGTYYCARSLDFYYDTTLAFWGPGTTVTVSS | 86 |
| Rat Ab 11070 VH-region | gaggtgcagctgcaggagtcaggacctgggctggtgcagccctc acagaccctgtcccccacctgcactgtctctgggttctcactaa ctagttacagtgtacactgggttcgccagcattcaggaaagagt ctggaatggatgggaagaatgtggagtgatggagacacatcata taattcagcgttcacatcccgattgagcatcactagggacacct ccaagagccaagttttcttaaaaatgaacagtctgcaaactgaa gacacaggcacttactactgtgccagaagtctcgattttttacta tgatactactcttgccttctggggggcccaggaaccacggtcaccg tctcgagt | 87 |
| 11070gL1 V-region | DIVMTQSPSSVSASVGDRVTITCKASKTISKYLAWYQQKPGKAN KLLIYSGSTLQSGTPSRESGSGSSTDETLTISSLQPEDFATYYC QQHNEYPLTFGQGTKLEIK | 88 |
| 11070gH1 V-region | EVQLQESGPGLVKPSQTLSLTCTVSGFSLTSYSVHWVRQHSGKG LEWMGRMWSDGDTSYNSAFTSRLTISRDTSKSQVSLKLSSVTAA DTAVYYCARSLDFYYDTTLAFWGQGTTVTVSS | 89 |
| 11070gH13 V-region (gH1 S61T) | EVQLQESGPGLVKPSQTLSLTCTVSGFSLTSYSVHWVRQHSGKG LEWMGRMWSDGDTSYNTAFTSRLTISRDTSKSQVSLKLSSVTAA DTAVYYCARSLDFYYDTTLAFWGQGTTVTVSS | 90 |
| Human IGKV1-12 IGKJ2 acceptor framework | DIQMTQSPSSVSASVGDRVTITCRASQGISSWLAWYQQKPGKAP KLLIYAASSLQSGVPSRESGSGSGTDFTLTISSLQPEDFATYYC QQANSFPYTFGQGTKLEIK | 91 |
| Human IGKV1-12 IGKJ2 acceptor framework | gacatccagatgacccagtctccatcttccgtgtctgcatctgt aggagacagagtcaccatcacttgtcgggcgagtcagggtatta gcagctggttagcctggtatcagcagaaaccagggaaagccct aagctcctgatctatgctgcatccagtttgcaaagtggggtccc atcaaggttcagcggcagtggatctgggacagatttcactctca ccatcagcagcctgcagcctgaagattttgcaacttactattgt caacaggctaacagtttcccttacacttttggccaggggaccaa gctggagatcaaa | 92 |
| Human IGHV4-31 IGHJ6 acceptor framework | QVQLQESGPGLVKPSQTLSLTCTVSGGSISSGGYYWSWIRQHPG KGLEWIGYIYYSGSTYYNPSLKSRVTISVDTSKNQFSLKLSSVT AADTAVYYCARYYYYYGMDVWGQGTTVTVSS | 93 |
| Human IGHV4-31 IGHJ6 acceptor framework | caggtgcagctgcaggagtcgggcccaggactggtgaagccttc acagaccctgtccctcacctgcactgtctctggtggctccatca gcagtggtggttactactggagctggatccgccagcacccaggg aagggcctggagtggattgggtacatctattacagtgggagcac ctactacaacccgtccctcaagagtcgagttaccatatcagtag acacgtctaagaaccagttctccctgaagctgagctctgtgact gccgcggacacggccgtgtattactgtgcgagatactactacta ctacggtatggacgtctgggggcaagggaccacggtcaccgtct cctca | 94 |

EXAMPLES

Example 1. Generation and Selection of Therapeutic Anti-IL22 Antibodies 11041 and 11070

A number of animals across different species (including mice, rats and rabbits) were immunized with either, purified in-house produced or commercially available human IL22 (R&D systems). Following 3-5 shots, the animals were sacrificed and PBMC, spleen, bone marrow and lymph nodes harvested. Sera was monitored for binding to human and cynomolgus IL22 in ELISA.

In the case of 11041, memory B cell cultures were set up and supernatants were first screened for their ability to bind human and cynomolgus IL22 in a bead-based assay on the TTP Labtech Mirrorball system. This was a homogeneous multiplex assay using biotinylated human IL22 and biotinylated cynomolgus IL22 coated onto Sol-R streptavidin beads (TTP Labtech) and a goat anti-rabbit Fc-FITC conjugate as a reveal agent.

Approx. 4500 IL22-specific positive hits were identified in the primary Mirrorball screens from a total of 12×(164-400)-plate B culture experiments. Positive supernatants from this assay were then progressed for further characterization by:

ELISA, to confirm binding to human and cynomolgus monkey IL-22, progression into an IL22 dependent HACAT phospho STAT3 HTRF cell assay (CisBio) to identify neutralizers and, profiling in BIAcore to estimate off-rate and to characterize the mode of action of neutralization.

Neutralization was categorized as either bin 1 or bin 2. Bin 1 represents an antibody that binds to human IL22 and prevents binding of IL22R1. Bin 2 represents an antibody that binds human IL22 but allows IL22R1 binding. We were selecting antibodies that operated via bin 1. Wells demonstrating neutralization in the phospho STAT3 HTRF assay and/or wells with desirable BIAcore profiles were progressed for V region recovery using the fluorescent foci method.

Plasma cells from bone marrow were also directly screened for their ability to bind human IL22 using the fluorescent foci method (relevant for 11070). Here, B cells secreting IL22 specific antibodies were picked on biotinylated human IL22 immobilized on streptavidin beads response units (RUs). HBS-EP+ buffer (10 mM HEPES pH 7.4, 0.15 M NaCl, 3 mM EDTA, 0.05% Surfactant P20, GE Healthcare) was used as the running buffer with a flow rate of 10 μL/min. A 10 μL injection of 11041 Fab at 0.5 μg/mL was used for capture by the immobilized Goat Anti-Rabbit Fab. Human IL22, Cyno IL22 and mouse IL22 were titrated over the captured 11041 Fab (at 0 nM, 0.6 nM, 1.8 nM, 5.5 nM, 16.6 nM and 50 nM) at a flow rate of 30 μL/min to assess affinity. Blocking of human IL22R1 was assessed by injecting 100 nM IL-22 (for 180 seconds at 30 μL/min) followed by injecting human IL22R1 (at 50 nM for 180 s).

The surface was generated by 2×10 μL injection of 50 mM HCl, interspersed by a 10 μL injection of 5 mM NaOH at flowrate of 10 μL/min. Background subtraction binding curves were analyzed using the Biacore T200 evaluation software following standard procedures. Kinetic parameters were determined from the fitting algorithm. The kinetic parameters of purified 11041 binding to human, cynomolgus and mouse IL22 are shown in Table 11.

TABLE 11

| Kinetic parameters of rabbit 11041 binding to human, cynomolgus and mouse IL22 | | | | | | | | |
|---|---|---|---|---|---|---|---|---|
| Human IL22 | | | Cynomolgus IL22 | | | Mouse IL22 | | |
| ka (1/Ms) | kd (1/s) | KD (M) | ka (1/Ms) | kd (1/s) | KD (M) | ka (1/Ms) | kd (1/s) | KD (M) |
| 8.70E+05 | 2.90E−04 | 3.40E−10 | 2.60E+05 | 2.80E−04 | 1.10E−09 | 3.70E+07 | 1.10E−01 | 3.00E−09 | using a goat anti-rat Fc-FITC conjugate reveal reagent. Approx. 300 direct foci were picked.

Following reverse transcription (RT) and PCR of the picked cells, 'transcriptionally active PCR' (TAP) products encoding the antibodies' V regions were generated and used to transiently transfect HEK-293 cells. The resultant TAP supernatants, containing recombinant antibody, were tested for their ability to; bind human and cynomolgus IL22, block IL22R1 binding in the BIAcore and neutralize IL22 in the HACAT phospho STAT3 HTRF cell assay.

Heavy and light chain variable region gene pairs from interesting TAP products were then cloned as either rabbit or mouse Fab antibodies and re-expressed in a HEK-293 transient expression system. In total 131 V regions were cloned and sequenced. Recombinant cloned antibodies were then retested for their ability to bind human and cynomolgus IL22, block IL22R1 binding in the BIAcore and neutralize IL22 dependent IL-10 release in the COLO205 IL-10 HTRF cell-based assay (CisBio). Following this characterization, 2 antibodies fulfilled the criteria i.e. rabbit derived 11041 and rat derived 11070.

Based on neutralization potency, affinity to both human and cynomolgus IL22, donor content in humanized grafts (see below) and expression data, rabbit derived 11041 was selected for further progression.

Example 2. Binding of Rabbit 11041 to Human, Cynomolgus, and Mouse IL22

The affinity of purified 11041 rabbit Fab to human, cynomolgus and mouse IL22 was assessed using a Biacore T200 instrument (GE Healthcare) by capturing the rabbit 11041 Fab to an immobilized anti rabbit IgG F(ab')₂ followed by titration of IL22 from each species. Affinipure Goat anti-Rabbit IgG-F(ab')₂ fragment specific (Jackson ImmunoResearch) was immobilized on a CM5 Sensor Chip via amine coupling chemistry to a capture level of ~5000

Example 3. Humanization of 11041

Antibody 11041 was humanized by grafting the CDRs from the rabbit V-region onto human germline antibody V-region frameworks. In order to recover the activity of the antibody, a number of framework residues from the rabbit V-region were also retained in the humanized sequence. These residues were selected using the protocol outlined by Adair et al. (1991) (WO91/09967). Alignments of the rabbit antibody (donor) V-region sequences with the human germline (acceptor) V-region sequences are shown in FIGS. 1 and 2, together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., WO91/09967).

Human V-region IGKV1D-13 plus IGKJ4 J-region (IMGT, www.imgt.org/) was chosen as the acceptor for antibody 11041 light chain CDRs. The light chain framework residues in the humanized graft variants are all from the human germline gene, with the exception of none, one or two residues from the group comprising residues 2 and 3 (with reference to SEQ ID NO:38 gL1), where the donor residues Valine (V2) and Valine (V3) were retained, respectively. In some humanized graft variants, an unpaired/free Cysteine residue at position 91 in CDRL3 was removed by mutation to either Valine (C91V) or Serine (C91S): free cysteine residues can be subject to post-translational modification, such as cysteinylation, and may contribute to covalent aggregation and poor stability. Mutation of this residue resulted in an unexpected 15- to 50-fold increase in binding affinity, respectively, as measured by surface plasmon resonance (Table 12, gL1gH1 (642 pM) compared to gL1 (C91V)gH1 (41.9 pM) or gL1(C91S)gH1 (12.4 pM)). In some humanized graft variants, a potential Asparagine deamidation site in CDRL3 was modified by either replacing the Asparagine residue at position 95 with Aspartic acid (N95D) or by replacing the Serine residue at position 96 with Alanine (S96A). Modification of the deamidation site by S96A mutation significantly reduced the basal level of deamidation.

Human V-region IGHV3-66 plus IGHJ4 J-region (IMGT, www.imgt.org/) was chosen as the acceptor for the heavy chain CDRs of antibody 11041. In common with many rabbit antibodies, the VH gene of antibody 11041 is shorter than the selected human acceptor. When aligned with the human acceptor sequence, framework 1 of the VH region of antibody 11041 lacks the N-terminal residue, which is retained in the humanized antibody (FIG. 2). Framework 3 of the 11041 rabbit VH region also lacks two residues (75 and 76, with reference to SEQ ID NO:49 gH1) in the loop between beta sheet strands D and E: in the humanized graft variants the gap is filled with the corresponding residues (Lysine 75, K75; Asparagine 76, N76) from the selected human acceptor sequence (FIG. 2). The heavy chain framework residues in the humanized graft variants are all from the human germline gene, with the exception of the residues 24, 48, 49, 73 and 78 (with reference to SEQ ID NO: 49 gH1), where the donor residues Valine (V24), Isoleucine (I48), Glycine (G49), Serine (S73) and Valine (V78) were retained, respectively. Retention of donor residues V24, I48, G49 and V78 was essential for the highest affinity binding to human IL-22, as measured by surface plasmon resonance. In some humanized graft variants, a potential Aspartic acid isomerization site in CDRH2 was modified by either replacing the Aspartic acid residue at position 54 with Glutamic acid (D54E), or by replacing the Glycine residue at position 55 with Alanine (G55A). In some humanized graft variants, a potential hydrolysis site in CDRH3 was modified by replacing the Aspartic acid residue at position 107 with glutamic acid (D107E).

TABLE 12

| Binding affinity of different generated variants of 11041 antibody | | | | | |
|---|---|---|---|---|---|
| Antibody variant | Light chain Donor residues | Light chain Mutation | Heavy chain Donor residues | Heavy chain Mutation | Affinity (KD) pM |
| 11041 (parental) | — | | — | | 569 |
| 11041gL1gH1 | V2, V3 | | V24, I48, G49, S73, V78 | | 642 |
| 11041gL1 C91S gH1 | V2, V3 | C91S | V24, I48, G49, S73, V78 | | 12.4 |
| 11041gL1 C91V gH1 | V2, V3 | C91V | V24, I48, G49, S73, V78 | | 41.9 |
| 11041gL1 N95D gH1 | V2, V3 | N95D | V24, I48, G49, S73, V78 | | 128.6 |
| 11041gL1 S96A gH1 | V2, V3 | S96A | V24, I48, G49, S73, V78 | | 200 |
| 11041gL6gH1 | V2 | | V24, I48, G49, S73, V78 | | 369 |
| 11041gL7gH1 | — | | V24, I48, G49, S73, V78 | | 446 |
| 11041gL1gH1 G55A | V2, V3 | | V24, I48, G49, S73, V78 | G55A | 627 |
| 11041gL1gH1 D54E | V2, V3 | | V24, I48, G49, S73, V78 | D54E | 166 |
| 11041gL1gH1 D107E | V2, V3 | | V24, I48, G49, S73, V78 | D107E | 657 |
| 11041gL1gH5 | V2, V3 | | V24, I48, G49, V78 | | 378 |
| 11041gL1gH8 | V2, V3 | | V24, I48, G49, S73 | | 274 |
| 11041gL1 C91S gH1 D54E | V2, V3 | C91S | V24, I48, G49, S73, V78 | D54E | 28.1 |
| 11041gL1 S96A gH1 D54E | V2, V3 | | V24, I48, G49, S73, V78 | D54E | 88.8 |
| 11041gL1 C91S gH9 | V2, V3 | C91S | I48, G49, S73, V78 | | 11.4 |
| 11041gL1 C91S S96A gH5 D54E | V2, V3 | C91S, S96A | V24, I48, G49, V78 | D54E | 23.3 |
| 11041gL1 C91S S96AgH15 | V2, V3 | C91S, S96A | V24, I48, G49, S73 | D54E | 79 |
| 11041gL1 C91S S96AgH17 | V2, V3 | C91S, S96A | V24, G49 | D54E | 39.8 |
| 11041gL1 C91S S96AgH18 | V2, V3 | C91S, S96A | V24, I48 | D54E | 45.4 |
| 11041gL6 C91S gH5 D54E | V2 | C91S | V24, I48, G49, V78 | D54E | 16.1 |
| 11041gL6 C91S gH8 D54E | V2 | C91S | V24, I48, G49, S73 | D54E | 105.8 |
| 11041gL6 C91S gH11 D54E | V2 | C91S | V24, G49 | D54E | 51.6 |
| 11041gL6 C91S gH12 D54E | V2 | C91S | V24, I48 | D54E | 44.4 |
| 11041gL7 C91S gH5 D54E | — | C91S | V24, I48, G49, V78 | D54E | 29.3 |
| 11041gL7 C91S gH8 D54E | — | C91S | V24, I48, G49, S73 | D54E | 114.6 |
| 11041gL7 C91S gH11 D54E | — | C91S | V24, G49 | D54E | 66.6 |
| 11041gL7 C91S gH12 D54E | — | C91S | V24, I48 | D54E | 73.9 |
| 11041gL6 C91S S96A gH5 D54E | V2 | C91S, S96A | V24, I48, G49, V78 | D54E | 12.5 |
| 11041gL6 C91S S96A gH8 D54E | V2 | C91S, S96A | V24, I48, G49, S73 | D54E | 84.9 |
| 11041gL6 C91S S96A gH11 D54E | V2 | C91S, S96A | V24, G49 | D54E | 52.4 |
| 11041gL6 C91S S96A gH12 D54E | V2 | C91S, S96A | V24, I48 | D54E | 51.7 |
| 11041gL7 C91S S96A gH5 D54E | — | C91S, S96A | V24, I48, G49, V78 | D54E | 26.6 |

TABLE 12-continued

| | Light chain Donor residues | Light chain Mutation | Heavy chain Donor residues | Heavy chain Mutation | Affinity (KD) pM |
|---|---|---|---|---|---|
| Antibody variant | | | | | |
| 11041gL7 C91S S96A gH8 D54E | — | C91S, S96A | V24, I48, G49, S73 | D54E | 103.8 |
| 11041gL7 C91S S96A gH11 D54E | — | C91S, S96A | V24, G49 | D54E | 61.7 |
| 11041gL7 C91S S96A gH12 D54E | — | C91S, S96A | V24, I48 | D54E | 67.6 |

*Binding affinity of different generated variants of 11041 antibody*

Example 4. Humanization of 11070

Antibody 11070 was humanized by grafting the CDRs from the rat V-region onto human germline antibody V-region frameworks. In order to recover the activity of the antibody, a number of framework residues from the rat V-region were also retained in the humanized sequence. These residues were selected using the protocol outlined by Adair et al. (1991) (WO91/09967). Alignments of the rat antibody (donor) V-region sequences with the human germline (acceptor) V-region sequences are shown in FIGS. 3A and 3B, together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., WO91/09967).

Human V-region IGKV1-12 plus IGKJ2 J-region (IMGT, www.imgt.org/) was chosen as the acceptor for antibody 11070 light chain CDRs. The light chain framework residues in the humanized graft variants are all from the human germline gene, with the exception of one or more residues from the group comprising residues 3, 44, 58 and 68 (with reference to SEQ ID NO:88 gL1), where the donor residues Valine (V3), Asparagine (N44), Threonine (T58) and Serine (S68) were retained, respectively. Retention of donor residue N44 was essential for the highest affinity binding to human IL-22, as measured by surface plasmon resonance (Table 13).

Human V-region IGHV4-31 plus IGHJ6 J-region (IMGT, www.imgt.org/) was chosen as the acceptor for the heavy chain CDRs of antibody 11070. The heavy chain framework residues in the humanized graft variants are all from the human germline gene, with the exception of one or more residues from the group comprising residues 37, 41, 48, 67, 71, 76 and 78 (with reference to SEQ ID NO: 89 gH1), where the donor residues Valine (V37), Serine (S41), Methionine (M48), Leucine (L67), Arginine (R71), Serine (S76) and Valine (V78) were retained, respectively. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. Retention of donor residues V37, L67, R71 and V78 was essential for the highest affinity binding to human IL-22, as measured by surface plasmon resonance (Table 13). In some humanized graft variants, a potential Asparagine deamidation site in CDRH2 was modified by replacing the Serine residue at position 61 with Threonine (S61T).

TABLE 13

*Binding affinity of different generated variants of 11070 antibody*

| Antibody 11070 variant | Light chain Donor residues | Heavy chain Donor residues | Heavy chain Mutation | Affinity (KD) pM |
|---|---|---|---|---|
| 11070 | — | — | — | 49 |
| 11070gL1gH1 | V3, N44, T58, S68 | E1, V37, S41, M48, L67, R71, S76, V78 | — | 36.8 |
| 11070gL1gH13 | V3, N44, T58, S68 | E1, V37, S41, M48, L67, R71, S76, V78 | S61T | 31.7 |
| 11070gL7gH16 | N44 | E1, V37, L67, R71, V78 | S61T | 25.7 |

Example 5. Cloning and Production of Variants

Genes encoding different variants of heavy and light chain V-region sequences were designed and constructed by an automated synthesis approach by ATUM (Newark, CA). Further variants of heavy and light chain V-regions were created by modifying the VH and VK genes by oligonucleotide-directed mutagenesis, including, in some cases, mutations within CDRs. For transient expression in mammalian cells, the humanized light chain V-region genes were cloned into the UCB light chain expression vector pMhCK, which contains DNA encoding the human Kappa chain constant region (Km3 allotype). The humanized heavy chain V-region genes were cloned into the UCB human gamma-1 Fab heavy chain expression vector pMhFabnh, which contains DNA encoding the human gamma-1 CH1-hinge domain. Co-transfection of the resulting heavy and light chain vectors into Expi293™ suspension cells gave expression of the humanized, recombinant antibodies in the human Fab format. The variant humanized Fab antibodies were assessed for their binding affinity for human IL-22 relative to the parent antibody, their potency in in vitro assays, their biophysical properties and suitability for downstream processing.

Example 6. Binding Properties of Humanized 11041 Antibody

Humanized samples for 11041 antibody were tested by capturing the samples on immobilized anti human IgG-F (ab')₂ then titration of Human IL22 over the captured surface. The assay was run on Biacore 8K instrument (GE Healthcare) and BIA (Biomolecular Interaction Analysis) was performed using Biacore 8000 evaluation software. Affinpure Goat anti-human IgG-F(ab')₂ fragment specific (Jackson ImmunoResearch) was immobilized on a CM5 Sensor Chip via amine coupling chemistry to a capture level of ~5000 response units (RUs). HBS-EP+ buffer (10 mM HEPES pH 7.4, 0.15 M NaCl, 3 mM EDTA, 0.05% Surfactant P20, GE Healthcare) was used as the running buffer with a flow rate of 10 µL/min. A 10 µL injection of humanized samples of 11041 antibody at 0.5 µg/mL was used for capture by the immobilized Goat anti-human Fab IgG. Human IL22 (50 nM, 16.7 nM, 5.6 nM, 1.9 nM and 617 pM) and were titrated over the captured 11041 antibodies at a flow rate of 30 µL/min.

control samples. A positive response for the IL-22R1 would indicate that 11041 antibody binds to a different epitope from IL-22R1. A lack of response for the IL-22R1 would indicate that the binding site of 11041 antibody on IL-22 overlaps with IL-22R1 binding site. After each cycle the surface was regenerated by the following injections: 60s 50 mM HCl, 60 s 5 mM NaOH and 60 s HCl, all at 10 µL min−1.

As shown in Table 15, a clear binding response was observed when human IL-22 was injected on 11041 but no response was seen for the IL22R1 injection. This demonstrates that 11041 antibody and IL-22R1 have an overlapping binding site.

TABLE 15

| | | Binning of 11041 antibody to human IL22 and IL22R1 | | | |
|---|---|---|---|---|---|
| Capture | Capture Level (RU) | Human IL-22 concentration | Human IL-22 binding (RU) | Human IL-22R1 concentration | Human IL-22R1 Binding (RU) |
| 11041 Fab | 699 | 0 nM | −0.8 | 0 nM | −1.6 |
| 11041 Fab | 698 | 100 nM | 183.4 | 50 nM | −30.9 |

The surface was generated by 2×10 µL injections of 50 mM HCl, interspersed by a 5 µL injection of 5 mM NaOH at flowrate of 10 µL/min. Background subtraction binding curves were analyzed using the Insight evaluation software following standard procedures. Kinetic parameters were determined from the fitting algorithm. The IL22 affinity determined from a single experiment is shown in Table 14 and was shown to be less than 100 pM.

TABLE 14

| | Binding affinity between humanized 11041 Fab and IL22 | | | |
|---|---|---|---|---|
| Sample | ka | kd | KD (M) | KD (pM) |
| 11041gL13gH14 Fab | 1.01E+06 | 1.26E−05 | 1.25E−11 | 12.48 |

Values determined from a single experiment

Example 7. Blocking of the IL22/IL22R1 Interaction by 11041 Fab

A cross-blocking assay was performed on a Biacore 4000 (GE Healthcare) to determine whether the 11041 rabbit antibody binds to the same binding site as IL22R1.

A CM5 Sensor chip was prepared by activating with a 7-minute injection (at 10 µL min-1) of a mixture of EDC/NHS (GE Healthcare) followed by a 7-minute injection of a rabbit-Fab specific goat Fab'2 (Jackson Immuno Research) at 50 µg/ml in acetate buffer pH 5.0 (GE Healthcare) to achieve an immobilization level of approximately 5500 RU. Finally, a 7-minute injection (at 10 µL min-1) of 1M Ethanolamine hydrochloride-NaOH pH 8.5 was performed to deactivate the surface. A reference surface was prepared as above, omitting the rabbit-Fc specific capture antibody.

Cross-competition was performed at 25° C. in HBS-EP+ buffer (GE Healthcare). Each analysis cycle involved injection of a variable region, formatted as a rabbit Fab followed by an injection of human IL-22 at 100 nM and finally an injection of IL-22R1 at 50 nM. Binding responses were calculated after subtraction of buffer blank and no capture

Example 8. Assessment of Blocking of IL22BP Binding Site on IL22

Surface plasmon resonance (Biacore T200) was used to assess whether 11041gL13gH14 Fab (as a part of a bispecific antibody) or Fezakinumab are able to block the IL22BP binding site of IL22.

A goat anti-human IgG Fab specific antibody (Jackson ImmunoResearch) was immobilized on a CM5 Sensorchip via amine coupling chemistry to a level of approximately 6000RU.

Each analysis cycle consisted of capture of 11041gL13gH14 Fab or Fezakinumab molecules to the anti Fab surface, injection of IL22 at 20 nM (prepared in house) followed by injection of IL22BP at 100 nM, with each injected for 180 s at 30 µl/min. At the end of each cycle the surface was regenerated at a flowrate of 10 µL/min using a 60 s injection of 50 mM HCl followed by a 30 s injection of 5 mM NaOH and a final 60 s injection of 50 mM HCl. Background binding and drift were subtracted using control cycles consisting of buffer capture, or buffer analyte injections.

TABLE 16

| | The IL22 and IL22BP binding responses | | |
|---|---|---|---|
| Sample | Capture (RU) | IL22 Binding at 20 nM (RU) | IL22BP Binding at 100 nM (RU) |
| 11041gL13gH14 Fab | 280 | 40 | 0 |
| Fezakinumab | 202 | 37 | 59 |

When IL22 was bound to surface-captured 11041gL13gH14 Fab, IL22BP was unable to bind IL22. When IL22 was bound to surface-captured Fezakinumab IL22BP was still capable of binding IL22. In conclusion, 11041gL13gH14 Fab (as a part of a bi-specific antibody) blocks the IL22BP binding site of IL22, while Fezakinumab does not.

Example 9. Purification of IL22

A His-tagged version of IL-22 was purified largely as described by Nagem et al [Nagem et al Structure. 2002 August; 10(8):1051-62.]. The BL21(DE3) *E. coli* strain was transformed by heat shock with an expression construct encoding His-tagged IL-22.

The encoded protein sequence is:

```
                                        (SEQ ID NO: 3)
MGSSHHHHHHSSGENLYFQGSQGGAAAPISSHCRLDKSNFQQPYITNRT

FMLAKEASLADNNTDVRLIGEKLFHGVSMSERCYLMKQVLNFTLEEVLF

PQSDRFQPYMQEVVPFLARLSNRLSTCHIEGDDLHIQRNVQKLKDTVKK

LGESGEIKAIGELDLLFMSLRNACI
```

IL-22 protein sequence after TEV cleavage (see below):

```
                                        (SEQ ID NO: 4)
GSQGGAAAPISSHCRLDKSNFQQPYITNRTFMLAKEASLADNNTDVRLI

GEKLFHGVSMSERCYLMKQVLNFTLEEVLFPQSDRFQPYMQEVVPFLAR

LSNRLSTCHIEGDDLHIQRNVQKLKDTVKKLGESGEIKAIGELDLLFMS

LRNACI
```

Cells were grown in the presence of 100 μg/ml ampicillin, and protein expression was induced by adding IPTG to a concentration of 1 mM when the cells reached an optical density (measured at 600 nM) of 1. After 4 hours, the cells were harvested by centrifugation. After cell lysis with a high-pressure cell homogenizer, the inclusion bodies containing IL-22 were collected by high speed centrifugation. The inclusion bodies were washed with 50 mM Tris-HCl, 100 mM NaCl, 1 mM EDTA, 1 mM DTT, and 0.5% (w/v) DOC (pH 8) and then again with the same buffer without detergent. The washed inclusion bodies were solubilised overnight at 4° C. in a buffer containing 50 mM MES, 10 mM EDTA, 1 mM DTT and 8M urea. Insoluble material was separated by centrifugation and IL-22 in the soluble fraction was refolded by dilution to 0.1 mg/ml in 100 mM Tris-HCl, 2 mM EDTA, 0.5M Arginine, 1 mM reduced glutathione and 0.1 mM oxidised glutathione, with a final pH of 8.0. After 72 hours of incubation at 4° C., the protein was concentrated, and purified by size-exclusion chromatography on a HiLoad 26/600 Superdex 75 pg column, equilibrated with 25 mM MES pH 5.4 and 150 mM NaCl. The protein was then frozen at −80° C. until further use.

The His-tag was removed by overnight incubation of the IL-22 protein with TEV protease, at 4° C. After diluting the protein in PBS containing 25 mM imidazole, the cleaved protein was passed over a 5 ml HisTrap™ High Performance column (GE Healthcare) and collected in the flow-through.

Example 10. HDX-MS of IL22 in the Presence of 11041gL13gH14 Fab and 11070gL7gH16 Fab Hydrogen Deuterium Exchange Mass Spectrometry (HDX-MS) was used for epitope mapping of IL22 against 11041gL13gH14 Fab and 11070gL7gH16 Fab.
Sample Preparation and Data Acquisition
For HDX-MS analysis, 30 μM of IL22 (prepared as described in Example 9 and 30 μM of IL22 complexed with 90 μM of either 11041gL13gH14 Fab or 11070gL7gH16 Fab were prepared and incubated for 1 hour at 4° C. 4 μl of IL22, IL22/11041gL13gH14 Fab or IL22/11070gL7gH16

Fab complexes were diluted into 57 μL of 10 mM phosphate in $H_2O$ (pH 7.0), or into 10 mM phosphate in $D_2O$ (pD 7.0) at 25° C. The deuterated samples were then incubated for 0.5, 2, 15 and 60 min at 25° C. After the reaction, all samples were quenched by mixing at 1:1 with a quench buffer (4 M Guanadine Hydrochloride, 250 mM Tris(2-carboxyethyl) phosphine hydrochloride (TCEP), 100 mM phosphate) at 1° C. The mixed solution was at a final pH 2.5. The mixture was immediately injected into the nanoAcquity HDX module (Waters Corp.) for peptic digest. Peptide digestion was then performed online using a Enzymatic online digestion column (Waters) in 0.2% formic acid in water at 20° C. and with a flow rate of 100 μL/min. All deuterated time points and un-deuterated controls were carried out in triplicate with blanks run between each data-point.

Peptide fragments were then trapped using an Acquity BEH C18 1.7 μM VANGUARD chilled pre-column for 3 min. Peptides were then eluted into a chilled Acquity UPLC BEH C18 1.7 μM 1.0×100 using the following gradient: 0 min, 5% B; 6 min, 35% B; 7 min, 40% B; 8 min, 95% B, 11 min, 5% B; 12 min, 95% B; 13 min, 5% B; 14 min, 95% B; 15 min, 5% B (A: 0.2% HCOOH in H2O, B: 0.2% HCOOH in acetonitrile. Peptide fragments were ionized by positive electrospray into a Synapt G2-Si mass spectrometer (Waters). Data acquisition was run in ToF-only mode over an m/z range of 50-2000 Th, using an MSe method (low collision energy, 4V; high collision energy: ramp from 18V to 40V). Glu-1-Fibrinopeptide B peptide was used for internal lock mass correction.
HDX-MS Data Processing MSE data from un-deuterated controls samples of IL22, IL22/11041gL13gH14 Fab or IL22/11070gL7gH16 Fab complexes were used for sequence identification using the Waters Protein Lynx Global Server 2.5.1 (PLGS). Peptide search was performed against a database of the IL22 sequence only, with precursor intensity threshold of 500 counts and 3 matched product ions required for assignment. Ion accounting files for the 3 control samples were combined into a peptide list imported into Dynamx v3.0 software.

Peptides were subjected to further filtering in DynamX. Filtering parameters used were a minimum and maximum peptide sequence length of 4 and 25, respectively, minimum intensity of 1000, minimum MS/MS products of 2, minimum products per amino acid of 0.2, and a maximum MH+error threshold of 10 ppm. DynamX v3.0 was used to quantify the isotopic envelopes resulting from deuterium uptake for each peptide at each time-point. Furthermore, all the spectra were examined and checked visually to ensure correct assignment of m/z peaks and only peptides with a high signal to noise ratios were used for HDX-MS analysis.

Following manual filtration in Dynamx, statistical analysis and filtration were performed using Deuteros (www.academic.oup.com/bioinformatic s/article/35/17/3171/ 5288775) that uses statistical analysis published by Houde et al., 2011 (www.ncbi.nlm.nih.gov/pubmed/21491437). Deuteros generates a woods plot that displays peptide length, start and end residues, global coverage and a y-axis metric which is the absolute uptake (in Daltons). It is the difference in uptake in the presence of a ligand (bound) and the apo form. Woods plots first apply confidence filtering to all peptides in each timepoint. Peptides with differential deuteration outside of the selected confidence limits are non-significant and are shown in light grey. The significant peptides are shown as dark grey and black. An in-house algorithm was used to filter the results and identify an epitope. Data presented is after 0.5 minutes of deuteration incubation.

Coverage Map of IL22

Figure 4:
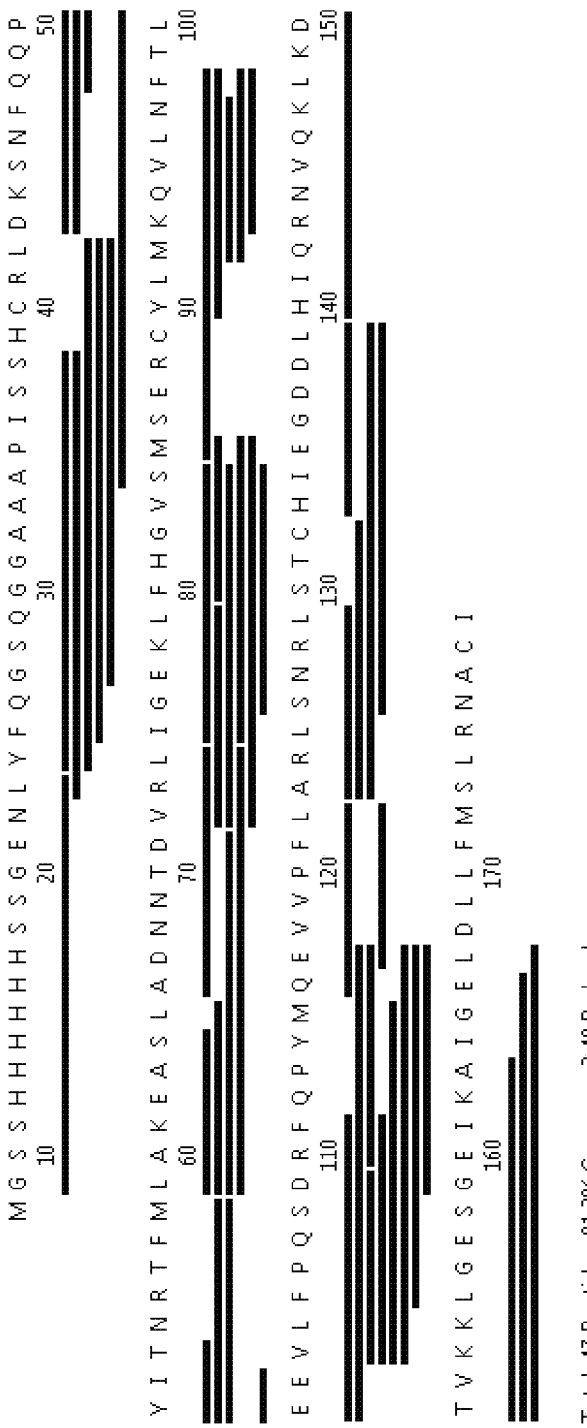
FIG. 4 shows IL22 peptide coverage map of the HDX-MS experiment.

HDX analysis of IL22 with 11041gL13gH14 Fab and 11070gL7gH16 Fab was performed in a single experiment. A total of 91.3% coverage was obtained for the HDX-MS experiment from 47 peptides. The peptide redundancy following filtering and analysis was 3.48. (FIG. 4)

HDX-MS of IL22 in the Presence of 11041gL13gH14 Fab

Figure 5:
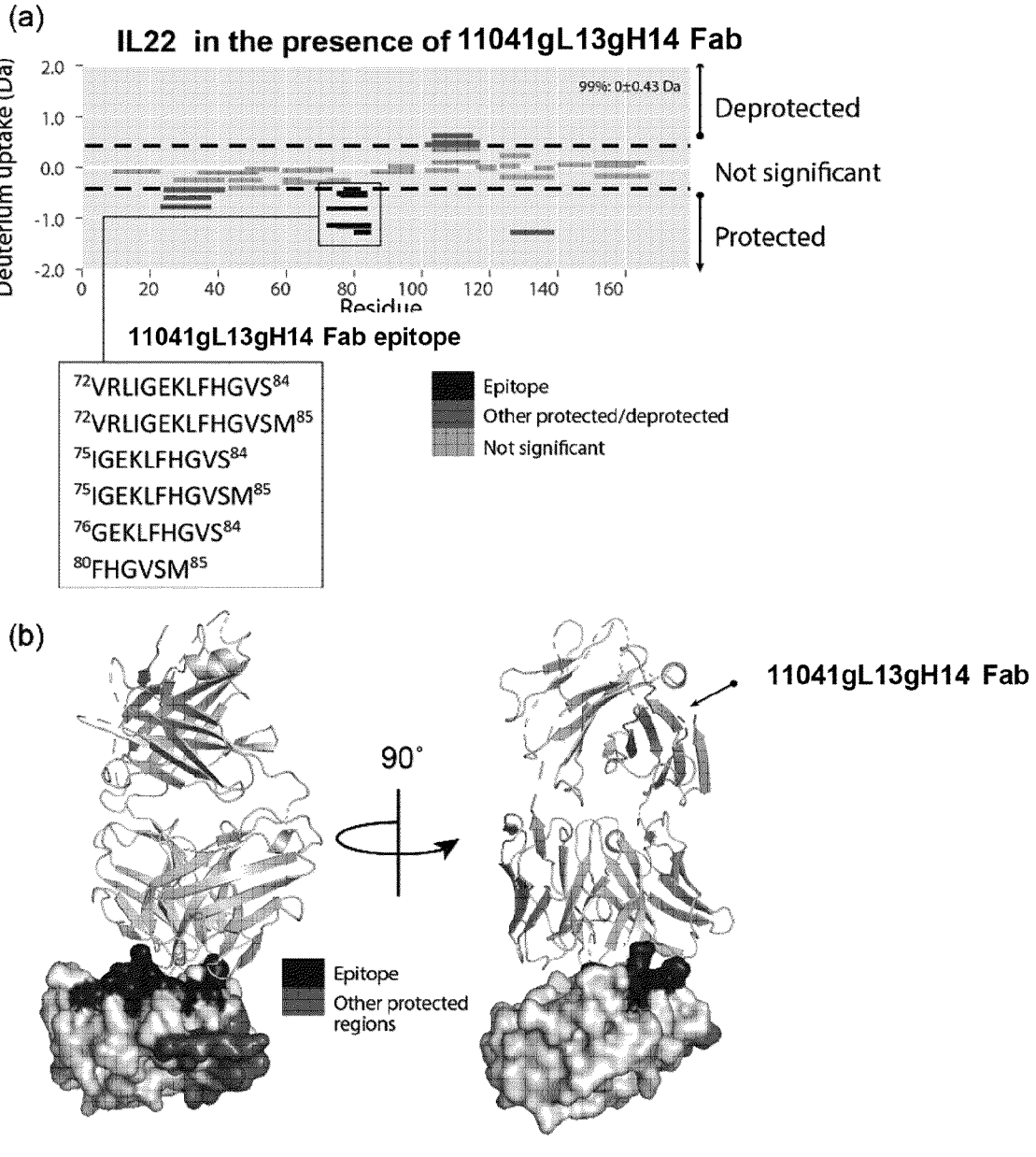
FIG. 5 shows the results of HDX-MS analysis for 11041gL13gH14 Fab. (A) peptides showing significant reduced deuterium incorporation upon antibody binding are listed. Peptides showing a similar exchange pattern in the presence and absence of the antibody have a non-significant deuterium incorporation and are displayed in light grey. (B) determined 11041gL13gH14 Fab epitope is projected onto the IL22 3D structure and highlighted in black. Relative 11041gL13gH14 Fab binding to IL22 from X-ray data is displayed for reference.

Seven peptides showing statistically significant reduced deuterium incorporation upon antibody binding (i e. potential epitope) were observed, six of which agreed with the SPEED analysis (FIG. 5A, highlighted in black on the woods plot): 72VRLIGEKLFHGVS84, 72VRLIGEKLFHGVSM85, 75IGEKLFHGVS84, 75IGEKLFHGVSM85, 76GEKLFHGVS84 and 80FHGVSM85. An increase in deuterium uptake (i.e. potential conformational change) was observed in three peptides: 101EEVLFPQSDRF111, 103VLFPQSDRFQPYM115 and 103VLFPQSDRFQPYMQE117. The 11041gL13gH14 Fab epitope is projected onto the structure of IL22 (FIG. 5B). Other regions that were protected or deprotected upon antibody binding due to conformational change are shown in FIG. 5B and are highlighted in dark grey.

In conclusion, the protected region which represents the epitope region of 11041gL13gH14 Fab is residues 72-85 (VRLIGEKLFHGVSM).

HDX-MS of IL22 in the presence of 11070gL7gH16 Fab

Four peptides showing statistically significant reduced deuterium incorporation upon antibody binding (i.e. potential epitope) were observed, three of which agreed with the SPEED analysis (FIG. 6A, highlighted in black on the woods plot): 72VRLIGEKLFHGVSM85, 75IGEKLFHGVSM85 and An increase in deuterium uptake (i.e. potential conformational change) was observed in two peptides: 43DKSNFQQPYITNRTFM58 and 105FPQSDRFQPYMQE117. The 11070gL7gH16 Fab epitope is projected onto the structure of IL22 (FIG. 6B). Other regions that were protected or deprotected upon antibody binding due to conformational change are shown in FIG. 6B and are highlighted in dark grey.

In conclusion, the protected region which represents the epitope region of 11070gL7gH16 Fab is residues 72-85 (VRLIGEKLFHGVSM).

TABLE 17

List of peptides that show significant change
upon antibody binding measured by HDX-MS.

| HDX-MS of IL22 in the presence of 11041gL13gH14 Fab | | | | |
| --- | --- | --- | --- | --- |
| Start | End | Peptide sequence | SEQ ID NO | Deuterium Uptake |
| 72 | 84 | VRLIGEKLFHGVS | 95 | Protected/epitope |
| 72 | 85 | VRLIGEKLFHGVSM | 96 | Protected/epitope |
| 75 | 84 | IGEKLFHGVS | 97 | Protected/epitope |
| 75 | 85 | IGEKLFHGVSM | 98 | Protected/epitope |
| 76 | 84 | GEKLFHGVS | 99 | Protected/epitope |
| 80 | 85 | FHGVSM | 100 | Protected/epitope |
| 126 | 139 | SNRLSTCHIEGDDL | 101 | Protected |

TABLE 17-continued

List of peptides that show significant change
upon antibody binding measured by HDX-MS.

| | | | | |
| --- | --- | --- | --- | --- |
| 101 | 111 | EEVLFPQSDRF | 102 | Deprotected |
| 103 | 115 | VLFPQSDRFQPYM | 103 | Deprotected |
| 103 | 117 | VLFPQSDRFQPYMQE | 104 | Deprotected |

| HDX-MS of IL22 in the presence of 11070gL7gH16 Fab | | | | |
| --- | --- | --- | --- | --- |
| Start | End | Peptide sequence | SEQ ID NO | Deuterium Uptake |
| 72 | 85 | VRLIGEKLFHGVSM | 96 | Protected/epitope |
| 75 | 85 | IGEKLFHGVSM | 98 | Protected/epitope |
| 80 | 85 | FHGVSM | 100 | Protected/epitope |
| 126 | 139 | SNRLSTCHIEGDDL | 101 | Protected |
| 43 | 58 | DKSNFQQPYITNRTFM | 105 | Deprotected |
| 105 | 117 | FPQSDRFQPYMQE | 106 | Deprotected |

Example 11. Purification and Structural Analysis of the IL-22/11041gL13gH14 Complex IL-22 was purified as described in Example 9.

Cleaved IL-22 was mixed with 11041gL13gH14 Fab and purified by size-exclusion chromatography on a HiLoad® 26/600 Superdex® 75 pg column (GE Healthcare), equilibrated with 10 mM Tris pH7.4 and 150 mM NaCl.

The IL-22/11041gL13gH14 Fab complex was concentrated to 10.1 mg/ml. Crystallization conditions for the complex were identified using several commercially available crystallization screens. These were carried out in sitting drop format, using Swissci 96-well 2-drop MRC Crystallization plates (sourced from Molecular Dimensions, Cat No. MD11-00-100). First, the reservoirs were filled with 75 µL of each crystallization condition in the screens using a Microlab STAR liquid handling system (Hamilton). Then, 300 nL of the IL-22/Fab complex and 300 nL of the reservoir solutions were dispensed in the wells of the crystallization plates using a Mosquito liquid handler (TTP LabTech). An initial crystallization condition was identified in condition 59 of the Nextal Tubes JCSG+ screen (Qiagen Cat No: 130720), containing 0.16 M Calcium acetate hexahydrate, 0.08 M sodium cacodylate pH6.5, 14.4% PEG8000 and 20% glycerol. This condition will be further referred to as JCSG+ 59. Optimised crystals were obtained by adding Yttrium(III) Chloride hexahydrate—which is included in the Additive Screen (Hampton Research Cat No HR2-138)—at 0.01 M to JCSG+59 which was sourced from Molecular Dimensions (Cat No. MDSR-37-E11). The optimised crystals were grown in MRC Maxi 48 Well Crystallization Plates (Swissci), using a reservoir volume of 250 µL and a drop consisting of 2 µL reservoir solution mixed with 2 µL of the IL-22/Fab complex. Before flash freezing in liquid nitrogen, the crystals were transferred to a 4 µL drop of cryoprotection solution. This solution was prepared by mixing 40 µL of the optimized reservoir solution with 10 µL of solution Cryo-Mixes™ 7, included with the CryoProtX™ kit (Molecular Dimensions MD1-61). CryoMixes™ 7 contains 12.5% v/v Diethylene glycol, 12.5% v/v Ethylene glycol, 25% v/v 1,2-Propanediol, 12.5% v/v Dimethyl sulfoxide and 12.5% v/v Glycerol.

Diffraction data were collected at beamline I04 (Diamond Light Source, UK). The data was indexed and integrated using XDS [Kabsch, W. Acta Cryst. D66, 125-132 (2010)], followed by scaling using AIMLESS [Evans et a/Acta Crystallogr D Biol Crystallogr. 2013; 69 (Pt 7):1204-1214]. The IL-22/Fab structure was solved by molecular replacement using Phaser [McCoy et alk Appl. Cryst. (2007). 658-674] in the Phenix software suite [Adams et a/Methods. 2011; 55(1):94-106]. In this procedure, IL-22 structure 1YKB [Xu et a/Acta Crystallogr D Biol Crystallogr. 2005 July; 61 (Pt 7):942-50] and Fab structure SBVJ [Rondeau et a/MAbs. 2015; 7(6):1151-60] were used as molecular replacement templates. Coot [P. Emsley et al (2010). Acta Crystallographica. D66: 486-501] and phenix.refine [P.V. Afonine et a/Acta Crystallogr D Biol Crystallogr 68, 352-67 (2012)] were used in the following cycles of manual model completion and refinement. MolProbity [Williams et al. (2018) Protein Science 27: 293-315] was used to analyze the quality of the final model.

3 IL-22/11041gL13gH14 Fab complexes are observed in the crystal asymmetric unit.

FIG. 7A shows the interaction of 11041gL13gH14 Fab with IL-22, with a detailed view on the interaction interface (FIG. 7B). NCONT in the CCP4 software suite [Winn M D et a/Acta Crystallogr D Biol Crystallogr. 2011 April; 67 (Pt 4):235-42] was used to determine the epitope on IL-22, recognized by the Fab molecule. The IL-22 amino acid numbering is based on UnitProtKB entry Q9GZX6.

At a <4 Å contact distance with the Fab molecule, the IL-22 epitope is composed of residues: Gln48, Glu77, Phe80, His81, Gly82, Va183, Ser84, Met85, Arg88, Leu169, Met172, Ser173, Arg175, Asn176 and Ile179.

At a <5 Å contact distance with the Fab molecule, the IL-22 epitope is composed of residues: Lys44, Phe47, Gln48, Ile75, Gly76, Glu77, Phe80, His81, Gly82, Va183, Ser84, Met85, Ser86, Arg88, Leu169, Met172, Ser173, Arg175, Asn176 and Ile179

TABLE 18

Amino acids of the light chain of 11041gL13gH14 Fab and their corresponding contacts on IL22. Residues in bold are involved in contacts between 4 and 5 Å. Other residues have ≤4 Å contact distance between the antibody and IL-22.

| light chain | IL-22 residue |
|---|---|
| Tyr30 (CDR1) | Gln48 |
| | Arg175 |
| | Lys44 |
| | Phe47 |
| | Gln48 |
| | Ile179 |
| Thr31 (CDR1) | Met172 |
| | Arg175 |
| Asn32 (CDR1) | Arg175 |
| | Asn176 |
| Trp50 (CDR2) | Leu169 |
| | Met172 |
| | Arg175 |
| | Asn176 |
| | Ser173 |
| Tyr93 (CDR3) | Asn176 |
| | Ile179 |
| | Arg88 |
| Gly94 (CDR3) | Ile179 |
| Tyr101 (CDR3) | Met85 |

TABLE 19

Amino acids of the heavy chain of 11041gL13gH14 Fab and their corresponding contacts on IL22. Residues in bold are involved in contacts between 4 and 5 Å. Other residues have ≤4 Å contact distance between the antibody and IL-22.

| heavy chain | IL-22 residue |
|---|---|
| Ser30 (CDR1) | Gly82 |
| Ser31 (CDR1) | Gly82 |
| | Phe80 |
| | His81 |
| Tyr32 (CDR1) | Glu77 |
| | His81 |
| | Glu77 |
| Ala33 (CDR1) | Met85 |
| Ile50 (CDR2) | Met85 |
| Asp52 (CDR2) | Ser84 |
| | Met85 |
| | Val83 |
| | Ser86 |
| Ile53 (CDR2 | Gly82 |
| | Val83 |
| | Ser84 |
| Glu54 (CDR2) | Ser84 |
| Tyr58 (CDR2) | Met85 |
| Arg97 (CDR3) | Glu77 |
| Asp98 (CDR3) | Met85 |
| | Arg88 |
| Arg99 (CDR3) | Glu77 |
| Phe100 (CDR3) | Glu77 |
| | Phe80 |
| | Arg88 |
| | Gly76 |
| | Glu77 |
| Val101 (CDR3) | Glu77 |
| | Ile75 |
| | Gly76 |
| | Glu77 |
| | Phe80 |
| | Ser173 |
| Gly102 (CDR3) | Phe80 |
| | Met172 |
| | Ser173 |
| | Asn176 |
| Val103 (CDR3) | Asn176 |
| Asp104 (CDR3) | Arg88 |
| | Met85 |

The 11041gL13gH14 Fab molecule prevents the interaction of IL-22 with the IL22R1 receptor, as the Fab light chain binds to the same region on IL22. (FIG. 8)

Example 11. Structure Determination of IL-22 in Complex with Fezakinumab and VR11070 by Cryo-EM After performing structural analysis of the IL22/ 11041gL13gH14 complex, structure determination of IL22 in complex with Fezakinumab and 11070gL7gH16 Fab (VR11070) was performed using cryo-EM technology.

IL-22 was expressed using Expi293 cells, fused to an N-terminal human Fc tag. After clearing the cells by centrifugation, the supernatant was loaded on a 5 ml HiTrap Protein A column (Cytiva). The protein was eluted with a buffer gradient from PBS to 0.1 M Sodium Citrate at pH 2.0. The hFc tag was cleaved using TEV protease and IL22 was separated from the cleaved tag by another pass by gravity flow over 4 ml packed protein A resin. After elution from the resin, IL-22 was further purified on a HiLoad 26/600 Superdex75 pg column (Cytiva), equilibrated in PBS.

70 microliters VR11070 Fab at 12.1 mg/ml, 153 microliters Fezakinumab Fab at 11.5 mg/ml and 153 microliter IL22 at 1.36 mg/ml were mixed. 55 microliters were injected onto a Superdex200 5/150 column equilibrated in 10 mM Hepes pH 7.4 and 150 mM NaCl. A fraction containing the IL-22+VR11070+Fezakinumab complex at 1.7 mg/ml was collected and used for preparing cryo-EM grids.

Quantifoil® R 1.2/1.3 holey carbon grids (SPT Labtech) were glow-discharged in a Pelco easyGlow™ for 45 s at 22 mA immediately before use. The IL22 with 11070gL7gH16 Fab and Fezakinumab Fab after gel filtration was applied to the freshly glow-discharged grid in a Vitrobot Mark IV (Thermo Fisher Scientific) for 2 s in the chamber at 100% humidity and 4° C. The grid was then blotted on fresh filter paper for 4 s at force 7 and plunged in liquid ethane. The grid was first screened for ice thickness and particle distribution in the in-house Glacios operated at 200 keV and equipped with a Falcon 3 camera. The data was then collected on the Krios2 of the Cambridge consortium equipped with a Falcon 4 and operated at 300 keV acceleration voltage. The 5700 movies were collected automatically using the EPU software, in counting mode at a defocus range of –1 to –2.5 μm, at a pixel size of 0.67 Å with a 12.2 s exposure for a final electron flux of 49.36 e$^-$/Å$^2$ distributed over 42 fractions. All subsequent data analysis was performed on Cryosparc, version 2.15 (Structura Biotechnology Inc). The movies were aligned using Patch Motion, contrast transfer function parameters (CTF) were estimated using Patch CTF and particles were initially picked with the blob picker and resulted in a total of 5.5 M particles. The picked particles were binned 2× to a box size of 300 pixels and subjected to a first round of 2D classification that resulted in the selection of 488,000 particles with distinct features. Five ab initio models were generated, 2 of which differed from one another at the glycosylation sites of IL22. These two classes, for a total of 240,000 particles, were pooled together and a non-uniform refinement yielded a resolution estimation of 3.4 Å using the gold-standard FSC 0.143 criterion.

Two Fab molecules and the IL22 structure were fitted in the cryo-EM density using UCSF Chimera [Pettersen, et alk Comput. Chem. 25(13):1605-1612 (2004)]. After further manual model building using Coot [Emsley et a/(2010) Acta Crystallographica. D66: 486-501.], the map was sharpened using the Autosharpen [Terwilliger. (2018). Acta Cryst. D74, 545-559.] tool in Phenix [Liebschner et al. Acta Cryst. D75, 861-877 (2019)] and the model was further refined using the Real-space refinement [Afonine et al Acta Cryst. D74, 531-544 (2018)] tool in Phenix.

NCONT in the CCP4 software suite [Winn et a/Acta Crystallogr D Biol Crystallogr. 2011 April; 67 (Pt 4):235-42] was used to determine the epitope on IL22, recognized by the 11070gL7gH16 Fab and Fezakinumab Fab molecules. The IL22 amino acid numbering below is based on Unit-ProtKB entry Q9GZX6.

At a <4 Å contact distance with the 11070gL7gH16 Fab molecule, the IL22 epitope is composed of residues: Glu77, Lys78, His81, Ser84, Met85, Ser86, Arg88, Asn176, Ala177

At a <5 Å contact distance with the 11070gL7gH16 Fab molecule, the IL22 epitope is composed of residues: Ile75, Gly76, Glu77, Lys78, Phe80, His81, Ser84, Met85, Ser86, Arg88, Leu169, Met172, Ser173, Asn176, Ala177

At a <4 Å contact distance with the Fezakinumab Fab molecule, the IL22 epitope is composed of residues: Gln49, Tyr51, Phe105, Ser108, Asp109, Gln112, Pro113, Tyr114, Gln116, Glu117, Pro120, Ala123, Arg124

At a <5 Å contact distance with the Fezakinumab Fab molecule, the IL22 epitope is composed of residues: Gln49, Pro50, Tyr51, Ile52, Arg55, Phe105, Pro106, Ser108, Asp109, Gln112, Pro113, Tyr114, Gln116, Glu117, Val119, Pro120, Phe121, Ala123, Arg124

The structural analysis reveals that 11070 Fab has a different epitope on IL-22 than Fezakinumab. Also, the 11070gL7gH16 Fab (VR11070) is similar to the epitope of 11041gL13gH14 Fab (VR11041) on IL22. (FIGS. 9A and 9B). Like 11041gL13gH14 Fab, 11070gL7gH16 Fab blocks IL22 signalling by preventing the interaction with the IL-22R1 receptor (FIG. 10A). In contrast, Fezakinumab blocks IL22 signalling by preventing the interaction of IL22 with IL10R2 (FIG. 10B).

Example 12. COLO205 IL-10 Release Assay

The antibody was tested in an in vitro cell assay for activity against human IL22. The COLO205 cell line is a human colorectal cancer epithelial cell line. IL22 binds to IL22R1 and IL10R2 on the cell surface to induce STAT3 phosphorylation and downstream cytokine release (e.g. IL-10). In this assay, COLO205 cells are stimulated with IL22 with or without anti-IL-22 antibodies. The resultant IL-10 response is then measured in the cell culture supernatant using a homogenous time-resolved FRET (HTRF) kit (Cisbio).

COLO205 cells were seeded at 25000 cells per well in tissue culture treated flat bottomed 96 well plates. Human IL-22 (final assay concentration 30 pM) was pre-incubated with antibody (final assay concentration 3 nM-1.4 pM) at 37° C. for one hour. The antibody/cytokine complexes were then transferred to the COLO205 cells and incubated for 48 hours at 37° C., 5% CO2. Cell-free cell culture supernatants were then collected and stored at –80° C. Cell culture supernatants were defrosted on ice and the levels of IL-10 were determined by HTRF.

Samples were run either in singlicate, or in duplicate. 11041 Fab Results

The results confirm that 11041 Fab inhibits the IL-22-induced IL-10 response of COLO205 cells in the COLO205 IL-10 release assay. 11041 Fab had an IC50 of 56.78 pM, as determined by the geometric mean of 2 occasions of the assay (Table 20). These measurements are deemed reliable as the range of the measured IC50 in each repetition of the assay was found to vary by less than threefold in each instance.

TABLE 20

Table of data for 11041 Fab in the COLO205 IL-10 release assay.

| | IC$_{50}$ (M) | | Maximum % inhibition | | Hill Slope | |
|---|---|---|---|---|---|---|
| | Geomean | Range | Arithmetic mean | Range | Geomean | Range |
| 11041 Fab (N = 2) | 5.68e–011 | 5.50e–011 5.86e–011 | 101.7 | 101.6 101.7 | 1.824 | 1.762 1.889 |

11041 gL13gH14 Fab Results

The results confirm that 11041 gL13gH14 Fab inhibits the IL-22-induced IL-10 response of COLO205 cells in the COLO205 IL-10 release assay. 11041 gL13gH14 Fab had an IC50 of 42.7 pM, as determined by the geometric mean of 2 occasions of the assay (Table 21). These measurements are deemed reliable as the range of the measured IC50 in each repetition of the assay was found to vary by less than threefold in each instance.

TABLE 21

Table of data for 11041 gL13gH14 Fab in the COLO205 IL-10 release assay.

| | $IC_{50}$ (M) | | Maximum % inhibition | | Hill Slope | |
|---|---|---|---|---|---|---|
| | Geomean | Range | Arithmetic mean | Range | Geomean | Range |
| 11041 gL13gH14 Fab (N = 2) | 4.27e−011 | 4.04e−011 4.52e−011 | 105.7 | 101.5 109.8 | 1.161 | 0.903 1.492 |

Example 13. In Vitro Human Primary Keratinocyte Cell Based Activity of the 11041gL13gH14 Fab Against Human IL22

The antibody molecule 11041gL13gH14 Fab was tested in an in vitro cell assay against activity of human IL-22 (in house produced). The primary human neonatal epidermal keratinocytes from foreskin (NHEK) were ethically sourced from donors (Promocell, cat no #C-12001), expanded in culture and used in the assay. NHEK cells respond to IL-22 stimulation by secretion of soluble molecules, including S100A7 (psoriasin), that can be detected in cell supernatants (FIG. 11A). S100A7 has been used in the assay as a biomarker to assess 11041gL13gH14 Fab activity.

NHEK cells from two donors at passage 2 and 3 were plated at $10^4$ cells per well in dermal basal media (LGC, cat no #ATCC-PCS-200-030) containing keratinocyte growth kit (LGC, ca no #ATCC-PCS-200-040) in 48-well plates (Corning, Costar® Clear TC-treated Plates, cat no #3548) pre-coated with extracellular matrix (TheromoFisher, cat no #R011K). Keratinocytes were cultured in standard conditions (37° C., 5% CO2, 100% humidity) until they reached confluence. On day 3 growth medium was aspirated from all wells and cells were washed with 200 μl basal dermal media to remove any dead cells and growth factors. The anti-IL22 antibody 11041gL13gH14 Fab at range of concentrations from 50 to 0.01 nM (2500-1 ng/ml) was preincubated with 100 ng/ml of IL22 in dermal basal media at 37° C. for 30 minutes. Fezakinumab in Fab format (anti-IL-22 antibody, in house stock, batch no #PB7490) at 50 nM (2500 ng/ml) was also preincubated with 100 ng/ml of IL22 in dermal basal media at 37° C. for 30 minutes. Then antibody/cytokine solution, 400 μl per well, was transferred to cells. After 48 hrs of stimulation, supernatants were collected and levels of S100A7 were measured using ELISA (LSBio, cat no #LS-F50031).

An increase in S100A7 was measured post IL22 stimulation (FIG. 11A). Fezakinumab Fab at 50 nM fully inhibited S100A7 signal induced by IL22. 11041gL13gH14 Fab at 50 nM also showed full inhibition of S100A7 (FIG. 11A). 11041gL13gH14 Fab showed a concentration dependent inhibition of S100A7 (FIG. 11B).

In conclusion, 11041gL13gH14 Fab tested in the human primary keratinocyte assay showed dose dependent inhibition of the IL-22 dependent biomarker (S100A7).

Example 14. IL22 Phospho STAT3 Method

Hacat cells were added to a 96 well flat bottomed tissue culture plate at 150,000 cells per well in 100 μls of DMEM+ 10% FBS+2 mM L-glutamine per well and incubated at 37 degrees and 5% CO2 overnight. An anti-IL22 antibody was diluted in mock supernatant media to a final assay concentration of 18.75 nM and 60 μls was added to columns 1 and 12 of a 96 well polypropylene V bottomed plate as the minimum signal control. 60 μls of mock supernatant media was added to cols 2 and 11 of the 96 well polypropylene V bottomed plate as the maximum signal controls. Samples were titrated 1:3 into mock supernatant media leaving a final volume of 60 μls in columns 3-10 of the 96 well polypropylene V bottomed plate. 30 μls IL22 solution was added to all wells giving a final assay concentration of 30 ng/ml FAC. The plates were preincubated for 1 hr at 37 degrees. 75 μls of the culture media from cell culture plates to leave 25 μls in the plate. 75 μls of sample titration/controls+i122 was transferred to the cell plate. These plates were Incubated at 37 degrees for 30 minutes. Supernatants were removed. Cisbio STAT3 Phospho Y705 kit was used to lyse the remaining cells and generate HTRF signals from the lysate for each well. The plates were sealed and incubated at room temperature on a shaker over night for 18 hours. The well signals were measured using a HTRF protocol on the Synergy Neo 2 plate reader. The 11041 and 11070 antibodies demonstrated clear inhibition of IL22-induced STAT3 phosphorylation.

All references cited herein, including patents, patent applications, papers, textbooks and the like, and the references cited therein, to the extent that they are not already, are hereby incorporated herein by reference in their entirety.

What is claimed is:

1. An isolated antibody that binds to interleukin 22 (IL22) and inhibits or attenuates IL22 binding to IL22 receptor 1 (IL22R1), the isolated antibody comprising:

a light chain variable region comprising:
    a CDR-L1 comprising SEQ ID NO:5,
    a CDR-L2 comprising SEQ ID NO:6, and
    a CDR-L3 comprising SEQ ID NO:7;
and a heavy chain variable region comprising:
    a CDR-H1 comprising SEQ ID NO:8,
    a CDR-H2 comprising SEQ ID NO:9, and
    a CDR-H3 comprising SEQ ID NO: 10.

2. The antibody according to claim 1, wherein said antibody:

(a) binds to a region on IL22, wherein the binding sterically blocks the interaction between IL22 and IL22R1;

(b) inhibits or attenuates IL22 binding to IL22 binding protein (IL22RA2); and (c) binds to human and cynomolgus monkey IL22.

3. The antibody according to claim 1, wherein said antibody has dissociation equilibrium constant (KD) of less than 100 pM for human IL22.

4. The antibody according to claim 1, wherein the antibody specifically binds to the polypeptide VRLIGEKLFHGVSM (SEQ ID NO: 96) corresponding to residues 72-85 of the amino-acid sequence of IL22 defined by SEQ ID NO:1.

5. The antibody according to claim 1, wherein the antibody binds to an epitope of human IL22, the epitope comprising five or more residues selected from Lys44, Phe47, Gln48, Ile75, Gly76, Glu77, Phe80, His81, Gly82, Val83, Ser84, Met85, Ser86, Arg88, Leu169, Met172, Ser173, Arg175, Asn176 and Ile179 of human IL22 (SEQ ID NO: 1) as determined at the distance of less than 5 Å contact distance between the antibody and IL22.

6. The antibody according to claim 5, wherein said binding is determined by X-ray crystallography.

7. The antibody according to claim 1, wherein the light chain variable region comprises the sequence set forth in SEQ ID NO:22.

8. The antibody according to claim 1, wherein the heavy chain variable region comprises the sequence set forth in SEQ ID NO:24.

9. The antibody according to claim 1, wherein the light chain variable region comprises the sequence set forth in SEQ ID NO: 22, or a sequence which is at least 90% identical thereto; and the heavy chain variable region comprises the sequence set forth in SEQ ID NO: 24, or a sequence which is at least 90% identical thereto.

10. The antibody according to claim 1, wherein said antibody is a full length antibody.

11. The antibody according to claim 1, wherein said antibody is an antibody fragment.

12. The antibody according to claim 11, wherein said antibody fragment is Fab, Fab', F(ab')$_2$, Fv, dsFv, scFv, or dsscFv.

13. The antibody according to claim 12, wherein the antibody is a Fab comprising a light chain comprising the sequence set forth SEQ ID NO: 26 and a heavy chain comprising the sequence set forth in SEQ ID NO: 28.

14. The antibody according to claim 12, wherein the antibody is a Fab.

15. The antibody according to claim 10, wherein the antibody is an IgG1 comprising a light chain comprising the sequence set forth in SEQ ID NO: 26 and a heavy chain comprising the sequence set forth in SEQ ID NO: 30.

16. The antibody according to claim 10, wherein the antibody is an IgG1.

17. The antibody according to claim 10, wherein the antibody is an IgG4P comprising a light chain comprising the sequence set forth SEQ ID NO: 26 and a heavy chain comprising the sequence set forth in SEQ ID NO: 32.

18. The antibody according to claim 10, wherein the antibody is an IgG4P.

19. A pharmaceutical composition comprising the antibody of claim 1, and a pharmaceutically acceptable adjuvant or carrier.

\* \* \* \* \*

SEQUENCE LISTING

<160> NUMBER OF SEQ ID NOS: 106

<210> SEQ ID NO 1
<211> LENGTH: 179
<212> TYPE: PRT
<213> ORGANISM: Homo sapiens

<400> SEQUENCE: 1

```
Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
                115                 120                 125

Leu Ser Thr Cys His Ile Glu Gly Asp Asp Leu His Ile Gln Arg Asn
            130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 2
<211> LENGTH: 146
<212> TYPE: PRT
<213> ORGANISM: Homo sapiens

<400> SEQUENCE: 2

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
                100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
            130                 135                 140
```

-continued

```
Cys Ile
145

<210> SEQ ID NO 3
<211> LENGTH: 172
<212> TYPE: PRT
<213> ORGANISM: Artificial Sequence
<220> FEATURE:
<223> OTHER INFORMATION: His tag IL22

<400> SEQUENCE: 3

Met Gly Ser Ser His His His His His His Ser Ser Gly Glu Asn Leu
1               5                   10                  15

Tyr Phe Gln Gly Ser Gln Gly Gly Ala Ala Ala Pro Ile Ser Ser His
                20                  25                  30

Cys Arg Leu Asp Lys Ser Asn Phe Gln Gln Pro Tyr Ile Thr Asn Arg
            35                  40                  45

Thr Phe Met Leu Ala Lys Glu Ala Ser Leu Ala Asp Asn Asn Thr Asp
        50                  55                  60

Val Arg Leu Ile Gly Glu Lys Leu Phe His Gly Val Ser Met Ser Glu
65                  70                  75                  80

Arg Cys Tyr Leu Met Lys Gln Val Leu Asn Phe Thr Leu Glu Glu Val
                85                  90                  95

Leu Phe Pro Gln Ser Asp Arg Phe Gln Pro Tyr Met Gln Glu Val Val
                100                 105                 110

Pro Phe Leu Ala Arg Leu Ser Asn Arg Leu Ser Thr Cys His Ile Glu
            115                 120                 125

Gly Asp Asp Leu His Ile Gln Arg Asn Val Gln Lys Leu Lys Asp Thr
        130                 135                 140

Val Lys Lys Leu Gly Glu Ser Gly Glu Ile Lys Ala Ile Gly Glu Leu
145                 150                 155                 160

Asp Leu Leu Phe Met Ser Leu Arg Asn Ala Cys Ile
                165                 170

<210> SEQ ID NO 4
<211> LENGTH: 153
<212> TYPE: PRT
<213> ORGANISM: Homo sapiens

<400> SEQUENCE: 4

Gly Ser Gln Gly Gly Ala Ala Ala Pro Ile Ser Ser His Cys Arg Leu
1               5                   10                  15

Asp Lys Ser Asn Phe Gln Gln Pro Tyr Ile Thr Asn Arg Thr Phe Met
                20                  25                  30

Leu Ala Lys Glu Ala Ser Leu Ala Asp Asn Asn Thr Asp Val Arg Leu
            35                  40                  45

Ile Gly Glu Lys Leu Phe His Gly Val Ser Met Ser Glu Arg Cys Tyr
        50                  55                  60

Leu Met Lys Gln Val Leu Asn Phe Thr Leu Glu Glu Val Leu Phe Pro
65                  70                  75                  80

Gln Ser Asp Arg Phe Gln Pro Tyr Met Gln Glu Val Val Pro Phe Leu
                85                  90                  95

Ala Arg Leu Ser Asn Arg Leu Ser Thr Cys His Ile Glu Gly Asp Asp
                100                 105                 110

Leu His Ile Gln Arg Asn Val Gln Lys Leu Lys Asp Thr Val Lys Lys
            115                 120                 125
```

```
Leu Gly Glu Ser Gly Glu Ile Lys Ala Ile Gly Glu Leu Asp Leu Leu
    130                 135                 140

Phe Met Ser Leu Arg Asn Ala Cys Ile
145                 150

<210> SEQ ID NO 5
<211> LENGTH: 11
<212> TYPE: PRT
<213> ORGANISM: Artificial Sequence
<220> FEATURE:
<223> OTHER INFORMATION: CDR seq

<400> SEQUENCE: 5

Gln Ala Ser Glu Asp Ile Tyr Thr Asn Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDR seq

<400> SEQUENCE: 6

Trp Ala Ser Thr Leu Ala Ser
1               5

<210> SEQ ID NO 7
<211> LENGTH: 14
<212> TYPE: PRT
<213> ORGANISM: Artificial Sequence
<220> FEATURE:
<223> OTHER INFORMATION: CDR seq

<400> SEQUENCE: 7

Gln Ala Ser Val Tyr Gly Asn Ala Ala Asp Ser Arg Tyr Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDR seq

<400> SEQUENCE: 8

Gly Phe Ser Leu Ser Ser Tyr Ala Met Ile
1               5                   10

<210> SEQ ID NO 9
<211> LENGTH: 16
<212> TYPE: PRT
<213> ORGANISM: Artificial Sequence
<220> FEATURE:
<223> OTHER INFORMATION: CDR seq

<400> SEQUENCE: 9

Ile Ile Asp Ile Glu Gly Ser Thr Tyr Tyr Ala Ser Trp Ala Lys Gly
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: CDR seq
```

-continued

```
<400> SEQUENCE: 10

Asp Arg Phe Val Gly Val Asp Ile Phe Asp Pro
1               5                   10

<210> SEQ ID NO 11
<211> LENGTH: 14
<212> TYPE: PRT
<213> ORGANISM: Artificial Sequence
<220> FEATURE:
<223> OTHER INFORMATION: CDR seq

<400> SEQUENCE: 11

Gln Ala Cys Val Tyr Gly Asn Ser Ala Asp Ser Arg Tyr Thr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: CDR seq

<400> SEQUENCE: 12

Gln Ala Ser Val Tyr Gly Asn Ser Ala Asp Ser Arg Tyr Thr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: CDR seq

<400> SEQUENCE: 13

Gln Ala Val Val Tyr Gly Asn Ser Ala Asp Ser Arg Tyr Thr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: CDR seq

<400> SEQUENCE: 14

Gln Ala Cys Val Tyr Gly Asn Ala Ala Asp Ser Arg Tyr Thr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: CDR seq

<400> SEQUENCE: 15

Gln Ala Val Val Tyr Gly Asn Ala Ala Asp Ser Arg Tyr Thr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: CDR seq

<400> SEQUENCE: 16
```

```
Gln Ala Cys Val Tyr Gly Asp Ser Ala Asp Ser Arg Tyr Thr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: CDR seq

<400> SEQUENCE: 17

Gln Ala Ser Val Tyr Gly Asp Ser Ala Asp Ser Arg Tyr Thr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: CDR seq

<400> SEQUENCE: 18

Gln Ala Val Val Tyr Gly Asp Ser Ala Asp Ser Arg Tyr Thr
1               5                   10

<210> SEQ ID NO 19
<211> LENGTH: 16
<212> TYPE: PRT
<213> ORGANISM: Artificial Sequence
<220> FEATURE:
<223> OTHER INFORMATION: CDR seq

<400> SEQUENCE: 19

Ile Ile Asp Ile Asp Gly Ser Thr Tyr Tyr Ala Ser Trp Ala Lys Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: CDR seq

<400> SEQUENCE: 20

Ile Ile Asp Ile Asp Ala Ser Thr Tyr Tyr Ala Ser Trp Ala Lys Gly
1               5                   10                  15

<210> SEQ ID NO 21
<211> LENGTH: 11
<212> TYPE: PRT
<213> ORGANISM: Artificial Sequence
<220> FEATURE:
<223> OTHER INFORMATION: CDR seq

<400> SEQUENCE: 21

Asp Arg Phe Val Gly Val Asp Ile Phe Glu Pro
1               5                   10

<210> SEQ ID NO 22
<211> LENGTH: 112
<212> TYPE: PRT
<213> ORGANISM: Artificial Sequence
<220> FEATURE:
<223> OTHER INFORMATION: 11041 gL6 C91S S96A (gL13) V-region

<400> SEQUENCE: 22
```

```
Ala Val Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ala
                85                  90                  95

Ala Asp Ser Arg Tyr Thr Phe Gly Gly Gly Thr Lys Val Glu Ile Lys
            100                 105                 110
```

<210> SEQ ID NO 23
<211> LENGTH: 342
<212> TYPE: DNA
<213> ORGANISM: Artificial Sequence
<220> FEATURE:
<223> OTHER INFORMATION: 11041 gL6 C91S S96A (gL13) V-region

<400> SEQUENCE: 23

```
gccgtccaac tgactcagtc cccgagctca ctttccgcga gcgtgggaga tcgcgtgacc      60
attacgtgcc aggcctcgga ggacatctac accaacctcg cctggtatca acagaagcct     120
ggcaaagctc ccaagctgtt gatctactgg gcctccactc tggcctccgg agtgccttcg     180
cggttctccg gttctggatc aggcaccgac ttcaccctga caatcagcag cctccagccg     240
gaagattttg ccacttacta ctgccaagca tccgtctacg ggaacgcagc ggactccaga     300
tataccttcg gcgggggaac caaagtggag attaagcgta cg                        342
```

<210> SEQ ID NO 24
<211> LENGTH: 119
<212> TYPE: PRT
<213> ORGANISM: Artificial Sequence
<220> FEATURE:
<223> OTHER INFORMATION: 11041 gH5 D54E (gH14) V-region

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser
            115
```

<210> SEQ ID NO 25

<211> LENGTH: 357
<212> TYPE: DNA
<213> ORGANISM: Artificial Sequence
<220> FEATURE:
<223> OTHER INFORMATION: 11041 gH5 D54E (gH14) V-region

<400> SEQUENCE: 25
gaggtgcagc tcgtggaaag cggaggagga ctggtgcagc caggagggtc cttgcggctt      60
agctgtgccg tgtccggctt ctccctgtcc tcctacgcca tgatctgggt ccgccaagct     120
cctgggaagg gcctcgaatg gattggtatt atcgacatcg agggatcaac ctactacgcc     180
tcgtgggcca aggacggtt caccatctcg cgggacaact ccaagaacac tgtgtatctg      240
cagatgaaca gcctgagggc agaagatacc gccgtgtact actgcgcgag agatcgcttc     300
gtgggcgtgg acatctttga cccgtggggt caaggcaccc tggtcactgt ctcgagc        357

<210> SEQ ID NO 26
<211> LENGTH: 219
<212> TYPE: PRT
<213> ORGANISM: Artificial Sequence
<220> FEATURE:
<223> OTHER INFORMATION: 11041gL13 Light chain

<400> SEQUENCE: 26

Ala Val Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ala
                85                  90                  95

Ala Asp Ser Arg Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 27
<211> LENGTH: 657
<212> TYPE: DNA
<213> ORGANISM: Artificial Sequence
<220> FEATURE:
<223> OTHER INFORMATION: 11041gL13 Light chain -continued

<400> SEQUENCE: 27

```
gccgtccaac tgactcagtc cccgagctca ctttccgcga gcgtgggaga tcgcgtgacc        60
attacgtgcc aggcctcgga ggacatctac accaacctcg cctggtatca acagaagcct       120
ggcaaagctc ccaagctgtt gatctactgg gcctccactc tggcctccgg agtgccttcg       180
cggttctccg gttctggatc aggcaccgac ttcaccctga caatcagcag cctccagccg       240
gaagattttg ccacttacta ctgccaagca tccgtctacg ggaacgcagc ggactccaga       300
tataccttcg gcgggggaac caaagtggag attaagcgta cggtggccgc tccctccgtg       360
ttcatcttcc caccctccga cgagcagctg aagtccggca ccgcctccgt cgtgtgcctg       420
ctgaacaact ctaccccccg cgaggccaag gtgcagtgga aggtggacaa cgccctgcag       480
tccggcaact cccaggaatc cgtcaccgag caggactcca aggacagcac ctactccctg       540
tcctccaccc tgaccctgtc caaggccgac tacgagaagc acaaggtgta cgcctgcgaa       600
gtgacccacc agggcctgtc cagccccgtg accaagtcct tcaaccgggg cgagtgc         657
```

<210> SEQ ID NO 28
<211> LENGTH: 222
<212> TYPE: PRT
<213> ORGANISM: Artificial Sequence
<220> FEATURE:
<223> OTHER INFORMATION: 11041gH14 Fab Heavy chain

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys
    210                 215                 220
```

<210> SEQ ID NO 29

<211> LENGTH: 666
<212> TYPE: DNA
<213> ORGANISM: Artificial Sequence
<220> FEATURE:
<223> OTHER INFORMATION: 11041gH14 Fab Heavy chain

<400> SEQUENCE: 29

```
gaggtgcagc tcgtggaaag cggaggagga ctggtgcagc caggagggtc cttgcggctt      60
agctgtgccg tgtccggctt ctccctgtcc tcctacgcca tgatctgggt ccgccaagct     120
cctgggaagg gcctcgaatg gattggtatt atcgacatcg agggatcaac ctactacgcc     180
tcgtgggcca aggacggtt caccatctcg cgggacaact ccaagaacac tgtgtatctg     240
cagatgaaca gcctgagggc agaagatacc gccgtgtact actgcgcgag agatcgcttc     300
gtgggcgtgg acatctttga cccgtggggt caaggcaccc tggtcactgt ctcgagcgcg     360
tccacaaagg gcccatcggt cttccccctg gcaccctcct ccaagagcac ctctgggggc     420
acagcggccc tgggctgcct ggtcaaggac tacttccccg aaccagtgac ggtgtcgtgg     480
aactcaggtg ccctgaccag cggcgttcac accttcccgg ctgtcctaca gtcttcagga     540
ctctactccc tgagcagcgt ggtgaccgtg ccctccagca gcttgggcac ccagacctac     600
atctgcaacg tgaatcacaa gcccagcaac accaaggtcg ataagaaagt tgagcccaaa     660
tcttgt                                                               666
```

<210> SEQ ID NO 30
<211> LENGTH: 449
<212> TYPE: PRT
<213> ORGANISM: Artificial Sequence
<220> FEATURE:
<223> OTHER INFORMATION: 11041gH14 heavy chain (IgG1)

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
            195                  200                  205

Ser Asn Thr Lys Val Asp Lys Lys Val Glu Pro Lys Ser Cys Asp Lys
    210                  215                  220

Thr His Thr Cys Pro Pro Cys Pro Ala Pro Glu Leu Leu Gly Gly Pro
225                  230                  235                  240

Ser Val Phe Leu Phe Pro Pro Lys Pro Lys Asp Thr Leu Met Ile Ser
                245                  250                  255

Arg Thr Pro Glu Val Thr Cys Val Val Val Asp Val Ser His Glu Asp
            260                  265                  270

Pro Glu Val Lys Phe Asn Trp Tyr Val Asp Gly Val Glu Val His Asn
            275                  280                  285

Ala Lys Thr Lys Pro Arg Glu Glu Gln Tyr Asn Ser Thr Tyr Arg Val
    290                  295                  300

Val Ser Val Leu Thr Val Leu His Gln Asp Trp Leu Asn Gly Lys Glu
305                  310                  315                  320

Tyr Lys Cys Lys Val Ser Asn Lys Ala Leu Pro Ala Pro Ile Glu Lys
                325                  330                  335

Thr Ile Ser Lys Ala Lys Gly Gln Pro Arg Glu Pro Gln Val Tyr Thr
            340                  345                  350

Leu Pro Pro Ser Arg Asp Glu Leu Thr Lys Asn Gln Val Ser Leu Thr
            355                  360                  365

Cys Leu Val Lys Gly Phe Tyr Pro Ser Asp Ile Ala Val Glu Trp Glu
    370                  375                  380

Ser Asn Gly Gln Pro Glu Asn Asn Tyr Lys Thr Thr Pro Pro Val Leu
385                  390                  395                  400

Asp Ser Asp Gly Ser Phe Phe Leu Tyr Ser Lys Leu Thr Val Asp Lys
                405                  410                  415

Ser Arg Trp Gln Gln Gly Asn Val Phe Ser Cys Ser Val Met His Glu
            420                  425                  430

Ala Leu His Asn His Tyr Thr Gln Lys Ser Leu Ser Leu Ser Pro Gly
        435                  440                  445

Lys
```

```
<210> SEQ ID NO 31
<211> LENGTH: 1347
<212> TYPE: DNA
<213> ORGANISM: Artificial Sequence
<220> FEATURE:
<223> OTHER INFORMATION: 11041gH14 heavy chain (IgG1)

<400> SEQUENCE: 31
gaggtgcagc tcgtggaaag cggaggagga ctggtgcagc caggagggtc cttgcggctt      60
agctgtgccg tgtccggctt ctccctgtcc tcctacgcca tgatctgggt ccgccaagct     120
cctgggaagg gcctcgaatg gattggtatt atcgacatcg agggatcaac ctactacgcc     180
tcgtgggcca aggacggtt caccatctcg cgggacaact ccaagaacac tgtgtatctg     240
cagatgaaca gcctgagggc agaagatacc gccgtgtact actgcgcgag agatcgcttc     300
gtgggcgtgg acatctttga cccgtggggt caaggcaccc tggtcactgt ctcgagcgct     360
tctacaaagg gcccatcggt cttccccctg gcacctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
```

```
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260 cagggggaacg tcttctcatg ctccgtgatg catgaggctc tgcacaacca ctacacgcag     1320
aagagcctct ccctgtctcc gggtaaa                                          1347

<210> SEQ ID NO 32
<211> LENGTH: 446
<212> TYPE: PRT
<213> ORGANISM: Artificial Sequence
<220> FEATURE:
<223> OTHER INFORMATION: 11041 gH5 D54E (gH14) heavy chain (IgG4P)

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
```

```
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445
```

<210> SEQ ID NO 33
<211> LENGTH: 1338
<212> TYPE: DNA
<213> ORGANISM: Artificial Sequence
<220> FEATURE:
<223> OTHER INFORMATION: 11041 gH5 D54E (gH14) heavy chain (IgG4P)

<400> SEQUENCE: 33

```
gaggtgcagc tcgtggaaag cggaggagga ctggtgcagc caggagggtc cttgcggctt     60
agctgtgccg tgtccggctt ctccctgtcc tcctacgcca tgatctgggt ccgccaagct    120
cctgggaagg gcctcgaatg gattggtatt atcgacatcg agggatcaac ctactacgcc    180
tcgtgggcca agggacggtt caccatctcg cgggacaact ccaagaacac tgtgtatctg    240
cagatgaaca gcctgagggc agaagatacc gccgtgtact actgcgcgag agatcgcttc    300
gtgggcgtgg acatctttga cccgtggggt caaggcaccc tggtcactgt ctcgagcgct    360
tctacaaagg gcccctccgt gttccctctg gccccttgct cccggtccac ctccgagtct    420
accgccgctc tgggctgcct ggtcaaggac tacttccccg agcccgtgac agtgtcctgg    480
aactctggcg ccctgacctc cggcgtgcac accttccctg ccgtgctgca gtcctccggc    540
ctgtactccc tgtcctccgt cgtgaccgtg ccctcctcca gcctgggcac caagacctac    600
acctgtaacg tggaccacaa gccctccaac accaaggtgg acaagcgggt ggaatctaag    660
tacggcccct cctgcccccc ctgccctgcc cctgaatttc tgggcggacc ttccgtgttc    720
ctgttccccc caaagcccaa ggacaccctg atgatctccc ggacccccga agtgacctgc    780
gtggtggtgg acgtgtccca ggaagatccc gaggtccagt tcaattggta cgtggacggc    840
```

-continued

```
gtggaagtgc acaatgccaa gaccaagccc agagaggaac agttcaactc cacctaccgg     900
gtggtgtccg tgctgaccgt gctgcaccag gactggctga acggcaaaga gtacaagtgc     960
aaggtgtcca acaagggcct gccctccagc atcgaaaaga ccatctccaa ggccaagggc    1020
cagccccgcg agccccaggt gtacaccctg cccctagcc aggaagagat gaccaagaac    1080
caggtgtccc tgacctgtct ggtcaagggc ttctacccct ccgacattgc cgtggaatgg    1140
gagtccaacg gccagcccga gaacaactac aagaccaccc ccctgtgct ggacagcgac    1200 ggctccttct tcctgtactc tcggctgacc gtggacaagt cccggtggca ggaaggcaac    1260
gtcttctcct gctccgtgat gcacgaggcc ctgcacaacc actacaccca gaagtccctg    1320
tccctgagcc tgggcaag                                                  1338
```

```
<210> SEQ ID NO 34
<211> LENGTH: 112
<212> TYPE: PRT
<213> ORGANISM: Artificial Sequence
<220> FEATURE:
<223> OTHER INFORMATION: Rabbit 11041 VL-region

<400> SEQUENCE: 34

Ala Val Val Leu Thr Gln Thr Ala Ser Pro Val Ser Ala Pro Val Gly
1               5                   10                  15

Gly Thr Val Thr Ile Lys Cys Gln Ala Ser Glu Asp Ile Tyr Thr Asn
            20                  25                  30

Leu Ala Trp Tyr Gln Gln Lys Pro Gly Gln Pro Pro Lys Leu Leu Ile
        35                  40                  45

Tyr Trp Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Cys Val Tyr Gly Asn Ser
                85                  90                  95

Ala Asp Ser Arg Tyr Thr Phe Gly Gly Gly Thr Glu Val Val Val Lys
            100                 105                 110
```

```
<210> SEQ ID NO 35
<211> LENGTH: 336
<212> TYPE: DNA
<213> ORGANISM: Artificial Sequence
<220> FEATURE:
<223> OTHER INFORMATION: Rabbit 11041 VL-region

<400> SEQUENCE: 35
gccgtcgtgc tgacccagac tgcatccccc gtgtctgcac ctgtgggagg cacagtcacc      60
atcaagtgcc aggccagtga ggacatttac accaatttag cctggtatca acagaaacca     120
ggacagcctc ccaagctcct gatctactgg gcatccactc tggcatctgg ggtcccatcg     180
cggttcaaag gcagtggatc tgggacagag ttcactctca ccatcagcga cctggagtgt     240
gccgatgctg ccacttacta ctgtcaagcc tgtgtttatg gcaatagtgc tgatagtcgg     300
tatactttcg gcggagggac cgaggtggtg gtcaaa                              336
```

```
<210> SEQ ID NO 36
<211> LENGTH: 116
<212> TYPE: PRT
<213> ORGANISM: Artificial Sequence
<220> FEATURE:
<223> OTHER INFORMATION: Rabbit 11041 VH-region
```

<400> SEQUENCE: 36

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ile Trp Val Arg Gln Ala Pro Gly Glu Gly Leu Glu Trp Ile Gly
        35                  40                  45

Ile Ile Asp Ile Asp Gly Ser Thr Tyr Tyr Ala Ser Trp Ala Lys Gly
    50                  55                  60

Arg Phe Thr Ile Ser Arg Thr Ser Thr Thr Val Asp Leu Lys Ile Thr
65                  70                  75                  80

Ser Pro Thr Thr Gly Asp Thr Ala Thr Tyr Phe Cys Ala Arg Asp Arg
                85                  90                  95

Phe Val Gly Val Asp Ile Phe Asp Pro Trp Gly Pro Gly Thr Leu Val
            100                 105                 110

Thr Val Ser Ser
        115
```

<210> SEQ ID NO 37
<211> LENGTH: 348
<212> TYPE: DNA
<213> ORGANISM: Artificial Sequence
<220> FEATURE:
<223> OTHER INFORMATION: Rabbit 11041 VH-region

<400> SEQUENCE: 37

```
cagtcggtgg aggagtccgg gggtcgcctg gtcacgcctg gacacccct gacactcacc       60 tgcaccgtct ctggattctc cctcagtagc tatgcaatga tctgggtccg ccaggctcca      120 ggggagggc tggaatggat cggaatcatt gatattgatg ggagcacata ctacgcgagc      180
tgggcgaaag ccgattcac catctccaga acctcgacca cggtggatct gaaaatcacc      240
agtccgacaa ccgggacac ggccacctat ttctgtgcca gagatcgttt tgttggtgtt      300
gatatttttg atccctgggg cccaggcacc ctggtcaccg tctcgagc                  348
```

<210> SEQ ID NO 38
<211> LENGTH: 112
<212> TYPE: PRT
<213> ORGANISM: Artificial Sequence
<220> FEATURE:
<223> OTHER INFORMATION: 11041gL1 V-region

<400> SEQUENCE: 38

```
Ala Val Val Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Cys Val Tyr Gly Asn Ser
                85                  90                  95

Ala Asp Ser Arg Tyr Thr Phe Gly Gly Gly Thr Lys Val Glu Ile Lys
            100                 105                 110
```

```
<210> SEQ ID NO 39
<211> LENGTH: 112
<212> TYPE: PRT
<213> ORGANISM: Artificial Sequence
<220> FEATURE:
<223> OTHER INFORMATION: 11041 gL1 C91S V-region (gL2)

<400> SEQUENCE: 39

Ala Val Val Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ser
                85                  90                  95

Ala Asp Ser Arg Tyr Thr Phe Gly Gly Gly Thr Lys Val Glu Ile Lys
            100                 105                 110

<210> SEQ ID NO 40
<211> LENGTH: 112
<212> TYPE: PRT
<213> ORGANISM: Artificial Sequence
<220> FEATURE:
<223> OTHER INFORMATION: 11041 gL1 C91V V-region (gL3)

<400> SEQUENCE: 40

Ala Val Val Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Val Val Tyr Gly Asn Ser
                85                  90                  95

Ala Asp Ser Arg Tyr Thr Phe Gly Gly Gly Thr Lys Val Glu Ile Lys
            100                 105                 110

<210> SEQ ID NO 41
<211> LENGTH: 112
<212> TYPE: PRT
<213> ORGANISM: Artificial Sequence
<220> FEATURE:
<223> OTHER INFORMATION: 11041gL6 V-region

<400> SEQUENCE: 41

Ala Val Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
```

-continued

```
          35                40                45

Tyr Trp Ala Ser Thr Leu Ala Ser Gly Val Pro Ser Arg Phe Ser Gly
   50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Ala Cys Val Tyr Gly Asn Ser
              85                90                95

Ala Asp Ser Arg Tyr Thr Phe Gly Gly Gly Thr Lys Val Glu Ile Lys
          100                105                110

<210> SEQ ID NO 42
<211> LENGTH: 112
<212> TYPE: PRT
<213> ORGANISM: Artificial Sequence
<220> FEATURE:
<223> OTHER INFORMATION: 11041gL7 V-region

<400> SEQUENCE: 42

Ala Ile Gln Leu Thr Gln Ser Pro Ser Ser Leu Ser Ala Ser Val Gly
1                5                10                15

Asp Arg Val Thr Ile Thr Cys Gln Ala Ser Glu Asp Ile Tyr Thr Asn
              20                25                30

Leu Ala Trp Tyr Gln Gln Lys Pro Gly Lys Ala Pro Lys Leu Leu Ile
          35                40                45

Tyr Trp Ala Ser Thr Leu Ala Ser Gly Val Pro Ser Arg Phe Ser Gly
   50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Ala Cys Val Tyr Gly Asn Ser
              85                90                95

Ala Asp Ser Arg Tyr Thr Phe Gly Gly Gly Thr Lys Val Glu Ile Lys
          100                105                110

<210> SEQ ID NO 43
<211> LENGTH: 112
<212> TYPE: PRT
<213> ORGANISM: Artificial Sequence
<220> FEATURE:
<223> OTHER INFORMATION: 11041 gL1 N95D V-region (gL8)

<400> SEQUENCE: 43

Ala Val Val Leu Thr Gln Ser Pro Ser Ser Leu Ser Ala Ser Val Gly
1                5                10                15

Asp Arg Val Thr Ile Thr Cys Gln Ala Ser Glu Asp Ile Tyr Thr Asn
              20                25                30

Leu Ala Trp Tyr Gln Gln Lys Pro Gly Lys Ala Pro Lys Leu Leu Ile
          35                40                45

Tyr Trp Ala Ser Thr Leu Ala Ser Gly Val Pro Ser Arg Phe Ser Gly
   50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Ala Cys Val Tyr Gly Asp Ser
              85                90                95

Ala Asp Ser Arg Tyr Thr Phe Gly Gly Gly Thr Lys Val Glu Ile Lys
          100                105                110

<210> SEQ ID NO 44
<211> LENGTH: 112
```

```
<212> TYPE: PRT
<213> ORGANISM: Artificial Sequence
<220> FEATURE:
<223> OTHER INFORMATION: 11041 gL1 S96A V-region (gL9)

<400> SEQUENCE: 44

Ala Val Val Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Cys Val Tyr Gly Asn Ala
                85                  90                  95

Ala Asp Ser Arg Tyr Thr Phe Gly Gly Gly Thr Lys Val Glu Ile Lys
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: 11041 gL1 C91S S96A V-region (gL10)

<400> SEQUENCE: 45

Ala Val Val Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ala
                85                  90                  95

Ala Asp Ser Arg Tyr Thr Phe Gly Gly Gly Thr Lys Val Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: 11041 gL6 C91S V-region (gL11)

<400> SEQUENCE: 46

Ala Val Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
            20                  25                  30

Leu Ala Trp Tyr Gln Gln Lys Pro Gly Lys Ala Pro Lys Leu Leu Ile
        35                  40                  45

Tyr Trp Ala Ser Thr Leu Ala Ser Gly Val Pro Ser Arg Phe Ser Gly
```

```
        50              55              60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ser
                85                  90                  95

Ala Asp Ser Arg Tyr Thr Phe Gly Gly Gly Thr Lys Val Glu Ile Lys
                100                 105                 110
```

```
<210> SEQ ID NO 47
<211> LENGTH: 112
<212> TYPE: PRT
<213> ORGANISM: Artificial Sequence
<220> FEATURE:
<223> OTHER INFORMATION: 11041 gL7 C91S V-region (gL12)

<400> SEQUENCE: 47

Ala Ile Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
                20                  25                  30

Leu Ala Trp Tyr Gln Gln Lys Pro Gly Lys Ala Pro Lys Leu Leu Ile
            35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ser
                85                  90                  95

Ala Asp Ser Arg Tyr Thr Phe Gly Gly Gly Thr Lys Val Glu Ile Lys
                100                 105                 110
```

```
<210> SEQ ID NO 48
<211> LENGTH: 112
<212> TYPE: PRT
<213> ORGANISM: Artificial Sequence
<220> FEATURE:
<223> OTHER INFORMATION: 11041 gL7 C91S S96A V-region (gL14)

<400> SEQUENCE: 48

Ala Ile Gln Leu Thr Gln Ser Pro Ser Ser Leu Ser Ala Ser Val Gly
1               5                   10                  15

Asp Arg Val Thr Ile Thr Cys Gln Ala Ser Glu Asp Ile Tyr Thr Asn
                20                  25                  30

Leu Ala Trp Tyr Gln Gln Lys Pro Gly Lys Ala Pro Lys Leu Leu Ile
            35                  40                  45

Tyr Trp Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ser Val Tyr Gly Asn Ala
                85                  90                  95

Ala Asp Ser Arg Tyr Thr Phe Gly Gly Gly Thr Lys Val Glu Ile Lys
                100                 105                 110
```

```
<210> SEQ ID NO 49
<211> LENGTH: 119
<212> TYPE: PRT
<213> ORGANISM: Artificial Sequence
<220> FEATURE:
```

-continued

<223> OTHER INFORMATION: 11041gH1 V-region

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
            115
```

<210> SEQ ID NO 50
<211> LENGTH: 119
<212> TYPE: PRT
<213> ORGANISM: Artificial Sequence
<220> FEATURE:
<223> OTHER INFORMATION: 11041 gH1 G55A V-region (gH2)

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Asp Ala Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
            115
```

<210> SEQ ID NO 51
<211> LENGTH: 119
<212> TYPE: PRT
<213> ORGANISM: Artificial Sequence
<220> FEATURE:
<223> OTHER INFORMATION: 11041 gH1 D54E V-region (gH3)

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
```

```
            35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: 11041 gH1 D107E V-region (gH4)

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
            35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Glu Pro Trp Gly Gln Gly
            100                 105                 110

Thr Leu Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: 11041gH5 V-region

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
            35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95
```

```
Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: 11041gH8 V-region

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: 11041gH9 V-region

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 56
<211> LENGTH: 119
<212> TYPE: PRT
<213> ORGANISM: Artificial Sequence
```

<220> FEATURE:
<223> OTHER INFORMATION: 11041gH11 V-region

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Val
        35                  40                  45

Gly Ile Ile Asp Ile Asp Gly Ser Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: 11041gH12 V-region

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Ser Ile Ile Asp Ile Asp Gly Ser Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: 11041 gH8 D54E V-region (gH15)

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: 11041 gH11 D54E V-region (gH17)

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Val
        35                  40                  45

Gly Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Artificial Sequence
<220> FEATURE:
<223> OTHER INFORMATION: 11041 gH12 D54E V-region (gH18)

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Ser Ile Ile Asp Ile Glu Gly Ser Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

-continued

```
Arg Asp Arg Phe Val Gly Val Asp Ile Phe Asp Pro Trp Gly Gln Gly
            100                 105                 110

Thr Leu Val Thr Val Ser Ser
        115

<210> SEQ ID NO 61
<211> LENGTH: 107
<212> TYPE: PRT
<213> ORGANISM: Artificial Sequence
<220> FEATURE:
<223> OTHER INFORMATION: Human IGKV1D-13 IGKJ4 acceptor framework

<400> SEQUENCE: 61

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 62
<211> LENGTH: 321
<212> TYPE: DNA
<213> ORGANISM: Artificial Sequence
<220> FEATURE:
<223> OTHER INFORMATION: Human IGKV1D-13 IGKJ4 acceptor framework

<400> SEQUENCE: 62
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctctcac tttcggcgga     300
gggaccaagg tggagatcaa a                                               321

<210> SEQ ID NO 63
<211> LENGTH: 112
<212> TYPE: PRT
<213> ORGANISM: Artificial Sequence
<220> FEATURE:
<223> OTHER INFORMATION: Human IGHV3-66 IGHJ4 acceptor framework

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45
```

```
Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Phe Asp Tyr Trp Gly Gln Gly Thr Leu Val Thr Val Ser Ser
                100                 105                 110
```

```
<210> SEQ ID NO 64
<211> LENGTH: 336
<212> TYPE: DNA
<213> ORGANISM: Artificial Sequence
<220> FEATURE:
<223> OTHER INFORMATION: Human IGHV3-66 IGHJ4 acceptor framework

<400> SEQUENCE: 64
gaggtgcagc tggtggagtc tggggggaggc ttggtccagc ctggggggtc cctgagactc      60
tcctgtgcag cctctggatt caccgtcagt agcaactaca tgagctgggt ccgccaggct     120
ccagggaagg ggctggagtg ggtctcagtt atttatagcg gtggtagcac atactacgca     180
gactccgtga aggggcagatt caccatctcc agagacaatt ccaagaacac gctgtatctt     240
caaatgaaca gcctgagagc cgaggacacg gctgtgtatt actgtgcgag atactttgac     300
tactggggcc aaggaaccct ggtcaccgtc tcctca                                336
```

```
<210> SEQ ID NO 65
<211> LENGTH: 11
<212> TYPE: PRT
<213> ORGANISM: Artificial Sequence
<220> FEATURE:
<223> OTHER INFORMATION: 11070 CDRL1

<400> SEQUENCE: 65

Lys Ala Ser Lys Thr Ile Ser Lys Tyr Leu Ala
1               5                   10
```

```
<210> SEQ ID NO 66
<211> LENGTH: 7
<212> TYPE: PRT
<213> ORGANISM: Artificial Sequence
<220> FEATURE:
<223> OTHER INFORMATION: 11070 CDRL2

<400> SEQUENCE: 66

Ser Gly Ser Thr Leu Gln Ser
1               5
```

```
<210> SEQ ID NO 67
<211> LENGTH: 9
<212> TYPE: PRT
<213> ORGANISM: Artificial Sequence
<220> FEATURE:
<223> OTHER INFORMATION: 11070 CDRL3

<400> SEQUENCE: 67

Gln Gln His Asn Glu Tyr Pro Leu Thr
1               5
```

```
<210> SEQ ID NO 68
<211> LENGTH: 10
<212> TYPE: PRT
<213> ORGANISM: Artificial Sequence
<220> FEATURE:
```

```
<223> OTHER INFORMATION: 11070 CDRH1

<400> SEQUENCE: 68

Gly Phe Ser Leu Thr Ser Tyr Ser Val His
1               5                   10

<210> SEQ ID NO 69
<211> LENGTH: 16
<212> TYPE: PRT
<213> ORGANISM: Artificial Sequence
<220> FEATURE:
<223> OTHER INFORMATION: 11070 CDRH2

<400> SEQUENCE: 69

Arg Met Trp Ser Asp Gly Asp Thr Ser Tyr Asn Thr Ala Phe Thr Ser
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: 11070 CDRH3

<400> SEQUENCE: 70

Ser Leu Asp Phe Tyr Tyr Asp Thr Thr Leu Ala Phe
1               5                   10

<210> SEQ ID NO 71
<211> LENGTH: 16
<212> TYPE: PRT
<213> ORGANISM: Artificial Sequence
<220> FEATURE:
<223> OTHER INFORMATION: 11070 CDRH2 (not mutated)

<400> SEQUENCE: 71

Arg Met Trp Ser Asp Gly Asp Thr Ser Tyr Asn Ser Ala Phe Thr Ser
1               5                   10                  15

<210> SEQ ID NO 72
<211> LENGTH: 107
<212> TYPE: PRT
<213> ORGANISM: Artificial Sequence
<220> FEATURE:
<223> OTHER INFORMATION: 11070gL7 V-region

<400> SEQUENCE: 72

Asp Ile Gln Met Thr Gln Ser Pro Ser Ser Val Ser Ala Ser Val Gly
1               5                   10                  15

Asp Arg Val Thr Ile Thr Cys Lys Ala Ser Lys Thr Ile Ser Lys Tyr
            20                  25                  30

Leu Ala Trp Tyr Gln Gln Lys Pro Gly Lys Ala Asn Lys Leu Leu Ile
            35                  40                  45

Tyr Ser Gly Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 73
```

-continued

```
<211> LENGTH: 321
<212> TYPE: DNA
<213> ORGANISM: Artificial Sequence
<220> FEATURE:
<223> OTHER INFORMATION: 11070gL7 V-region

<400> SEQUENCE: 73
gacattcaga tgactcagtc gccttcgtcc gtgagcgcca gcgtcggaga cagagtgaca      60
atcacctgta aagcgtccaa gaccatctcc aagtacctgg cttggtatca gcagaaaccg     120
gggaaggcca acaagttgct tatctactcc ggttctactc tccaatcggg agtgccaagc     180 cggtttttccg ggtccggatc aggcaccgac ttcacccctca ccatctcatc cctgcaaccg    240
gaggatttcg ccacgtacta ctgccagcag cacaacgaat accccctgac cttcggccaa     300
ggaactaagc tggaaattaa g                                               321

<210> SEQ ID NO 74
<211> LENGTH: 120
<212> TYPE: PRT
<213> ORGANISM: Artificial Sequence
<220> FEATURE:
<223> OTHER INFORMATION: 11070gH16 V-region

<400> SEQUENCE: 74

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Pro Gly Lys Gly Leu Glu Trp Ile
        35                  40                  45

Gly Arg Met Trp Ser Asp Gly Asp Thr Ser Tyr Asn Thr Ala Phe Thr
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ser Leu Asp Phe Tyr Tyr Asp Thr Thr Leu Ala Phe Trp Gly Gln
            100                 105                 110

Gly Thr Thr Val Thr Val Ser Ser
        115                 120

<210> SEQ ID NO 75
<211> LENGTH: 360
<212> TYPE: DNA
<213> ORGANISM: Artificial Sequence
<220> FEATURE:
<223> OTHER INFORMATION: 11070gH16 V-region

<400> SEQUENCE: 75
gaggtgcagc tgcaagaatc cggtcctggc ctcgtgaagc cgtcgcagac cttgagcctg      60
acctgtactg tgtccggatt cagcctcaca tcctactcgg tgcactgggt cagacagcat     120
cccggaaaag gcctggaatg gattgggagg atgtggtctg atggagacac tcctacaac      180 acggcgttca ccagccggct gaccatctcc cgcgacacct ccaagaacca agtgtcgctt     240
aagctgtcct cagtcactgc cgccgatacc gcagtgtatt actgcgctcg gtcactggac     300
ttttactacg acaccaccct ggccttctgg ggacagggga ctactgtgac tgtctcgagc     360

<210> SEQ ID NO 76
<211> LENGTH: 214
```

```
<212> TYPE: PRT
<213> ORGANISM: Artificial Sequence
<220> FEATURE:
<223> OTHER INFORMATION: 11070gL7 Light chain

<400> SEQUENCE: 76

Asp Ile Gln Met Thr Gln Ser Pro Ser Ser Val Ser Ala Ser Val Gly
1               5                   10                  15

Asp Arg Val Thr Ile Thr Cys Lys Ala Ser Lys Thr Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 77
<211> LENGTH: 642
<212> TYPE: DNA
<213> ORGANISM: Artificial Sequence
<220> FEATURE:
<223> OTHER INFORMATION: 11070gL7 Light chain

<400> SEQUENCE: 77
gacattcaga tgactcagtc gccttcgtcc gtgagcgcca gcgtcggaga cagagtgaca      60
atcacctgta aagcgtccaa gaccatctcc aagtacctgg cttggtatca gcagaaaccg     120
gggaaggcca acaagttgct tatctactcc ggttctactc tccaatcggg agtgccaagc     180
cggttttccg gtccggatc aggcaccgac ttcaccctca ccatctcatc cctgcaaccg     240
gaggatttcg ccacgtacta ctgccagcag cacaacgaat accccctgac cttcggccaa     300
ggaactaagc tggaaattaa gcgtacggtg gccgctccct ccgtgttcat cttcccaccc     360
tccgacgagc agctgaagtc cggcaccgcc tccgtcgtgt gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
```

-continued

```
ctgtccagcc ccgtgaccaa gtccttcaac cggggcgagt gc                    642
```

```
<210> SEQ ID NO 78
<211> LENGTH: 223
<212> TYPE: PRT
<213> ORGANISM: Artificial Sequence
<220> FEATURE:
<223> OTHER INFORMATION: 11070gH16 Fab Heavy chain

<400> SEQUENCE: 78

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Pro Gly Lys Gly Leu Glu Trp Ile
        35                  40                  45

Gly Arg Met Trp Ser Asp Gly Asp Thr Ser Tyr Asn Thr Ala Phe Thr
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Ser Leu Asp Phe Tyr Tyr Asp Thr Thr Leu Ala Phe Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
    210                 215                 220
```

```
<210> SEQ ID NO 79
<211> LENGTH: 669
<212> TYPE: DNA
<213> ORGANISM: Artificial Sequence
<220> FEATURE:
<223> OTHER INFORMATION: 11070gH16 Fab Heavy chain

<400> SEQUENCE: 79
gaggtgcagc tgcaagaatc cggtcctggc ctcgtgaagc cgtcgcagac cttgagcctg      60
acctgtactg tgtccggatt cagcctcaca tcctactcgg tgcactgggt cagacagcat     120
cccggaaaag gcctggaatg gattgggagg atgtggtctg atggagacac ctcctacaac     180
acggcgttca ccagccggct gaccatctcc cgcgacacct ccaagaacca agtgtcgctt     240
aagctgtcct cagtcactgc cgccgatacc gcagtgtatt actgcgctcg gtcactggac     300
ttttactacg acaccaccct ggccttctgg ggacagggga ctactgtgac tgtctcgagc     360
gcgtccacaa agggcccatc ggtcttcccc ctggcaccct cctccaagag cacctctggg     420
ggcacagcgg ccctgggctg cctggtcaag gactacttcc ccgaaccagt gacggtgtcg     480
```

-continued

```
tggaactcag gtgccctgac cagcggcgtt cacaccttcc cggctgtcct acagtcttca        540
ggactctact ccctgagcag cgtggtgacc gtgccctcca gcagcttggg cacccagacc        600
tacatctgca acgtgaatca caagcccagc aacaccaagg tcgataagaa agttgagccc        660
aaatcttgt                                                                669
```

```
<210> SEQ ID NO 80
<211> LENGTH: 450
<212> TYPE: PRT
<213> ORGANISM: Artificial Sequence
<220> FEATURE:
<223> OTHER INFORMATION: 11070gH16 IgG1 Heavy chain

<400> SEQUENCE: 80

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Pro Gly Lys Gly Leu Glu Trp Ile
        35                  40                  45

Gly Arg Met Trp Ser Asp Gly Asp Thr Ser Tyr Asn Thr Ala Phe Thr
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ser Leu Asp Phe Tyr Tyr Asp Thr Thr Leu Ala Phe Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 81
<211> LENGTH: 1350
<212> TYPE: DNA
<213> ORGANISM: Artificial Sequence
<220> FEATURE:
<223> OTHER INFORMATION: 11070gH16 IgG1 Heavy chain

<400> SEQUENCE: 81
gaggtgcagc tgcaagaatc cggtcctggc tcgtgaagc cgtcgcagac cttgagcctg        60
acctgtactg tgtccggatt cagcctcaca tcctactcgg tgcactgggt cagacagcat       120
cccggaaaag gcctggaatg gattgggagg atgtggtctg atggagacac ctcctacaac       180
acggcgttca ccagccggct gaccatctcc cgcgacacct ccaagaacca agtgtcgctt       240
aagctgtcct cagtcactgc cgccgatacc gcagtgtatt actgcgctcg gtcactggac       300
ttttactacg acaccaccct ggccttctgg ggacagggga ctactgtgac tgtctcgagc       360
gcttctacaa agggcccatc ggtcttcccc ctggcaccct cctccaagag cacctctggg       420
ggcacagcgg ccctgggctg cctggtcaag gactacttcc ccgaaccggt gacggtgtcg       480
tggaactcag gcgccctgac cagcggcgtg cacaccttcc cggctgtcct acagtcctca       540
ggactctact ccctcagcag cgtggtgacc gtgccctcca gcagcttggg cacccagacc       600
tacatctgca acgtgaatca caagcccagc aacaccaagg tggacaagaa agttgagccc       660
aaatcttgtg acaaaactca cacatgccca ccgtgcccag cacctgaact cctggggga       720 ccgtcagtct tcctcttccc cccaaaaccc aaggacaccc tcatgatctc ccggaccct       780 gaggtcacat gcgtggtggt ggacgtgagc cacgaagacc ctgaggtcaa gttcaactgg       840
tacgtggacg gcgtggaggt gcataatgcc aagacaaagc cgcgggagga gcagtacaac       900
agcacgtacc gtgtggtcag cgtcctcacc gtcctgcacc aggactggct gaatggcaag       960
gagtacaagt gcaaggtctc caacaaagcc ctcccagccc ccatcgagaa aaccatctcc      1020
aaagccaaag gcagccccg agaaccacag gtgtacaccc tgcccccatc ccgggatgag      1080
ctgaccaaga accaggtcag cctgacctgc ctggtcaaag gcttctatcc cagcgacatc      1140
gccgtggagt gggagagcaa tgggcagccg gagaacaact acaagaccac gcctcccgtg      1200
ctggactccg acggctcctt cttcctctac agcaagctca ccgtggacaa gagcaggtgg      1260
```

-continued

```
cagcagggga acgtcttctc atgctccgtg atgcatgagg ctctgcacaa ccactacacg    1320
cagaagagcc tctccctgtc tccgggtaaa                                      1350

<210> SEQ ID NO 82
<211> LENGTH: 447
<212> TYPE: PRT
<213> ORGANISM: Artificial Sequence
<220> FEATURE:
<223> OTHER INFORMATION: 11070gH16 IgG4P Heavy chain

<400> SEQUENCE: 82

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Pro Gly Lys Gly Leu Glu Trp Ile
        35                  40                  45

Gly Arg Met Trp Ser Asp Gly Asp Thr Ser Tyr Asn Thr Ala Phe Thr
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ser Leu Asp Phe Tyr Tyr Asp Thr Thr Leu Ala Phe Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 83
<211> LENGTH: 1341
<212> TYPE: DNA
<213> ORGANISM: Artificial Sequence
<220> FEATURE:
<223> OTHER INFORMATION: 11070gH16 IgG4P Heavy chain

<400> SEQUENCE: 83

```
gaggtgcagc tgcaagaatc cggtcctggc ctcgtgaagc cgtcgcagac cttgagcctg      60
acctgtactg tgtccggatt cagcctcaca tcctactcgg tgcactgggt cagacagcat     120
cccggaaaag gcctggaatg gattgggagg atgtggtctg atggagacac tcctacaac      180 acggcgttca ccagccggct gaccatctcc cgcgacacct ccaagaacca agtgtcgctt     240
aagctgtcct cagtcactgc cgccgatacc gcagtgtatt actgcgctcg gtcactggac     300
ttttactacg acaccaccct ggccttctgg ggacagggga ctactgtgac tgtctcgagc     360
gcttctacaa agggcccctc cgtgttccct ctggcccctt gctcccggtc cacctccgag     420
tctaccgccg ctctgggctg cctggtcaag gactacttcc ccgagcccgt gacagtgtcc     480
tggaactctg gcgccctgac ctccggcgtg cacaccttcc ctgccgtgct gcagtcctcc     540
ggcctgtact ccctgtcctc cgtcgtgacc gtgccctcct ccagcctggg caccaagacc     600
tacacctgta acgtggacca caagccctcc aacaccaagg tggacaagcg ggtggaatct     660
aagtacggcc ctccctgccc ccctgcccct gccctgaat ttctgggcgg accttccgtg     720
ttcctgttcc ccccaaagcc caaggacacc ctgatgatct cccggacccc cgaagtgacc     780
tgcgtggtgg tggacgtgtc ccaggaagat cccgaggtcc agttcaattg gtacgtggac     840
ggcgtggaag tgcacaatgc caagaccaag cccagagagg aacagttcaa ctccacctac     900
cgggtggtgt ccgtgctgac cgtgctgcac caggactggc tgaacggcaa agagtacaag     960
tgcaaggtgt ccaacaaggg cctgccctcc agcatcgaaa agaccatctc caaggccaag    1020
ggccagcccc gcgagcccca ggtgtacacc ctgccccta gccaggaaga gatgaccaag    1080
aaccaggtgt ccctgacctg tctggtcaag ggcttctacc cctccgacat tgccgtggaa    1140
tgggagtcca acggccagcc cgagaacaac tacaagacca ccccccctgt gctggacagc    1200
gacggctcct tcttcctgta ctctcggctg accgtggaca gtcccggtg caggaaggc    1260 aacgtcttct cctgctccgt gatgcacgag gccctgcaca accactacac ccagaagtcc    1320
ctgtccctga gcctgggcaa g                                              1341
```

<210> SEQ ID NO 84
<211> LENGTH: 107
<212> TYPE: PRT

<213> ORGANISM: Artificial Sequence
<220> FEATURE:
<223> OTHER INFORMATION: Rat Ab 11070 VL-region

<400> SEQUENCE: 84

Asp Ile Val Met Thr Gln Thr Pro Ser Asn Leu Ala Ala Ser Pro Gly
1               5                   10                  15

Glu Ser Val Ser Ile Asn Cys Lys Ala Ser Lys Thr Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Ser Thr Asp Phe Thr Leu Thr Ile Arg Asn Leu Glu Pro
65                  70                  75                  80

Glu Asp Phe Gly Leu Tyr Tyr Cys Gln Gln His Asn Glu Tyr Pro Leu
                85                  90                  95

Thr Phe Gly Ser Gly Thr Lys Leu Glu Ile Lys
            100                 105

<210> SEQ ID NO 85
<211> LENGTH: 321
<212> TYPE: DNA
<213> ORGANISM: Artificial Sequence
<220> FEATURE:
<223> OTHER INFORMATION: Rat Ab 11070 VL-region

<400> SEQUENCE: 85
gatattgtga tgacacagac tccatctaat cttgctgcct ctcctggaga aagtgtttcc        60
atcaattgca aggcaagtaa gaccattagc aagtatttag cctggtatca acagaaacct       120
gggaaagcaa ataagcttct tatctattct gggtcaactt tgcaatctgg aactccatcg       180
aggttcagtg gcagtggatc tagtacagat ttcactctca ccatcagaaa cctggagcct       240
gaagattttg gactctatta ctgtcaacag cataatgaat acccgctcac gttcggttct       300
gggaccaagt tggaaataaa a                                                  321

<210> SEQ ID NO 86
<211> LENGTH: 120
<212> TYPE: PRT
<213> ORGANISM: Artificial Sequence
<220> FEATURE:
<223> OTHER INFORMATION: Rat Ab 11070 VH-region

<400> SEQUENCE: 86

Glu Val Gln Leu Gln Glu Ser Gly Pro Gly Leu Val Gln Pro Ser Gln
1               5                   10                  15

Thr Leu Ser Pro Thr Cys Thr Val Ser Gly Phe Ser Leu Thr Ser Tyr
            20                  25                  30

Ser Val His Trp Val Arg Gln His Ser Gly Lys Ser Leu Glu Trp Met
        35                  40                  45

Gly Arg Met Trp Ser Asp Gly Asp Thr Ser Tyr Asn Ser Ala Phe Thr
    50                  55                  60

Ser Arg Leu Ser Ile Thr Arg Asp Thr Ser Lys Ser Gln Val Phe Leu
65                  70                  75                  80

Lys Met Asn Ser Leu Gln Thr Glu Asp Thr Gly Thr Tyr Tyr Cys Ala
                85                  90                  95

Arg Ser Leu Asp Phe Tyr Tyr Asp Thr Thr Leu Ala Phe Trp Gly Pro
            100                 105                 110

```
Gly Thr Thr Val Thr Val Ser Ser
        115             120

<210> SEQ ID NO 87
<211> LENGTH: 360
<212> TYPE: DNA
<213> ORGANISM: Artificial Sequence
<220> FEATURE:
<223> OTHER INFORMATION: Rat Ab 11070 VH-region

<400> SEQUENCE: 87
gaggtgcagc tgcaggagtc aggacctggg ctggtgcagc cctcacagac cctgtccccc      60
acctgcactg tctctgggtt ctcactaact agttacagtg tacactgggt tcgccagcat     120
tcaggaaaga gtctggaatg gatgggaaga atgtggagtg atggagacac atcatataat     180
tcagcgttca catcccgatt gagcatcact agggacacct ccaagagcca agttttctta     240
aaaatgaaca gtctgcaaac tgaagacaca ggcacttact actgtgccag aagtctcgat     300
ttttactatg atactactct tgccttctgg ggcccaggaa ccacggtcac cgtctcgagt     360

<210> SEQ ID NO 88
<211> LENGTH: 107
<212> TYPE: PRT
<213> ORGANISM: Artificial Sequence
<220> FEATURE:
<223> OTHER INFORMATION: 11070gL1 V-region

<400> SEQUENCE: 88

Asp Ile Val Met Thr Gln Ser Pro Ser Ser Val Ser Ala Ser Val Gly
1               5                   10                  15

Asp Arg Val Thr Ile Thr Cys Lys Ala Ser Lys Thr Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Ser Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Leu
                85                  90                  95

Thr Phe Gly Gln Gly Thr Lys Leu Glu Ile Lys
            100                 105

<210> SEQ ID NO 89
<211> LENGTH: 120
<212> TYPE: PRT
<213> ORGANISM: Artificial Sequence
<220> FEATURE:
<223> OTHER INFORMATION: 11070gH1 V-region

<400> SEQUENCE: 89

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Ser Val His Trp Val Arg Gln His Ser Gly Lys Gly Leu Glu Trp Met
        35                  40                  45

Gly Arg Met Trp Ser Asp Gly Asp Thr Ser Tyr Asn Ser Ala Phe Thr
    50                  55                  60
```

```
Ser Arg Leu Thr Ile Ser Arg Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ser Leu Asp Phe Tyr Tyr Asp Thr Thr Leu Ala Phe Trp Gly Gln
                100                 105                 110

Gly Thr Thr Val Thr Val Ser Ser
        115                 120

<210> SEQ ID NO 90
<211> LENGTH: 120
<212> TYPE: PRT
<213> ORGANISM: Artificial Sequence
<220> FEATURE:
<223> OTHER INFORMATION: 11070gH13 V-region (gH1 S61T)

<400> SEQUENCE: 90

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
                20                  25                  30

Ser Val His Trp Val Arg Gln His Ser Gly Lys Gly Leu Glu Trp Met
        35                  40                  45

Gly Arg Met Trp Ser Asp Gly Asp Thr Ser Tyr Asn Thr Ala Phe Thr
        50                  55                  60

Ser Arg Leu Thr Ile Ser Arg Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ser Leu Asp Phe Tyr Tyr Asp Thr Thr Leu Ala Phe Trp Gly Gln
                100                 105                 110

Gly Thr Thr Val Thr Val Ser Ser
        115                 120

<210> SEQ ID NO 91
<211> LENGTH: 107
<212> TYPE: PRT
<213> ORGANISM: Artificial Sequence
<220> FEATURE:
<223> OTHER INFORMATION: Human IGKV1-12 IGKJ2 acceptor framework

<400> SEQUENCE: 91

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
                100                 105

<210> SEQ ID NO 92
```

```
<211> LENGTH: 321
<212> TYPE: DNA
<213> ORGANISM: Artificial Sequence
<220> FEATURE:
<223> OTHER INFORMATION: Human IGKV1-12 IGKJ2 acceptor framework

<400> SEQUENCE: 92
gacatccaga tgacccagtc tccatcttcc gtgtctgcat ctgtaggaga cagagtcacc        60
atcacttgtc gggcgagtca gggtattagc agctggttag cctggtatca gcagaaacca       120
gggaaagccc ctaagctcct gatctatgct gcatccagtt tgcaaagtgg ggtcccatca       180
aggttcagcg gcagtggatc tgggacagat ttcactctca ccatcagcag cctgcagcct       240
gaagattttg caacttacta ttgtcaacag gctaacagtt tcccttacac ttttggccag       300
gggaccaagc tggagatcaa a                                                  321

<210> SEQ ID NO 93
<211> LENGTH: 119
<212> TYPE: PRT
<213> ORGANISM: Artificial Sequence
<220> FEATURE:
<223> OTHER INFORMATION: Human IGHV4-31 IGHJ6 acceptor framework

<400> SEQUENCE: 93

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Tyr Tyr Tyr Tyr Gly Met Asp Val Trp Gly Gln Gly
            100                 105                 110

Thr Thr Val Thr Val Ser Ser
        115

<210> SEQ ID NO 94
<211> LENGTH: 357
<212> TYPE: DNA
<213> ORGANISM: Artificial Sequence
<220> FEATURE:
<223> OTHER INFORMATION: Human IGHV4-31 IGHJ6 acceptor framework

<400> SEQUENCE: 94
caggtgcagc tgcaggagtc gggcccagga ctggtgaagc cttcacagac cctgtccctc        60
acctgcactg tctctggtgg ctccatcagc agtggtggtt actactggag ctggatccgc       120
cagcacccag gaaagggcct ggagtggatt gggtacatct attacagtgg gagcacctac       180
tacaacccgt ccctcaagag tcgagttacc atatcagtag acacgtctaa gaaccagttc       240
tccctgaagc tgagctctgt gactgccgcg gacacggccg tgtattactg tgcgagatac       300
tactactact acggtatgga cgtctggggg caagggacca cggtcaccgt ctcctca          357

<210> SEQ ID NO 95
<211> LENGTH: 13
```

<212> TYPE: PRT
<213> ORGANISM: Artificial Sequence
<220> FEATURE:
<223> OTHER INFORMATION: Peptide 72-84

<400> SEQUENCE: 95

Val Arg Leu Ile Gly Glu Lys Leu Phe His Gly Val Ser
1               5                   10

<210> SEQ ID NO 96
<211> LENGTH: 14
<212> TYPE: PRT
<213> ORGANISM: Artificial Sequence
<220> FEATURE:
<223> OTHER INFORMATION: IL22 peptide 72-85

<400> SEQUENCE: 96

Val Arg Leu Ile Gly Glu Lys Leu Phe His Gly Val Ser Met
1               5                   10

<210> SEQ ID NO 97
<211> LENGTH: 10
<212> TYPE: PRT
<213> ORGANISM: Artificial Sequence
<220> FEATURE:
<223> OTHER INFORMATION: IL22 peptide 75-84

<400> SEQUENCE: 97

Ile Gly Glu Lys Leu Phe His Gly Val Ser
1               5                   10

<210> SEQ ID NO 98
<211> LENGTH: 11
<212> TYPE: PRT
<213> ORGANISM: Artificial Sequence
<220> FEATURE:
<223> OTHER INFORMATION: IL22 peptide 75-85

<400> SEQUENCE: 98

Ile Gly Glu Lys Leu Phe His Gly Val Ser Met
1               5                   10

<210> SEQ ID NO 99
<211> LENGTH: 9
<212> TYPE: PRT
<213> ORGANISM: Artificial Sequence
<220> FEATURE:
<223> OTHER INFORMATION: IL22 peptide 76-84

<400> SEQUENCE: 99

Gly Glu Lys Leu Phe His Gly Val Ser
1               5

<210> SEQ ID NO 100
<211> LENGTH: 6
<212> TYPE: PRT
<213> ORGANISM: Artificial Sequence
<220> FEATURE:
<223> OTHER INFORMATION: IL22 peptide 80-85

<400> SEQUENCE: 100

Phe His Gly Val Ser Met
1               5

<210> SEQ ID NO 101
<211> LENGTH: 14
<212> TYPE: PRT

-continued

```
<213> ORGANISM: Artificial Sequence
<220> FEATURE:
<223> OTHER INFORMATION: IL22 peptide 126-139

<400> SEQUENCE: 101

Ser Asn Arg Leu Ser Thr Cys His Ile Glu Gly Asp Asp Leu
1               5                   10

<210> SEQ ID NO 102
<211> LENGTH: 11
<212> TYPE: PRT
<213> ORGANISM: Artificial Sequence
<220> FEATURE:
<223> OTHER INFORMATION: IL22 peptide 101-111

<400> SEQUENCE: 102

Glu Glu Val Leu Phe Pro Gln Ser Asp Arg Phe
1               5                   10

<210> SEQ ID NO 103
<211> LENGTH: 13
<212> TYPE: PRT
<213> ORGANISM: Artificial Sequence
<220> FEATURE:
<223> OTHER INFORMATION: IL22 peptide 103-115

<400> SEQUENCE: 103

Val Leu Phe Pro Gln Ser Asp Arg Phe Gln Pro Tyr Met
1               5                   10

<210> SEQ ID NO 104
<211> LENGTH: 15
<212> TYPE: PRT
<213> ORGANISM: Artificial Sequence
<220> FEATURE:
<223> OTHER INFORMATION: IL22 peptide 103-117

<400> SEQUENCE: 104

Val Leu Phe Pro Gln Ser Asp Arg Phe Gln Pro Tyr Met Gln Glu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: IL22 peptide 43-58

<400> SEQUENCE: 105

Asp Lys Ser Asn Phe Gln Gln Pro Tyr Ile Thr Asn Arg Thr Phe Met
1               5                   10                  15

<210> SEQ ID NO 106
<211> LENGTH: 13
<212> TYPE: PRT
<213> ORGANISM: Artificial Sequence
<220> FEATURE:
<223> OTHER INFORMATION: IL22 peptide 105-117

<400> SEQUENCE: 106

Phe Pro Gln Ser Asp Arg Phe Gln Pro Tyr Met Gln Glu
1               5                   10
```